(12) United States Patent
Bublewitz et al.

(10) Patent No.: US 7,812,065 B2
(45) Date of Patent: Oct. 12, 2010

(54) DENTAL IMPRESSION MASSES, HARDENED PRODUCTS PRODUCED FROM THEM, AND USE OF SURFACTANTS FOR THE PRODUCTION OF DENTAL IMPRESSION MASSES

(75) Inventors: Alexander Bublewitz, Herborn (DE); Jens-Peter Reber, Meinerzhagen (DE)

(73) Assignee: Kettenbach GmbH & Co., KG, Eschenburg (DE)

( * ) Notice: Subject to any disclaimer, the term of this patent is extended or adjusted under 35 U.S.C. 154(b) by 25 days.

(21) Appl. No.: 12/087,319

(22) PCT Filed: Jan. 5, 2007

(86) PCT No.: PCT/EP2007/000066

§ 371 (c)(1),
(2), (4) Date: Jul. 1, 2008

(87) PCT Pub. No.: WO2007/080071

PCT Pub. Date: Jul. 19, 2007

(65) Prior Publication Data

US 2008/0319100 A1    Dec. 25, 2008

(30) Foreign Application Priority Data

Jan. 9, 2006  (DE) ................ 10 2006 001 126

(51) Int. Cl.
*A61K 6/10* (2006.01)
*A61C 13/00* (2006.01)
*C09K 3/00* (2006.01)

(52) U.S. Cl. ................ 523/109; 264/16; 106/35

(58) Field of Classification Search ............. 523/109; 264/16; 106/35
See application file for complete search history.

(56) References Cited

U.S. PATENT DOCUMENTS

| | | | |
|---|---|---|---|
| 991,572 A | 5/1911 | Weisenstein | |
| 1,079,042 A | 11/1913 | Duncan | |
| 1,103,717 A | 7/1914 | Walton et al. | |
| 1,942,600 A | 1/1934 | Hornung | |
| 2,074,294 A | 3/1937 | Woodruff | |
| 2,599,604 A | 6/1952 | Bauer et al. | |
| 2,887,177 A | 5/1959 | Mund et al. | |
| 2,890,796 A | 6/1959 | Blood | |
| 2,914,785 A | 12/1959 | Ela | |
| 2,942,127 A | 6/1960 | Harse | |
| 3,019,854 A | 3/1962 | O'Bryant | |
| 3,025,963 A | 3/1962 | Bauer | |
| 3,209,917 A | 10/1965 | Yelinek | |
| 3,442,067 A | 5/1969 | Swenson | |
| 3,494,113 A | 2/1970 | Kinney | |
| 3,676,242 A | 7/1972 | Prentice | |
| 3,695,437 A | 10/1972 | Shaltis | |
| 3,740,933 A | 6/1973 | Hollowell | |
| 3,807,150 A | 4/1974 | Maracle | |
| 3,841,953 A | 10/1974 | Kohkamp et al. | |
| 3,950,300 A * | 4/1976 | Hittmair et al. | .............. 523/109 |
| 4,353,242 A | 10/1982 | Harris et al. | |
| 4,657,959 A | 4/1987 | Bryan et al. | |
| 4,778,832 A * | 10/1988 | Futami et al. | ................ 523/109 |
| 4,965,295 A | 10/1990 | Schwabe et al. | |
| 5,064,891 A | 11/1991 | Fujiki et al. | |
| 5,145,665 A * | 9/1992 | Klueppel et al. | .............. 424/50 |
| 5,249,862 A | 10/1993 | Herold et al. | |
| 5,286,105 A | 2/1994 | Herold et al. | |
| 5,304,312 A | 4/1994 | Forster et al. | |
| 5,332,122 A | 7/1994 | Herold et al. | |
| 5,350,515 A | 9/1994 | Stark et al. | |
| 5,415,677 A | 5/1995 | Ager et al. | |
| 5,435,870 A | 7/1995 | Takagaki et al. | |
| 5,472,463 A | 12/1995 | Herman et al. | |
| 5,484,466 A | 1/1996 | Brown et al. | |
| 5,487,767 A | 1/1996 | Brown | |

(Continued)

FOREIGN PATENT DOCUMENTS

DE    34 10 646    10/1985

(Continued)

OTHER PUBLICATIONS

International Search Report.

(Continued)

*Primary Examiner*—Randy Gulakowski
*Assistant Examiner*—Robert Loewe
(74) *Attorney, Agent, or Firm*—Collard & Roe, P.C.

(57) ABSTRACT

Dental impression masses are described, which contain selected curable polymer systems and a mixture of a silicon-containing non-ionic surfactant that has at least one (poly)alkylene oxide group and a molecular mass of less than 6000 g/mol, and of a non-ionic fluorosurfactant containing at least one partially fluoridated or perfluoridated hydrocarbon group that is connected with a (poly)alkylene oxide group, a hydrocarbon group, an aliphatic polyhydroxy group, or heterocyclic group that contains nitrogen, by way of an oxygen atom, an amino group, a keto group, a carboxylic acid ester group, a phosphoric acid ester group, a carboxylic acid amide group and/or a phosphoric acid amide group, or of a non-ionic fluorosurfactant that has at least one partially fluoridated or perfluoridated hydrocarbon radical and at least one amino oxide radical. These dental impression masses flow extremely well onto the damp tooth under practical conditions, and an extremely detail-accurate impression forms during the processing time.

41 Claims, No Drawings

U.S. PATENT DOCUMENTS

| | | | |
|---|---|---|---|
| 5,494,487 | A | 2/1996 | Lee |
| 5,494,497 | A | 2/1996 | Lee |
| 5,536,290 | A | 7/1996 | Stark et al. |
| 5,543,007 | A | 8/1996 | Takagaki et al. |
| 5,547,480 | A | 8/1996 | Coulonvaux |
| 5,569,311 | A | 10/1996 | Oda et al. |
| 5,569,691 | A | 10/1996 | Guggenberger et al. |
| 5,582,146 | A | 12/1996 | Linsbauer et al. |
| 5,583,178 | A * | 12/1996 | Oxman et al. ............... 524/862 |
| 5,596,025 | A * | 1/1997 | Oxman et al. ............... 523/109 |
| 5,597,882 | A | 1/1997 | Schiller et al. |
| 5,601,717 | A | 2/1997 | Villette et al. |
| 5,611,922 | A | 3/1997 | Stene |
| 5,613,992 | A | 3/1997 | Engel |
| 5,645,718 | A | 7/1997 | Hardison et al. |
| 5,661,222 | A * | 8/1997 | Hare ......................... 525/478 |
| 5,683,660 | A | 11/1997 | Wirth et al. |
| 5,685,985 | A | 11/1997 | Brown et al. |
| 5,690,712 | A | 11/1997 | Engel |
| 5,690,911 | A * | 11/1997 | Mirajkar et al. ............... 424/49 |
| 5,714,126 | A | 2/1998 | Frund |
| 5,730,766 | A | 3/1998 | Clements |
| 5,730,768 | A | 3/1998 | Kaminaga et al. |
| 5,750,589 | A | 5/1998 | Zech et al. |
| D396,098 | S | 7/1998 | Gillingham et al. |
| D398,046 | S | 9/1998 | Gillingham et al. |
| 5,830,951 | A * | 11/1998 | Fiedler ....................... 525/478 |
| 5,852,068 | A * | 12/1998 | Jada ......................... 523/109 |
| 5,863,965 | A * | 1/1999 | Hare ......................... 523/109 |
| 5,907,002 | A | 5/1999 | Kamohara et al. |
| 5,951,729 | A | 9/1999 | Ernst et al. |
| 5,955,513 | A * | 9/1999 | Hare ......................... 523/109 |
| 5,998,561 | A * | 12/1999 | Jada ........................... 528/15 |
| 6,087,416 | A | 7/2000 | Pearlstine et al. |
| 6,103,847 | A * | 8/2000 | Lewis et al. .................... 528/21 |
| 6,113,884 | A * | 9/2000 | Mirajkar et al. ............... 424/49 |
| 6,121,362 | A * | 9/2000 | Wanek et al. ............... 524/448 |
| 6,129,244 | A | 10/2000 | Horth |
| 6,168,052 | B1 | 1/2001 | Keller |
| 6,291,546 | B1 | 9/2001 | Kamohara et al. |
| 6,348,084 | B1 | 2/2002 | Gieseke et al. |
| 6,348,085 | B1 | 2/2002 | Tokar et al. |
| 6,350,291 | B1 | 2/2002 | Gieseke et al. |
| 6,368,374 | B1 | 4/2002 | Tokar et al. |
| D461,003 | S | 7/2002 | Gieseke et al. |
| 6,455,029 | B1 | 9/2002 | Angeletakis et al. |
| 6,517,598 | B2 | 2/2003 | Anderson et al. |
| 6,552,104 | B1 * | 4/2003 | Hare ......................... 523/109 |
| 6,561,807 | B2 * | 5/2003 | Hare ......................... 433/214 |
| 6,572,667 | B1 | 6/2003 | Greif et al. |
| 6,585,792 | B2 | 7/2003 | Schneider et al. |
| 6,598,580 | B2 | 7/2003 | Baumann et al. |
| 6,610,117 | B2 | 8/2003 | Gieseke et al. |
| 6,610,126 | B2 | 8/2003 | Xu et al. |
| 6,649,146 | B2 | 11/2003 | Angeletakis et al. |
| D483,459 | S | 12/2003 | DeWit et al. |
| 6,677,393 | B1 | 1/2004 | Zech et al. |
| 6,743,317 | B2 | 6/2004 | Wydeven |
| 6,762,242 | B1 * | 7/2004 | Torto et al. .................. 524/588 |
| 6,783,565 | B2 | 8/2004 | Gieseke et al. |
| 6,818,148 | B1 * | 11/2004 | Watanabe et al. .......... 252/79.1 |
| 6,835,760 | B2 | 12/2004 | Schaub et al. |
| 6,861,457 | B2 | 3/2005 | Kamohara |
| 6,953,124 | B2 | 10/2005 | Winter et al. |
| 6,966,940 | B2 | 11/2005 | Krisko et al. |
| 6,998,427 | B2 | 2/2006 | Del Torto et al. |
| 7,004,986 | B2 | 2/2006 | Kopec et al. |
| 7,097,694 | B1 | 8/2006 | Jaroszczyk et al. |
| 7,211,124 | B2 | 5/2007 | Gieseke et al. |
| 7,255,300 | B2 | 8/2007 | Johnston |
| 7,276,545 | B2 | 10/2007 | Eckhardt et al. |
| 7,318,851 | B2 | 1/2008 | Brown et al. |
| 7,323,029 | B2 | 1/2008 | Engelland et al. |
| 7,351,270 | B2 | 4/2008 | Engelland et al. |
| 7,572,842 | B2 * | 8/2009 | Zech et al. ................... 523/109 |
| 2001/0039323 | A1 | 11/2001 | Achenbach et al. |
| 2004/0020177 | A1 | 2/2004 | Ota et al. |
| 2004/0147424 | A1 * | 7/2004 | Syldath et al. ............... 510/421 |
| 2005/0081497 | A1 | 4/2005 | Connor |
| 2007/0173557 | A1 | 7/2007 | Bublewitz et al. |
| 2007/0193236 | A1 | 8/2007 | Merritt |
| 2007/0261662 | A1 | 11/2007 | Lampert et al. |
| 2008/0011896 | A1 | 1/2008 | Johnston et al. |
| 2008/0022641 | A1 | 1/2008 | Engelland et al. |
| 2008/0060329 | A1 | 3/2008 | Brown et al. |
| 2008/0066434 | A1 | 3/2008 | Kuempel et al. |
| 2008/0086990 | A1 | 4/2008 | Kuempel et al. |
| 2008/0115470 | A1 | 5/2008 | Kuempel et al. |
| 2008/0135470 | A1 | 6/2008 | Merritt et al. |
| 2008/0250763 | A1 | 10/2008 | Widerski et al. |
| 2009/0090091 | A1 | 4/2009 | Kuempel et al. |

FOREIGN PATENT DOCUMENTS

| | | |
|---|---|---|
| DE | 40 10 281 | 10/1990 |
| DE | 41 37 698 | 5/1993 |
| DE | 43 06 997 | 9/1994 |
| DE | 199 22 929 | 11/1999 |
| DE | 100 17 154 | 11/2001 |
| DE | 699 17 384 | 6/2005 |
| DE | 602 08 371 | 6/2006 |
| EP | 0 170 219 | 2/1986 |
| EP | 0 231 420 | 8/1987 |
| EP | 0 244 478 | 11/1987 |
| EP | 0 492 413 | 7/1992 |
| EP | 0 541 972 | 5/1993 |
| EP | 0 613 926 | 9/1994 |
| EP | 0 492 412 | 3/1995 |
| EP | 0 723 807 | 7/1996 |
| EP | 0 729 341 | 9/1996 |
| EP | 0 847 745 | 6/1998 |
| EP | 0 885 932 | 12/1998 |
| EP | 0 956 908 | 11/1999 |
| EP | 0 974 626 | 1/2000 |
| EP | 1 165 016 | 1/2002 |
| EP | 1 226 808 | 7/2002 |
| EP | 1 290 998 | 3/2003 |
| EP | 1 317 917 | 6/2003 |
| EP | 1 390 424 | 2/2004 |
| FR | 2 034 160 | 12/1970 |
| JP | S58-151417 | 3/1982 |
| JP | S60-155921 | 3/1984 |
| JP | 59-170669 | 11/1984 |
| JP | 60-112320 | 7/1985 |
| JP | H02-48118 | 9/1988 |
| JP | 1-11971 | 4/1989 |
| JP | 0 171615 A | 10/1989 |
| JP | 97/40917 | 11/1997 |
| JP | 63-122617 | 6/1998 |
| JP | H02-48117 | 9/1998 |
| WO | 88/03432 | 5/1988 |
| WO | WO 88/03431 | 5/1988 |
| WO | 97/40908 | 11/1997 |
| WO | 97/40910 | 11/1997 |
| WO | WO 97/40918 | 11/1997 |
| WO | WO 97/41939 | 11/1997 |
| WO | WO 98/44860 | 10/1998 |
| WO | WO 99/47237 | 9/1999 |
| WO | WO 00/48553 | 8/2000 |
| WO | WO 00/50149 | 8/2000 |
| WO | WO 00/74818 | 12/2000 |
| WO | WO 02/32338 | 4/2002 |
| WO | 02/49741 A1 | 6/2002 |
| WO | WO 02/102326 | 12/2002 |

| WO | WO 03/095068 | 11/2003 |
| WO | WO 2004/020075 A2 | 3/2004 |
| WO | WO 2004/058196 | 7/2004 |
| WO | WO 2005/016289 | 2/2005 |
| WO | WO 2005/077321 | 8/2005 |

OTHER PUBLICATIONS

Barry K. Norling et al.: "Surface Wettability Modification of Poly (vinyl siloxanes) with Nonionic Surfactants", *Colloids and Surfaces*, Jun. 17, 1986, vol. 20, pp. 277-288. XP-002451249 (ISR).

3M Material Safety Data Sheet, edition Aug. 30, 2002, pp. 1-9. (Spec, p. 8).

Rupp et al., "Quantifizierung der Benetzungs-eigenschaften . . . ," *Deutsche Zahnärztliche Zeitschrift* [German Dental Journal] 60 (2005) 10, p. 587-592. (Spec, p. 11).

Schriftenreihe Pigmente Degussa Kieselsaeren [monograph series on pigments, Degussa silicic acids], "Technical Bulletin Pigments," No. 12, p. 5, and No. 13, p. 3, Aug. 1986. (Spec, p. 81).

Ullmanns Encyklopaedie der Technischen Chemie [Ullmann's Encyclopedia of Technical Chemistry], vol. 21, Germany 1982, p. 523. (Spec, p. 82).

U.S. Appl. No. 09/258,481, filed Feb. 26, 1999.

U.S. Appl. No. 09/502,346, filed Feb. 10, 2000.

U.S. Appl. No. 10/055,062, filed Jan. 22, 2002.

U.S. Appl. No. 10/914,510, filed Aug. 9, 2004.

U.S. Appl. No. 11/999,246, filed Dec. 3, 2007.

\* cited by examiner

DENTAL IMPRESSION MASSES, HARDENED PRODUCTS PRODUCED FROM THEM, AND USE OF SURFACTANTS FOR THE PRODUCTION OF DENTAL IMPRESSION MASSES

CROSS REFERENCE TO RELATED APPLICATIONS

This application is the National Stage of PCT/EP2007/000066 filed on Jan. 5, 2007, which claims priority under 35 U.S.C. §119 of German Application No. 10 2006 001 126.0 filed on Jan. 9, 2006. The international application under PCT article 21(2) was not published in English.

New dental impression masses that are characterized by improved wetting behavior are described.

Dental impression masses as such are known and have already been in use for a long time. These masses must demonstrate a plurality of properties, such as rapid binding behavior, excellent detail accuracy, and, at the same time, good storage ability of the pre-products. Usually, two-component mixtures are used, which are mixed with one another directly before use, and which must then be processed rapidly. In order to achieve the best possible detail accuracy, it is important that there is as little fluid, such as saliva or blood, between the tooth or gum and the impression that is forming, on the one hand, and that this fluid is incorporated as little as possible into the form body that is forming, on the other hand.

Dental impression masses usually contain hydrophobic materials such as polyorganosiloxanes. To minimize the fluid layer between impression and tooth or gum, the use of surfactants in dental impression masses has already been proposed. These bring about a distribution of the water film, and therefore the formation of a fluid film is made more difficult.

A silicone composition that can be cured and used as a dental impression material is known from U.S. Pat. No. 4,657,959, and contains a curable silicone prepolymer and a surfactant. The surfactant to be used is preferably an ethoxylated non-ionic surfactant agent, containing one or more siloxane or perfluoroalkyl groups. The surfactant is used in an amount so that the composition particularly preferably has a contact angle of less than 10° three minutes after application of the water droplet onto the hardened composition. However, these contact angle properties of an impression material that has already hardened after three minutes do not correspond to requirements in practice. Furthermore, in the examples of this U.S. Pat. No. 4,657,959, amphoteric or ionic fluorosurfactants are listed, and, in the case of the non-ionic fluorosurfactants, the perfluoroalkyl groups are linked with the polyether groups by way of an SCUM group. These $SO_2NR$ groups are unsuitable for use in a platinum-catalyzed addition-crosslinking silicone, since they form strong metal-chelate complexes on the platinum catalyst, and inhibit the catalyst in this manner. Furthermore, neither the addition of a non-reactive polyether polymer nor of a reactive polyether polymer that can be polymerized in, for example with vinyl, allyl, or SiH groups, is disclosed in U.S. Pat. No. 4,657,959.

An addition-crosslinking silicone impression mass composition is described in EP-A-1,290,998, which contains an organopolysiloxane having at least two aliphatically saturated hydrocarbon groups, a polyether having at least one alkyl group, an organohydrogen siloxane, a soluble platinum catalyst, an inorganic filler, as well as a non-ionic surfactant and/or a polyether-modified silicone oil.

EP-A-847,745 describes dental silicone impression materials that contain not only silicone polymers with SiH groups and silicon polymers with Si-alkenyl groups, catalyst, and inorganic fillers, but also a polysiloxane polyester polymer having at least one polyalkylene oxide substituent based on dimethicone and having a fluoridated alkyl substituent. According to this disclosure, a contact angle of less than 73° is determined by way of the Wilhelmi method with a cured, solid sample body. The fluoride-containing polysiloxane polyester that is used is a polymer having a high molecular weight, at the chain ends of which fluoridated hydrocarbons are sitting, in each instance. The contact angles that can be achieved with this are rather slight. The fluoridated polysiloxane polyester, because of its polymer structure, the high mole mass of the polymers, and the fluorocarbon groups sitting at the two chain ends, does not represent a traditional surfactant having a low molecular weight, with a hydrophilic head and a hydrophobic tail.

WO-A-2004/058,196 describes dental impression materials comprising a polyvinyl siloxane and a surfactant, whereby the surfactant imparts such wettability to the composition that the material has a surface contact angle with water of less than approximately 10° after approximately 15 seconds, 15 minutes after it hardens. In particular these contact angles are achieved by means of using the surfactant PEG8 methicone.

EP-A-1,165,016 describes an addition-crosslinking impression material on the basis of silicone, with a polyalkylene oxide and/or its derivates, having a mole mass >3000 g/mol with a concentration between 0.001 to 1.0 wt.-%. The polyether that is used is supposed to improve the strength of the impression material. At the same time, the contact angles were determined at >80°. From this reference, it is evident that by adding only polyether, it is not possible to achieve good contact angles and therefore good hydrophilia properties.

EP-A-729,341 discloses the use of polyether carbosilanes for the hydrophilization of dental impression masses. The contact angle/edge angle measurement takes place 30 minutes after hardening of the impression material, and the contact angles lie at minimally 42°.

EP-A-613,926 describes polyether impression materials that contain at least one hydrophilic agent from the group consisting of hydrophilic silicone oils, fluoridated hydrocarbons, block copolymers of ethylene oxide/propylene oxide, fatty alcohol derivatives, alkyl phenol derivatives, fatty amines, amino oxides, fatty acid glycol and glycerin derivatives, fatty acids and fatty acid monoesters. The contact angle measurement takes place 30 minutes after hardening of the impression material, and the contact angles lie between 18 and 65°.

An addition-crosslinking silicone impression material composition is known from WO-A-00/48,553, which contains a silicone polyether that can be polymerized in, having comb-like polyether groups. In the examples, combinations of this silicone polyether that can be polymerized in with nonyl phenyl ethoxylate surfactants were described.

EP-A-231,420 discloses an addition-crosslinking silicone impression material with a silicone polyether.

DE-A-4,010,281 discloses addition-crosslinking polyether impression compositions in which the polyether contains vinyl dimethyl siloxy groups or allyl groups in the end position. The unsaturated groups that are bound to the polyether by way of an SiOC bond are susceptible to hydrolysis and not stable during storage. In the other case, the polyethers are linked with vinyl dimethyl siloxane groups by means of Pt-catalyzed hydrosilylation. The highly active catalyst cannot be separated by means of conventional constant purification methods. Even purification of the polymer by way of high-vacuum distillation is not possible, because of the high mole masses of the polymer and of the Pt-catalyst. The polyether polymers synthesized in this manner and contaminated with residual platinum are not stable during storage and thus are not suitable for a dental impression mass composition. For this reason, no commercialization of these products has taken place up to the present date.

U.S. Pat. No. 5,064,891 describes an addition-crosslinking silicone composition with a silicone surfactant. The contact angle measurements were carried out on hardened sample bodies and three minutes after application of the water droplets. The contact angles described lie between 60 and 65°.

EP-885,932 describes addition-crosslinking organopolysiloxane compositions with a hydrophilic unsaturated polysiloxane-polyether copolymer with 2 to 5 silicon atoms and at least one aliphatic unsaturated functionality and at least one polyether functionality.

In U.S. Pat. No. 5,907,002, an addition-crosslinking impression silicone material is described, which is formulated in the combination of a non-ionic surfactant with a methyl phenyl polysiloxane. The non-ionic surfactant can have a lipophilic group in addition to the hydrophilic group, whereby the former can be an alkyl group or a fluorocarbon group. The use of mixtures of silicone surfactant with fluorosurfactant is not disclosed. The contact angles that are achieved lie between 28 and 60°.

Combinations of fluorosurfactants and silicone surfactants are known from DE 699 17 384 T2 (corresponding to EP-B-974,626). This document describes aqueous pigmented inkjet printer inks containing such surfactant mixtures.

Finally, curable dental impression materials containing surfactants or combinations of surfactants are known from DE-A-199 22 929. These impression materials are intended for taking impressions of the oral mucous membranes, and flow at very slight pressure; however, they do not flow if no pressure is applied. The impression material is supposed to exert only very slight irritation on the oral mucous membrane. The use of mixtures of silicone surfactants and fluorosurfactants is not disclosed.

U.S. Pat. No. 6,861,457 describes hydrophilic dental impression materials on the basis of addition-crosslinking polysiloxanes. These contain not only a polyether with unsaturated groups but also a non-ionic surfactant and/or a polyether-modified silicone oil. Combinations of fluorosurfactants with silicone surfactants are not described.

Hydrophilic polyethers are disclosed in DE-A-43 06 997. These can contain the most varied surfactants; possible substance classes that are disclosed are hydrophilic silicone oils or fluoridated hydrocarbon compounds, along with other surfactants. In the examples, curable compositions containing polyethers capped with aziridino groups and a non-ionic fluorosurfactant (Fluorad FC430) are described. This compound contains perfluoro-octyl sulfonate groups, according to the 3M Material Safety Data Sheet, edition 30.08.2002. Curable compositions containing mixtures of silicone surfactants and fluorosurfactants with (poly)alkylene oxide groups, hydrocarbon groups, or aliphatic polyhydroxy groups are not disclosed in DE-A-43 06 997.

EP-B-244,478 describes the use of hydrophilic silicones as dental impression materials. In this document, the use of wetting agents composed of ethoxylated non-ionic surfactant substances having solubilizing siloxane or perfluoroalkyl groups is disclosed, among other things. Curable compositions containing mixtures of silicone surfactants and fluorosurfactants with (poly)alkylene oxide groups, hydrocarbon groups, or aliphatic polyhydroxy groups are not disclosed in this document, either.

WO-A-2005/016289 describes dental impression masses on the basis of polyorganosiloxanes. These are characterized by the presence of a wetting agent that improves the wettability of the mass by water, so that a contact angle of less than 50° occurs after three minutes. Ethoxylated nonyl phenols or PEG-8 methicone, for example, are proposed as wetting agents.

In the cited patent documents, the contact angle measurements are not carried out with reference to practical requirements, i.e. the contact angles are measured using hardened sample bodies. However, the practical requirement is that for one thing, it is not the contact angle properties of the cured impression material that are relevant, but just the opposite, the contact angle properties in the non-cured, plastic state are decisive, and for another thing, the contact angle properties are relevant not only after a time span of three minutes, but rather immediately while taking the impression, i.e. between greater than 0 seconds and less than 10 seconds after the initial contact between the plastic impression material and the tooth substance or the oral mucous membrane. This is explained by the fact that when an impression is taken, during the processing time, the impression material must wet the tooth substance and oral mucous membrane, which is damp and wetted with saliva, initially, during the plastic phase, in other words in the non-cured state, i.e. between >0 and <10 s, and must flow onto it immediately. Any contact angle properties that occur afterwards are therefore no longer relevant for taking an impression that is true to details.

In the phase that is important under practical conditions, for flow of the impression material onto the damp tooth, after the two components are mixed, during the so-called processing time, during which the impression material is still plastically deformable and comes into contact with damp teeth, saliva, and blood, the materials disclosed in the prior art described above do not have a good contact angle of <=10°. Spreading of the water droplet on the material surface is not observed. The contact angles described in these documents are relevant only when casting liquid plaster paste into the hardened impression outside of the mouth, to produce the model, but not for the decisive impression-taking phase in the mouth. Furthermore, none of these documents describes the use of a synergistically acting surfactant mixture or a combination of this mixture with a polyether.

A very up-to-date and scientific study in *Deutsche Zahnärztliche Zeitschrift [German Dental Journal]* 60 (2005) 10, p. 587-592, by Rupp et al., describes the demands that are made on a dental impression material with regard to wetting behavior.

Here, studies concerning initial hydrophilia and equilibrium hydrophilia were carried out. As a practical requirement, it results from this that at every point in time during the plastic phase of the processing time, the impression material is supposed to have a low initial hydrophilia and, in addition, an equally low equilibrium hydrophilia at every point in time.

Application and flow of the impression material in the patient's mouth takes place at different points in time, under practical conditions, depending on the impression technique and the number of teeth of which an impression is to be taken. Thus, for example, in the case of a single crown impression, a relatively short period of time is required for application and flow, e.g. 40 seconds, while in the case of more comprehensive inlets with 4 or 5 teeth of which an impression is to be taken, application and flow have taken place only after two minutes.

According to the study by Rupp et al., the impression materials used today, particularly the silicone impression materials, demonstrate a strong drift in the hydrophobic direction with an increasing processing time, and this runs counter to the aforementioned practical needs and practical requirements for the impression material.

Furthermore, the initial hydrophilia contact angles measured there also require improvement, both in the case of polyether impression materials and silicone impression materials.

Proceeding from this state of the art, it was the task of the present invention to make available a dental impression mass that provides a low initial contact angle and a constant and low equilibrium contact angle (hydrophilia) at every point in time during the processing time (both at the beginning and at the end), so that under practical conditions, extremely good flow onto the damp tooth or tooth tissue takes place, and this in turn leads to the formation of an impression that is extremely true to details.

It was surprisingly found that the use of a synergistic mixture of select surfactants leads to initial spreading of the water film between tooth or gums and the impression mass that is still plastic, and that in this way, it is possible to produce impressions that are very true to details.

The present invention relates to a dental impression mass containing curable polymers selected from the group of organopolysiloxanes that crosslink by means of an addition reaction, of organopolysiloxanes that crosslink by means of a condensation reaction, of polyethers that crosslink by means of a condensation reaction and contain alkoxy silyl groups, of polyethers that crosslink by means of an addition reaction and contain aziridino groups, of polyethers that crosslink by means of an addition reaction and contain alkenyl groups, of polyethers that crosslink by means of a radical polymerization reaction and contain ester groups of an ethylene-unsaturated carboxylic acid, or of polyethers, silicones, or rubbers that crosslink by means of ring-opening metathesis reaction, and furthermore containing at least one (poly)alkylene oxide groups as well as a non-ionic surfactant containing a group that contains silicon, having a mole mass of less than 6000 g/mol (also called silicon-containing surfactant below), and a non-ionic fluorosurfactant that has at least one partially fluoridated or perfluoridated hydrocarbon group that is connected, by way of an oxygen atom, an amino group, a keto group, a carboxylic acid ester group, a phosphoric acid ester group, a carboxylic acid amide group and/or a phosphoric acid amide group, with a (poly)alkylene oxide group, a hydrocarbon group, an aliphatic polyhydroxy group, or a heterocyclic group containing nitrogen, or that has at least one partially fluoridated or perfluoridated hydrocarbon group and at least one amino oxide group (also called fluorosurfactant below).

Preferred dental impression masses, 40 seconds after the start of mixing, preferably at every point in time during the processing time between >0 and 3 minutes (measured at 50% relative humidity in the climate-controlled chamber), have a low initial water droplet contact angle of <10°, measured at a droplet age of 10 seconds.

The dynamic progression of the water droplet contact angle of preferred dental impression masses, measured 40 seconds after the start of mixing, preferably assumes the following values: after a droplet age of 0.25 seconds, a water droplet contact angle of <75°, preferably of <40°; after a droplet age of 0.5 seconds, a water droplet contact angle of <55°, preferably <30°; after a droplet age of 1 second, a water droplet contact angle of <35°, preferably <25°; after a droplet age of 2 seconds: a water droplet contact angle of <20°; and after a droplet age of 3 seconds, a water droplet contact angle of <10°.

A water droplet spreads on the dental impression mass according to the invention that has not cured yet, and after a short time, typically after 3 seconds, at the latest, it forms a droplet having a very slight contact angle of <10°, or it runs out completely, forming a water film.

The dental impression masses according to the invention are characterized by the content of a synergistic mixture of select surfactants.

Within the framework of this description, the term (poly) alkylene oxide groups is understood to mean groups that have at least one alkylene oxide unit, preferably multiple alkylene oxide units, whereby the alkylene groups in a group can have different numbers of carbon atoms. These different alkylene groups can occur in the group statistically or in the form of blocks of recurring structural units.

Within the framework of this description, the term hydrocarbon group is understood to mean groups that contain at least one polyhydroxy aldehyde or polyhydroxy ketone unit, and which have the gross formula $C_aH_{2a}O_a$ (a=whole number between 5 and 7). In general, these are monosaccharides or oligosaccharides having two to ten polyhydroxy aldehyde or polyhydroxy ketone units.

Preferred hydrocarbon groups are composed of five-member or six-member rings. Preferred hydrocarbon groups are derived from monosaccharides, particularly from ribose, xylose, arabinose, glucose, mannose, galactose, fructose, sorbose, fucose and rhamnose. Other preferred hydrocarbon groups are derived from disaccharides, particularly from saccharose, lactose and maltose.

Within the framework of this description, the term aliphatic polyhydroxy group is understood to mean aliphatic groups having at least two, preferably two to six hydroxyl groups. Aliphatic groups having four to ten carbon atoms, which are substituted with two to six hydroxyl groups, are preferred.

Within the framework of this description, the term heterocyclic group containing nitrogen is understood to mean five-member or six-member aromatic or, in particular, non-aromatic groups that contain at least one nitrogen atom and, in particular, also oxygen as an additional ring atom. Preferably, a morpholine group that is bound to the bridge group by way of the nitrogen atom is used.

The fluorosurfactants used according to the invention contain at least one bridge group for connecting the perfluoro hydrocarbon group or partially fluoro hydrocarbon group and the hydrophilic (poly)alkylene oxide, hydrocarbon, or aliphatic polyhydroxy group or the heterocyclic group containing nitrogen, or these fluorosurfactants have at least one partially fluoridated or perfluoridated hydrocarbon group and at least one amino oxide group.

The fluorosurfactants must be selected as a function of the crosslinkable system. In the organopolysiloxanes that crosslink by means of an addition reaction or the polyethers that crosslink by means of an addition reaction and contain alkenyl groups, fluorosurfactants intervene in the hardening reaction with sulfur, nitrogen and/or phosphorus atoms, in disadvantageous manner, so that in these systems, fluorosurfactants containing sulfur, nitrogen and/or phosphorus atoms are preferably excluded.

In the other curable systems, fluorosurfactants with nitrogen and/or phosphorus atoms, i.e. groups containing these atoms, can be used in addition. Examples of this are amino groups, phosphoric acid or phosphonic acid ester groups; or carboxylic acid, phosphoric acid or phosphonic acid amide groups. Also, fluorosurfactants that have several of these groups or atoms can be used, for example amino acid and carboxylic acid amide groups.

Non-ionic fluorosurfactants that have at least one (poly) alkylene oxide group and/or at least one hydrocarbon group, and that contain at least one partially fluoridated or perfluoridated hydrocarbon group that is connected with the (poly) alkylene oxide group or the hydrocarbon group by way of an oxygen atom or a carboxylic acid ester group, are preferred.

Particularly preferably, fluorosurfactants are used that have a partially fluoridated or perfluoridated alkyl group that is bound to an ethylene oxide group or a monosaccharide or disaccharide group by way of an oxygen atom.

Very particularly preferred fluorosurfactants are compounds having the Formula I

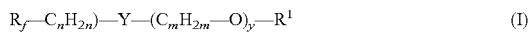

where $R_f$ is a group having the formula $C_xF_{2x+1}$, x stands for a whole number from 1 to 30, n is a whole number from 0 to 30, Y is $-NR^1-$, $-(O-)_2P(O)(OR^1)$, $-(NR^1-)_2P(O)(OR^1)$, $-(NR^1)P(O)(OR^1)(O)-$, $-CO-$ or, very particularly preferably, $-O-$ or $-CO-O-$, m stands for a whole number from 2 to 6, y is a whole number from 1 to 60, and $R^1$ is hydrogen or a monovalent organic group such as alkyl, alkenyl, cycloalkyl, aryl, aralkyl or a heterocyclic aromatic group, whereby m and $R^1$, within a molecule, can assume different meanings within the framework of the given definition.

Different indices m mean that alkylene oxide units having a different number of carbons can be present, which can occur in a statistical distribution or in the form of blocks.

$R^1$ is preferably hydrogen, $C_1$-$C_6$ alkyl or phenyl.

Preferably used compounds having the Formula I are those in which x stands for a whole number from 1 to 18, n is a whole number from 1 to 3, Y is $-O-$, m stands for 2 or 3, particularly 2, y is a whole number from 1 to 30, and $R^1$ is hydrogen or an alkyl group.

Very particularly preferred fluorosurfactants are compounds having the Formulas Ia and Ib

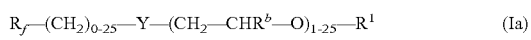

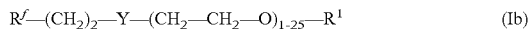

where $R_f$ possesses the meaning defined above, preferably stands for a group having the formula $C_xF_{2x+1}$ with x=1 to 18, particularly x=2 to 12, Y possesses the meaning defined above, preferably is $-O-$, $R^b$ is $C_1$-$C_6$ alkyl, preferably methyl or ethyl, and $R^1$ possesses the meaning defined above, preferably is hydrogen, $C_1$-$C_6$ alkyl, particularly methyl, $C_2$-$C_6$ alkenyl, preferably vinyl, or phenyl.

Fluorosurfactants used according to the invention preferably have molecular weights of less than 4000 g/mol, particularly preferably from 180 to 2500 g/mol.

Examples of very particularly preferred fluorosurfactants are the following compounds having the Formulas Ic and Id

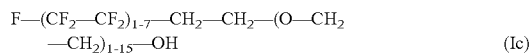

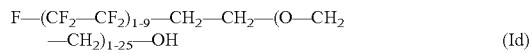

Particularly preferably, fluorosurfactants are used that are biodegradable and that do not have any findings or acceptable findings according to ISO 10993-1 when used in dental molding masses.

Examples of preferably used fluorosurfactants are the substances or substance classes listed below:

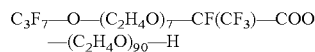

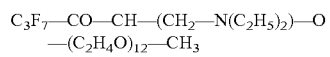

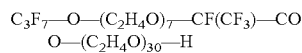

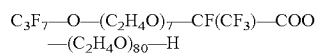

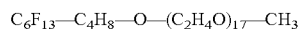

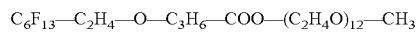

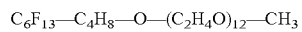

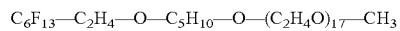

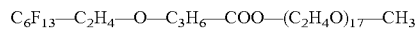

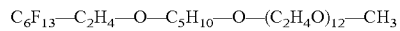

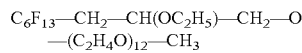

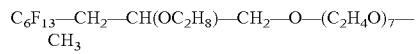

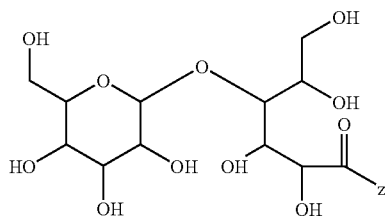

with $z=-(NH-CH_2-CO)_p-NH-CH((CH_2)_2-R_f)(CH_2)_8-R)$ or $z=-NH-(CH_2)_4-CH((NH-CO-(CH_2)_2-C_8F_{17})(CO-NH-(CH_2)_9-CH_3)$, with p=1 or 2 and R=$-CH_3$, $-CH=CH_2$ and $R_f=-C_6F_{13}$ or $-C_8F_{17}$, preferably a compound derived from lactose;

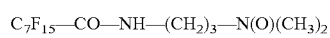

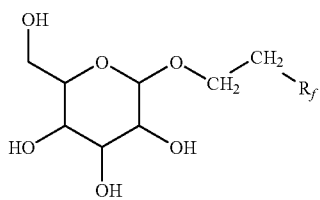

with $R_f$=—$C_6F_{13}$ or —$C_8F_{17}$,
preferably a compound derived from galactose;

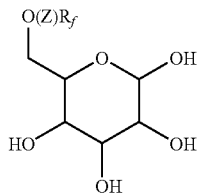

with
$Z$=(CH$_2$)—CH=CH$_2$ and $R_f$=—$C_4F_9$, —$C_6F_{13}$ or —$C_8F_{17}$
or
$Z$=—CO—(CH$_2$)$_n$—, n=2 and $R_f$=—$C_8F_{17}$ or
$Z$=—CO—(CH$_2$)$_n$—, n=10 and $R_f$=—$C_4F_9$ or —$C_6F_{13}$,
preferably a compound derived from galactose;

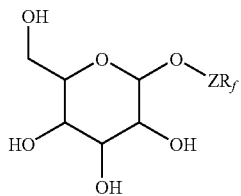

with
$Z$=(CH$_2$)$_2$ and $R_f$=—$C_6F_{13}$ or —$C_8F_{17}$ or
$Z$=—(CH$_2$)$_2$—CH=CH$_2$ and $R_f$=—$C_6F_{13}$ or —$C_8F_{17}$
preferably a compound derived from glucose;

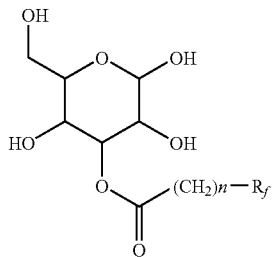

with
n=2 and $R_f$=—$C_8F_{17}$ or
n=10 and $R_f$=—$C_4F_9$ or —$C_6F_{13}$, preferably a compound derived from glucose;

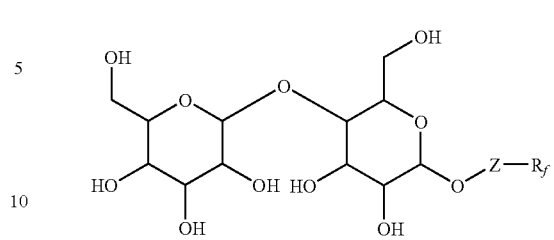

with
$Z$=(CH$_2$)$_2$ and $R_f$=—$C_6F_{13}$ or —$C_8F_{17}$ or
$Z$=—(CH$_2$)$_n$—CH=CH$_2$, n=3 and $R_f$=—$C_6F_{13}$ or
$Z$=—(CH$_2$)$_n$—CH=CH$_2$, n=9 and $R_f$=—$C_6F_{13}$ or —$C_8F_{17}$,
preferably a compound derived from maltose;

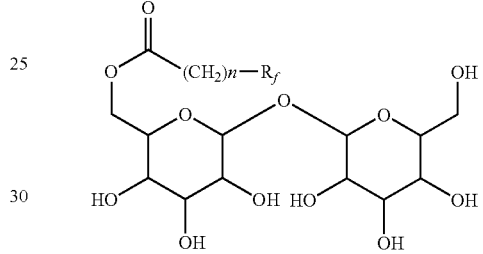

with
n=2 and $R_f$=—$C_8F_{17}$ or
n=4 and $R_f$=—$C_6F_{13}$ or —$C_8F_{17}$,
n=10 and $R_f$=—$C_4F_9$ or —$C_6F_{13}$,
preferably a compound derived from trehalose;

$R_f$—(CH$_2$)$_n$—OP(O)—(O—(C$_2$H$_4$O)$_p$CH$_3$)$_2$ with
n=2, p=2, 7 and $R_f$=—$C_8F_{17}$ or
n=5, p=7, 16 and $R_f$=—$C_8F_{17}$;

$R_f$—(CH$_2$)$_n$—OP(O)—(N-morpholino)$_2$ with
n=1 and $R_f$=—$C_7F_{15}$ or —$C_9F_{19}$ or
n=2 and $R_f$=—$C_4F_9$, —$C_6F_{13}$, —$C_8F_{17}$ or —$C_{10}F_{21}$ or
n=5 and $R_f$=—$C_8F_{17}$ or
n=11 and $R_f$=—$C_6F_{13}$ or —$C_8F_{17}$;

($R_f$—(CH$_2$)$_n$—O)$_2$P(O)—(N-morpholine)

with
n=1 and $R_f$=—$C_9F_{19}$ or
n=2 and $R_f$=—$C_6F_{13}$ or —$C_8F_{17}$;

$C_{10}H_{21}$—(CF$_2$)$_{11}$—O—P(O)—(N-morpholine)$_2$ $R_f$—X—O—CH$_2$—CH(OH)—CH(OH)—CH(OH)—
CH$_2$—OH with X=CH=CH—CH$_2$ and R$_f$=—C$_4$F$_9$, —C$_6$F$_{13}$ or —C$_8$F$_{17}$ or X=(CH$_2$)$_n$—CO, n=2 and R$_f$=—C$_5$F$_{11}$ or —C$_8$F$_{17}$ or X=(CH$_2$)$_n$—CO, n=10 and R$_f$=—C$_4$F$_9$ or —C$_6$F$_{13}$;

CF$_3$—(CF$_2$)$_3$—CH$_2$—O—(C$_2$H$_4$O)$_4$CH$_3$

CF$_3$—(CF$_2$)$_3$—(CH$_2$)$_3$—N((C$_2$H$_4$O)$_2$H)$_2$

CH$_3$—(C$_2$H$_4$O)$_3$—O—CH$_2$—(CF$_2$)$_{13}$—CH$_2$—O—(C$_2$H$_4$O)$_9$CH$_3$

CF$_3$—(CF$_2$)$_6$—(CH$_2$)$_2$—O—(C$_2$H$_4$O)$_m$H with m=2 to 10;

C$_6$F$_{13}$—(CH$_2$)$_2$-1-maltoside

C$_8$F$_{17}$—(CH$_2$)$_2$-1-maltoside

C$_6$F$_{13}$—CH=CH—(CH$_2$)$_3$-1-maltoside

C$_6$F$_{13}$—CH=CH—(CH$_2$)$_9$-1-maltoside

C$_6$F$_{13}$—(CH$_2$)$_4$—CO-6-trehalose

C$_6$F$_{17}$—(CH$_2$)$_2$—CO-6-trehalose

C$_8$F$_{17}$—(CH$_2$)$_4$—CO-6-trehalose

C$_4$F$_9$—(CH$_2$)$_{10}$—CO-6-trehalose

C$_4$F$_9$—(CH$_2$)$_{10}$—CO-6-sucrose

C$_6$F$_{13}$—(CH$_2$)$_{10}$—CO-6-sucrose

C$_4$F$_9$—CH=CH—CH$_2$-galactose

C$_6$F$_{13}$—CH=CH—CH$_2$-galactose

C$_4$F$_9$—CH=CH—CH$_2$-1-xylitol

C$_6$F$_{13}$—CH=CH—CH$_2$-1-xylitol

C$_8$F$_{17}$—CH=CH—CH$_2$-1-xylitol

The silicon-containing surfactant used according to the invention contains at least one (poly)alkylene oxide group and possesses a molecular mass of less than 6000 g/mol, preferably of less than 4000 g/mol, particularly from 350 to 2000 g/mol.

The silicon-containing surfactant used according to the invention contains, aside from the at least one (poly)alkylene oxide group, at least one group that contains organosiloxane groups or organosilane groups. The organic groups are hydrocarbon groups that are partially fluoridated or perfluoridated, if necessary.

Such organosiloxane surfactants or organocarbosilane surfactants are actually known.

Preferably, silicon-containing surfactants are used that are organosiloxane surfactants having the Formulas II or III, or that are organocarbosilane surfactants having the Formulas IV, V or VI $$R^4-[SiR^2R^3-O-]_a\overset{[O-SiR^5R^6]_b-R^7}{\underset{[O-SiR^8R^9]_c-R^{10}}{Si}}-(C_dJ_{2d})_e-(O-C_fH_{2f})_g-(O-C_hH_{2h})_i-O-R^{11}, \quad (II)$$

$$R^4-[R^2R^3Si-O]_u-[SiR^5-O-]_v[-SiR^6R^7-O]_w-SiR^8R^9R^{10} \atop (C_dJ_{2d})_e-(O-C_fH_{2f})_g-(O-C_hH_{2h})_i-O-R^{11}, \quad (III)$$

$$R^{11}-A1-(A2)_p-A5-\overset{A3_j-(SiR^{12}R^{13})_k-R^{14}}{\underset{A4_r-(SiR^{15}R^{16})_g-R^{17}}{(C_fH_{2f}-O)_g-(C_hH_{2h}-O)_i-R^{18}}}, \quad (IV)$$

$$R^{19}-O-(C_hH_{2h}-O)_i-(C_fH_{2f}-O)_g-(C_dJ_{2d})_c-\overset{SiR^{20}R^{21}}{\underset{BG}{|}} \quad (V)$$

$$R^{24}-O-(C_hH_{2h}-O)_i-(C_fH_{2f}-O)_g-(C_dJ_{2d})_e-SiR^{22}R^{23},$$

$$R^{19}-O-(C_hH_{2h}-O)_i-(C_fH_{2f}-O)_g-(C_dJ_{2d})_c-SiR^{20}R^{21}R^{22}, \quad (VI)$$

where $R^2$, $R^3$, $R^4$, $R^5$, $R^6$, $R^7$, $R^8$, $R^9$ and $R^{10}$, independent of one another, stand for hydrogen, alkyl, alkyloxy, alkenyl, alkenyloxy, alkynyl, alkynyloxy, aryl, aryloxy, aralkyl, aralkyloxy, alkylaryl and/or alkylaryloxy, which are partially or completely fluoridated, if necessary, preferably alkyl or alkenyl and, in particular, $C_1$-$C_6$-alkyl, a, b, c and w, independent of one another, stand for whole numbers from 0 to 100, preferably 0 to 75, particularly 0 to 35, and very particularly preferably 0 to 15, v stands for a whole number from 1 to 100, preferably 1 to 15 and very particularly preferably 1 to 6, whereby the sum of a, b and c amounts to between 1 and 300, preferably 1 to 50, particularly 1 to 10, and very particularly preferably 1 to 3, and the sum of v and w amounts to between 1 and 200, preferably 2 to 90, u is 0 or 1, d is a whole number from 1 to 10, preferably 1 to 6, and particularly 1 to 3, J stands for hydrogen or fluorine, preferably hydrogen, e is 0 or 1, f and h, independent of one another, stand for whole numbers from 2 to 6, g and i, independent of one another, are whole numbers from 0 to 30, preferably 0 to 15, whereby the sum of g and i stands for 1 to 60, preferably 2 to 30, particularly 2 to 15, $R^{11}$ is hydrogen, alkyl, alkenyl or aryl, which is partially or completely fluoridated, if necessary, preferably hydrogen or methyl, $R^{12}$, $R^{13}$, $R^{14}$, $R^{15}$, $R^{16}$ and $R^{17}$, independent of one another, stand for hydrogen, alkyl, alkyloxy, alkenyl, alkenyloxy, alkynyl, alkynyloxy, aryl, aryloxy, aralkyl, aralkyloxy, alkylaryl and/or alkylaryloxy, which are partially or completely fluoridated, if necessary, preferably alkyl or alkenyl and, in particular, $C_1$-$C_6$-alkyl, k and q, independent of one another, stand for 0 or 1, A1 stands for carbon or silicon, A2, A3 and A4, independent of one another, is a group $C_dJ_{2d}$, where J and d have the meanings defined above, j, p and l, independent of one another, are 0 or 1, A5 stands for a bivalent bridge group, particularly —O—, —CO—O— or —CO—, $R^{18}$ is hydrogen, alkyl, alkenyl or aryl, which is completely or partially fluoridated, if necessary, preferably hydrogen or methyl, $R^{20}$, $R^{21}$, $R^{22}$ and $R^{23}$, independent of one another, stand for hydrogen, alkyl, alkyloxy, alkenyl, alkenyloxy, alkynyl, alkynyloxy, aryl, aryloxy, aralkyl, aralkyloxy, alkylaryl and/or alkylaryloxy, which are partially or completely fluoridated, if necessary, preferably alkyl or alkenyl and particularly $C_1$-$C_6$-alkyl, BG is a bivalent bridge group, and $R^{19}$ and $R^{24}$, independent of one another, are hydrogen, alkyl, alkenyl or aryl, which are partially or completely fluoridated, if necessary, preferably hydrogen or methyl, with the proviso that of the groups $R^2$, $R^3$ and $R^4$ and/or the groups $R^5$, $R^6$ and $R^7$ and/or the groups $R^8$, $R^9$ and $R^{10}$ and/or the groups $R^{15}$, $R^{16}$ and $R^{17}$ and/or the groups $R^{20}$ and $R^{21}$ and/or the groups $R^{22}$ and $R^{23}$ and/or the groups $R^{20}$, $R^{21}$ and $R^{22}$ only one can be hydrogen, whereby f and h can assume different values within a molecule, within the framework of the given definition.

Different indices f and h mean that alkylene oxide units having different carbon numbers can be present, which can occur in a statistical distribution or in the form of blocks.

Particularly preferably, organosiloxane surfactants having the Formula IIIa are used

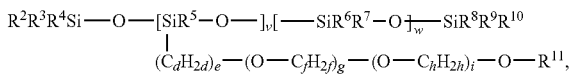
(IIIa)

where $R^2$, $R^3$, $R^4$, $R^5$, $R^6$, $R^7$, $R^8$, $R^9$ and $R^{10}$, independent of one another, stand for hydrogen, alkyl, alkyloxy, alkenyl, alkenyloxy, alkynyl, alkynyloxy, aryl, aryloxy, aralkyl, aralkyloxy, alkylaryl and/or alkylaryloxy, preferably hydrogen, alkyl, alkyloxy or alkenyl, v stands for a whole number from 1 to 100, w stands for a whole number from 0 to 100, d is a whole number from 1 to 10, e is 0 or 1, f and h, independent of one another, stand for whole numbers from 2 to 6, g and i, independent of one another, are whole numbers from 0 to 30, whereby the sum of g and i stands for 1 to 60, and $R^{11}$ is hydrogen, alkyl, alkenyl or aryl.

Other particularly preferred organosiloxane surfactants are compounds having the Formula IIIb or IIIc

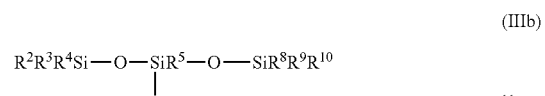
(IIIb)

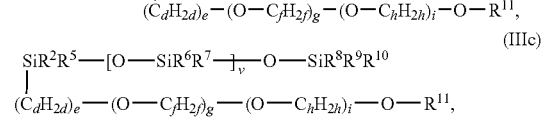
(IIIc)

where $R^2$, $R^3$, $R^4$, $R^5$, $R^6$, $R^7$, $R^8$, $R^9$ and $R^{10}$, independent of one another, are hydrogen, alkyl or alkenyl, preferably hydrogen, methyl, particularly butyloxy and methoxy, vinyl or allyl, v is a whole number from 1 to 100, d, e, f, g, h and i possess the meanings defined above, and $R^{11}$ is hydrogen, alkyl, alkenyl or aryl.

Very particularly preferred organosiloxane surfactants are compounds having the Formula IIId

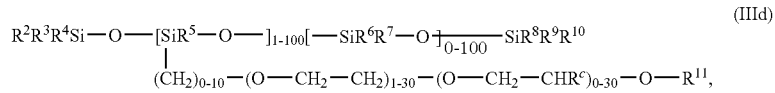
(IIId)

where $R^2$, $R^3$, $R^4$, $R^5$, $R^6$, $R^7$, $R^8$, $R^9$ and $R^{10}$, independent of one another, stand for alkyl, alkenyl, alkynyl, aryl, aryloxy, aralkyl, aralkyloxy, alkylaryl or alkylaryloxy, preferably methyl, $R^c$ stands for $C_1$-$C_6$ alkyl, preferably methyl or ethyl, or phenyl, and $R^{11}$ is hydrogen, alkyl, alkenyl or aryl, preferably hydrogen or methyl.

Other very particularly preferred organosiloxane surfactants are compounds having the Formula IIIe

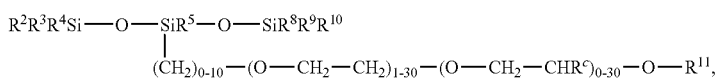
(IIIe)

where $R^2$, $R^3$, $R^4$, $R^5$, $R^8$, $R^9$ and $R^{10}$, independent of one another, stand for alkyl, alkenyl, alkynyl, aryl, aryloxy, aralkyl, aralkyloxy, alkylaryl or alkylaryloxy, preferably methyl, $R^c$ stands for $C_1$-$C_6$ alkyl, preferably methyl or ethyl, or phenyl, and $R^{11}$ is hydrogen, alkyl, alkenyl or aryl, preferably hydrogen or methyl.

Other very particularly preferred organosiloxane surfactants are compounds having the Formula IIIf

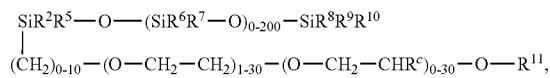
(IIIf)

where $R^2$, $R^5$, $R^6$, $R^7$, $R^8$, $R^9$ and $R^{10}$, independent of one another, stand for alkyl, alkenyl, alkynyl, aryl, aralkyl or alkylaryl, preferably methyl, $R^c$ stands for $C_1$-$C_6$ alkyl, preferably methyl or ethyl, or phenyl, and $R^{11}$ is hydrogen, alkyl, alkenyl or aryl, preferably hydrogen or methyl.

Very particularly preferably, organosiloxane surfactants having the Formula IIIg are used

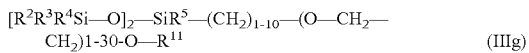
(IIIg)

where $R^2$, $R^3$, $R^4$ and $R^5$, independent of one another, stand for alkyl and/or alkenyl, preferably methyl, $R^{11}$ is hydrogen, alkyl, alkenyl or aryl, preferably hydrogen or methyl.

Very particularly preferred silicon-containing surfactants are compounds having the Formulas VII, VIII, IX and X

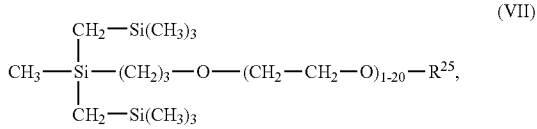
(VII)

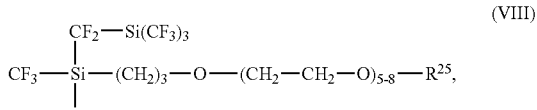
(VIII)

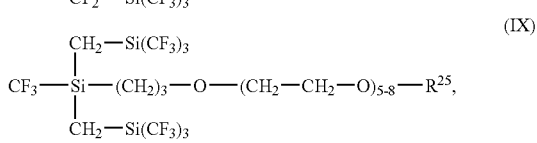
(IX)

-continued

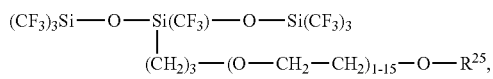
(X)

where $R^{25}$ is hydrogen, methyl, ethyl, propyl or butyl, preferably hydrogen or methyl.

These preferred silicon surfactants or carbosilane surfactants are commercially available under the trade name Masil SF 19 (Lubrizol), Silwet L77 (GE-Bayer-Silicones), for example.

Particularly preferably, carbosilane surfactants having the Formula IVa are used

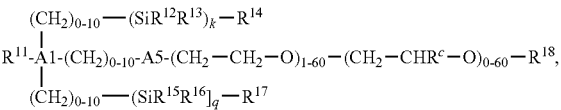
(IVa)

where $R^{11}$, $R^{12}$, $R^{13}$, $R^{14}$, $R^{15}$, $R^{16}$ and $R^{17}$, independent of one another, are hydrogen, alkyl, alkenyl, alkynyl, aryl, aralkyl or alkylaryl, the sum of k and q is 1 or 2, A5 is a group —O—, —CO—, —CO—O—, —S—, —NR$^{19}$—, —CO—NR$^{19}$—, —SO$_2$— or —SO$_2$—NR$^{19}$—, $R^{19}$ stands for hydrogen, alkyl, alkenyl or aryl, $R^c$ is $C_1$-$C_6$ alkyl, preferably methyl or ethyl, or phenyl, and $R^{18}$ stands for hydrogen, alkyl, alkenyl or aryl.

Also particularly preferably, carbosilane surfactants having the Formula Va are used

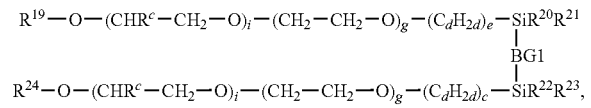
(Va)

where $R^{20}$, $R^{21}$, $R^{22}$ and $R^{23}$, independent of one another, stand for hydrogen, alkyl, alkyloxy, alkenyl, alkenyloxy, alkynyl, alkynyloxy, aryl, aryloxy, aralkyl, aralkyloxy, alkylaryl and/or alkylaryloxy, preferably hydrogen, alkyl, alkyloxy or alkenyl, d is a whole number from 1 to 10, e is 0 or 1, g and i, independent of one another, are whole numbers from 0 to 30, whereby the sum of g and i stands for 1 to 60, BG1 is a bridge group that is selected from the groups having the formulas —O—, alkylene, polyoxyalkylene, phenylene, cycloalkylene, bicycloalkadiene diyl and —C$_6$H$_5$—K—C$_6$H$_5$—, K is a direct C—C bond, —O—, —SO$_2$—, alkylene or haloalkylene, and R$^{19}$ and R$^{24}$, independent of one another, stand for hydrogen, alkyl, alkenyl or aryl.

Very particularly preferably, compounds having the Formula Va are used, where BG1 is a bridge group that is selected from the group consisting of formulas —O—, C$_1$-C$_{10}$-alkylene, —(O—CH$_2$—CHR$^c$)$_{2-60}$—, —(CH$_2$)$_{1-10}$—(O—CH$_2$—CHR$^c$)$_{2-60}$—(CH$_2$)$_{1-10}$—, phenylene, cyclohexylene, cyclopentylene, norbonene-diyl, bis-cyclopentadienyl-diyl, —C$_6$H$_5$—O—C$_6$H$_5$—, —C$_6$H$_5$—SO$_2$—C$_6$H$_5$—, —C$_6$H$_5$—C(CH$_3$)$_2$—C$_6$H$_5$— and —C$_6$H$_5$—C(CF$_3$)$_2$—C$_6$H$_5$—.

Also particularly preferably, carbosilane surfactants having the Formula VIa are used

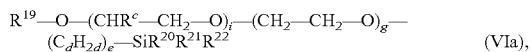

(VIa), where R$^{20}$, R$^{21}$ and R$^{22}$, independent of one another, stand for hydrogen, alkyl, alkyloxy, alkenyl, alkenyloxy, alkynyl, alkynyloxy, aryl, aryloxy, aralkyl, aralkyloxy, alkylaryl and/or alkylaryloxy, preferably hydrogen, alkyl, alkyloxy or alkenyl, d is a whole number from 1 to 10, e is 0 or 1, g and i, independent of one another, are whole numbers from 0 to 30, whereby the sum of g and i stands for 1 to 60, and R$^{19}$ and R$^{24}$, independent of one another, stand for hydrogen, alkyl, alkenyl or aryl.

Particularly preferably, fluoro-carbosilane surfactants having the Formula IVb are used

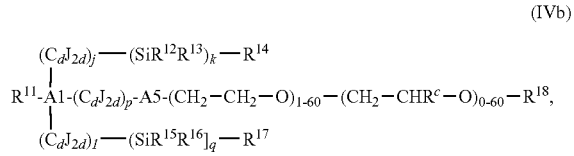

(IVb)

where R$^{11}$, R$^{12}$, R$^{13}$, R$^{14}$, R$^{15}$, R$^{16}$ and R$^{17}$, independent of one another, are hydrogen, fluorine, alkyl, alkyloxy, alkenyl, alkenyloxy, alkynyl, alkynyloxy, aryl, aryloxy, aralkyl, alkylaryl, fluoroalkyl, fluoroalkyloxy, fluoroalkenyl, fluoroalkenyloxy, fluoroalkynyl, fluoroalkynyloxy, fluoroaryl, fluoroaryloxy, fluoroaralkyl or fluoroalkylaryl, preferably hydrogen, fluorine, alkyl, fluoroalkyl, alkoxy, fluoroalkoxy, alkenyl and fluoroalkenyl, whereby at least one of these groups contains fluorine and the groups that contain fluorine can be partially fluoridated or perfluoridated, d stands for a whole number from 1 to 10, j, p and l are 0 or 1, the sum of k and q is 1 or 2, A5 is a group —O—, —CO—O—, —S—, —NR$^{19}$—, —CO—NR$^{19}$—, —SO$_2$— or —SO$_2$NR$^{19}$—, R$^{19}$ stands for hydrogen, alkyl, alkenyl or aryl, R$^c$ is C$_1$-C$_6$ alkyl, preferably methyl or ethyl, or phenyl, and R$^{18}$ stands for hydrogen, alkyl, alkenyl or aryl.

Very particularly preferably, fluorosilicon surfactants having the Formula IVc are used,

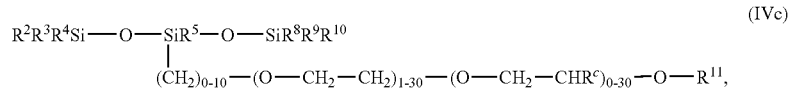

(IVc)

where R$^2$, R$^3$, R$^4$, R$^5$, R$^8$, R$^9$ and R$^{10}$, independent of one another, stand for alkyl, alkyloxy, alkenyl, alkenyloxy, alkynyl, alkynyloxy, aryl, aryloxy, aralkyl, aralkyloxy, alkylaryl or alkylaryloxy, fluoroalkyl, fluoroalkyloxy, fluoroalkenyl, fluoroalkenyloxy, fluoroalkynyl, fluoroalkynyloxy, fluoroaryl, fluoroaryloxy, fluoroaralkyl, fluoroaralkyloxy, fluoroalkylaryl or fluoroalkylaryloxy, preferably methyl, trifluoromethyl, C$_1$-C$_4$ alkoxy, C$_1$-C$_4$ fluoroalkoxy, particularly methoxy or trifluoromethyl, and/or vinyl and/or allyl, whereby at least one of these groups contains fluorine, and groups that contain fluorine can be partially fluoridated or perfluoridated, R$^c$ stands for C$_1$-C$_6$ alkyl, preferably methyl or ethyl, or phenyl, and R$^{11}$ is hydrogen, alkyl, alkenyl or aryl, preferably hydrogen or methyl.

Also particularly preferably, fluoro-carbosilane surfactants having the Formula Vc are used

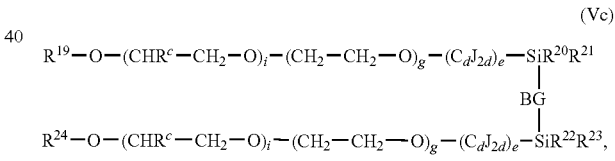

(Vc)

where R$^{20}$, R$^{21}$, R$^{22}$ and R$^{23}$, independent of one another, stand for hydrogen, fluorine, alkyl, alkyloxy, alkenyl, alkenyloxy, alkynyl, alkynyloxy, aryl, aryloxy, aralkyl, aralkyloxy, alkylaryl and/or alkylaryloxy, fluoroalkyl, fluoroalkyloxy, fluoroalkenyl, fluoroalkenyloxy, fluoroalkynyl, fluoroalkynyloxy, fluoroaryl, fluoroaryloxy, fluoroaralkyl, fluoroaralkyloxy, fluoroalkylaryl and/or fluoroalkylaryloxy, preferably hydrogen, fluorine, alkyl, fluoroalkyl, alkyloxy, fluoroalkyloxy, alkenyl or fluoroalkenyl, whereby at least one of these groups contains fluorine, and the group that contain fluorine can be partially fluoridated or perfluoridated, d is a whole number from 1 to 10, e is 0 or 1, g and i, independent of one another, are whole numbers from 0 to 30, whereby the sum of g and i stands for 1 to 60, BG is a bridge group that is selected from the groups having the formulas —O—, alkylene, polyoxyalkylene, phenylene, cycloalkylene, bicycloalkadiene diyl, and —C$_6$H$_5$—K—C$_6$H$_5$—, K is a direct C—C bond, —O—, alkylene or haloalkylene, and $R^{19}$ and $R^{24}$, independent of one another, stand for hydrogen, alkyl, alkenyl or aryl.

Very particularly preferably, compounds having the Formula Vc are used, where BG is a bridge group that is selected from the group consisting of formulas —O—, $C_1$-$C_{10}$-alkylene, —(O—$CH_2$—$CHR^c$)$_{2-60}$—, —($CH_2$)$_{1-10}$—(O—$CH_2$—$CHR^c$)$_{2-60}$—($CH_2$)$_{1-10}$—, phenylene, cyclohexylene, cyclopentylene, norbonene-diyl, bis-cyclopentadienyl-diyl, —$C_6H_5$—O—$C_6H_5$—, —$C_6H_5$—$SO_2$—$C_6H_5$—, —$C_6H_5$—$C(CH_3)_2$—$C_6H_5$— and —$C_6H_5$—$C(CF_3)_2$—$C_6H_5$—.

Also particularly preferably, fluoro-carbosilane surfactants having the Formula VIb are used

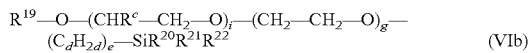

(VIb)

where $R^{20}$, $R^{21}$ and $R^{22}$, independent of one another, stand for hydrogen, fluorine, alkyl, alkenyl, alkynyl, aryl, aralkyl and/or alkylaryl, fluoroalkyl, fluoroalkenyl, fluoroalkynyl, fluoroaryl, fluoroaralkyl and/or fluoroalkylaryl, preferably hydrogen, fluorine, alkyl, fluoroalkyl, alkenyl or fluoroalkenyl, whereby at least one of these groups contains fluorine, and the groups that contain fluorine can be partially fluoridated or perfluoridated, d is a whole number from 1 to 10, e is 0 or 1, g and i, independent of one another, are whole numbers from 0 to 30, whereby the sum of g and i stands for 1 to 60, and $R^{19}$ and $R^{24}$, independent of one another, stand for hydrogen, alkyl, alkenyl or aryl.

The non-ionic silicon surfactants or non-ionic carbosilane surfactants having the Formulas II to X are used individually or in combination, particularly preferably together with the non-ionic fluorosurfactants having the Formulas I or Ia to Id or mixtures of two or more of these non-ionic fluorosurfactants.

The proportion of silicon-containing non-ionic surfactant in the dental impression mass according to the invention usually amounts to 0.05 to 5.0 wt.-%, preferably 0.1 to 5.0 wt.-%, with reference to the dental impression mass.

The proportion of non-ionic fluorosurfactant in the dental impression mass according to the invention usually amounts to 0.001 to 5.0 wt.-%, preferably 0.01 to 5.0 wt.-%, with reference to the dental impression mass.

In the synergistic surfactant mixture used according to the invention, the weight ratio of silicon-containing non-ionic surfactant to non-ionic fluorosurfactant is 100:1 to 1:100, preferably 50:1 to 1:50, particularly preferably 10:1 to 1:10, and very particularly preferably 4:1 to 1:5.

The synergistic mixtures of silicon-containing non-ionic surfactant and non-ionic fluorosurfactant used in the dental impression masses according to the invention preferably contain, as an additional component, a polyether containing alkenyl groups and/or alkynyl groups and/or a polyether terminated with hydroxyl and/or aryloxy and/or arylalkyloxy and/or alkoxy.

This additional component brings about a further improvement in the contact angle properties of the non-hardened plastic material, and thus a further improvement of the shape accuracy of the resulting impression.

Examples of preferred additives of this type are the compounds having the Formula XI)

where $R^{30}$ stands for an ethylene-unsaturated hydrocarbon group, preferably allyl, styryl, acryloyl or methacryloly, or hydrogen or alkyl, and multiple groups $R^{30}$ of a molecule can be different, within the framework of the given definition, n1 stands for a whole number from 1 to 5, preferably 1, 2 or 3, particularly 1, A stands for a group having the formula

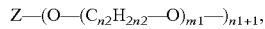

Z is an n1-valent hydrocarbon group, preferably a group derived from a bivalent, trivalent, tetravalent, pentavalent, or hexavalent aliphatic alcohol, particularly a group derived from alkylene glycol, trimethylol propane, pentaerythrite or sorbite, n2 stands for a whole number from 2 to 8, preferably from 2 to 4, and m1 is a whole number from 1 to 35000, preferably from 50 to 1500, whereby n2 and m1 can be different within a molecule, within the framework of the given definition.

The indices n2 and/or m1 can assume different values within a molecule and within an alkylene oxide chain, within the framework of the given definition. Different indices n2 and/or m1 mean that alkylene oxide units having different carbon numbers can be present, which can occur in statistical distribution or in the form of blocks, i.e. that the individual blocks within a molecule can have different lengths.

Very particularly preferably used polyethers are compounds having the Formulas XII and XIII

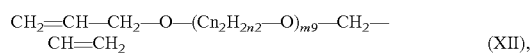

where n2 stands for a whole number from 2 to 8, preferably from 2 to 4, m9 is a whole number from 3 to 70000, preferably from 10 to 2500, whereby n2 and m9 can be different within a molecule, within the framework of the given definition, and $R^{31}$ and $R^{32}$, independent of one another, stand for hydrogen or $C_1$-$C_6$-alkyl, particularly hydrogen and/or methyl, ethyl or propyl.

Examples of particularly preferred alkylene oxide units are —$CH_2$—$CH_2$—O—, —$CH_2$—$CH_2$—$CH_2$—O—, —$CH_2$—$CH(CH_3)$—O— and —$CH_2$—$CH_2$—$CH_2$—$CH_2$—O—.

Polyethers having the Formulas XII and XIII are particularly preferred, particularly those that have ethylene oxide units or ethylene oxide units and propylene oxide units or ethylene oxide units and butylene oxide units.

These polyethers are generally used as mixtures of polymers having different chain lengths. Typical molecular weights (numerical average) lie in the range of 150 to 3000000, preferably 250 to 100000, and particularly preferably 250 to 50000.

The proportion of these polyethers in the dental impression mass according to the invention usually amounts to 0.1 to 25.0 wt.-%, preferably 0.1 to 10.0 wt.-%, and particularly preferably 0.5 to 2.5 wt.-%, with reference to the dental impression mass.

The synergistic mixtures of silicon-containing non-ionic surfactant and non-ionic fluorosurfactant used in the dental impression masses according to the invention preferably contain a polyol as an additional component.

This additional component brings about a further improvement in the contact angle properties of the non-hardened plastic material, and thus a further improvement of the detail accuracy of the resulting impression.

This additional component can be monomer, oligomer or polymer polyols. These can have primary, secondary and/or tertiary hydroxyl groups. The hydroxyl groups can be bound to aromatic groups, but preferably to aliphatic groups.

The proportion of these polyols in the dental impression mass according to the invention usually amounts to 0.1 to 25.0 wt.-%, preferably 0.1 to 10.0 wt.-%, and particularly preferably 0.5 to 2.5 wt.-%, with reference to the dental impression mass.

Preferred polyols are selected from the group of hydrocarbons, of polyvinyl alcohols, of aliphatic diols, triols, tetraols, pentaols and/or hexaols, and mixtures of two or more of these polyols.

Particularly preferred polyols are selected from the group of polyvinyl alcohols, of polysaccharides, trimethylol propane, pentaerythritol, dipentaerythritol, glycerin, allyloxy-1,2-propane diol, 2-methyl-2,4-pentane diol, trimethylol propane allyl ether, decane diol, nonane diol, octane diol, heptane diol, hexane diol, pentane diol, butane diol, propane diol, ethane diol, fructose, glucose, and mixtures of two or more of these polyols, particularly glycerin.

In another preferred embodiment, the dental impression mass according to the invention contains, aside from the polyol, a polyether containing alkenyl groups and/or alkynyl groups and/or a polyether terminated with aryloxy and/or arylalkyloxy and/or hydroxyl and/or alkoxy as an additional component.

The contact angle properties of the non-hardened plastic material can be improved by means of the presence of these two components.

In the curable polymer systems, different types can be used. The dental impression masses according to the invention can be present as single-component systems or as multi-component systems, preferably as two-component systems, as a function of the polymer system, in each instance. The curable polymer systems and their additional components, such as catalysts and/or initiators, are known to a person skilled in the art as such.

The proportion of the curable polymers in the dental impression mass according to the invention usually amounts to 5 to 80 wt.-%, preferably 20 to 70 wt.-%, with reference to the dental impression mass.

The proportion of the catalysts and/or the photoinitiators in the dental impression mass according to the invention usually amounts to 0.00005 to 10 wt.-%, preferably 0.0001 to 5 wt.-%, with reference to the dental impression mass.

Dental impression masses containing a crosslinkable polyether that has alkoxy silyl groups, aziridino groups, groups derived from an ethylene-unsaturated carboxylic acid, alkenyl groups as crosslinkable groups, groups that can be crosslinked by way of a ring-opening metathesis reaction, a crosslinking catalyst and/or photoinitiator, as well as a silicon-containing non-ionic surfactant and a non-ionic fluorosurfactant, are preferred, whereby the non-ionic fluorosurfactant consists of a partially fluoridated or perfluoridated hydrocarbon group that is connected with a (poly)alkylene oxide group by way of an oxygen atom or an ester group as a bridge group.

Particularly preferably, dental impression masses containing organopolysiloxanes are used as curable polymer systems. Such compositions are known, for example, from DE 3410646 A1. It is known that a differentiation is made between organopolysiloxanes that crosslink by means of an addition reaction, organopolysiloxanes that crosslink by means of a condensation reaction, and organopolysiloxanes that crosslink by means of a ring-opening metathesis reaction. All of these polymer systems can be used according to the invention.

Organopolysiloxanes that crosslink by means of an addition reaction are preferred.

Organopolysiloxanes that can be hardened by means of an addition reaction are known, for example, from DE 3410646 A1, DE 10017154 A1.

These are usually used in the form of a multi-component dental impression mass containing Components A and B. In this mass,
a) Component A contains an organopolysiloxane having at least two ethylene-unsaturated groups and a hydrosilylation catalyst,
b) Component B contains an organohydrogen polysiloxane, and
c) at least one of Components A and/or B contains a silicon-containing non-ionic surfactant and/or a non-ionic fluorosurfactant, and Components A and B have a composition such that after the Components A and B are mixed, a combination of the silicon-containing non-ionic surfactant and the non-ionic fluorosurfactant is present.

Usually, organopolysiloxanes that have at least two allyl or, particularly, vinyl groups bound to Si atoms are used as the organopolysiloxane having at least two ethylene-unsaturated groups.

Typically, these are compounds having the following Formulas XIV or XV

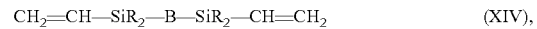

$$CH_2=CH-SiR_2-B-SiR_2-CH=CH_2 \quad (XIV),$$

or

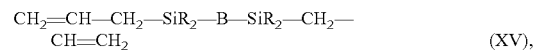

$$CH_2=CH-CH_2-SiR_2-B-SiR_2-CH_2-CH=CH_2 \quad (XV),$$

where B stands for a group having the formula $-O-(SiR_2-O)_{m2}-$, the individual Rs within the polymer chain, independent of one another, stand for alkyl, alkenyl, alkynyl, cycloalkyl, aryl and/or aralkyl, which might be substituted, and m2 is a whole number from 10 to 6000, preferably from 20 to 2000.

Organopolysiloxanes having at least two ethylene-unsaturated groups are generally used as mixtures of polymers having different chain lengths. Typical molecular weights (numerical average) are in the range from 900 to 500000, preferably from 1500 to 150000.

Examples of alkyl groups are straight-chain or branched alkyl groups with one to six carbon atoms, such as methyl, ethyl, n-propyl, isopropyl or n-butyl.

Examples of substituted alkyl groups are straight-chain or branched alkyl groups with one to six carbon atoms, substituted with one or more halogen atoms, e.g. trifluoromethyl.

Examples of cycloalkyl groups are groups having five to six ring carbon atoms, such as cyclohexyl.

Examples of aryl groups are one of the two-nuclei aromatic hydrocarbon groups, such as phenyl or naphthyl.

Examples of substituted aryl groups are phenols substituted with alkyl or halogen, such as tolyl, xylyl or chlorophenyl.

An example of an aralkyl group is benzyl.

Organopolysiloxanes having the Formulas I and/or II are particularly preferred, where R is methyl.

The compounds usually used as crosslinking agents are used as organohydrogen polysiloxanes. These can be polyalkyl, polyaryl, polyalkylaryl, polyhalogen alkyl, polyhalogen aryl and polyhalogen alkylaryl siloxanes that have at least two hydrogen atoms bound to silicon atoms in the molecule.

A typical example is compounds having the formula $R_aH_bSiO_{(4-(a+b)/2)}$, where R possesses the meaning defined above for the compounds having the Formula XIV or XV, a stands for a real number with $1<a<2$, b stands for a real number with $0<b<=1$, with the proviso that $1<a+b<2.7$, and that the compounds have at least two, preferably at least three Si—H bonds.

Preferred examples of organohydrogen polysiloxanes are the compounds having the Formula XVIa, XVIb, XVIc, XVId and XVIe

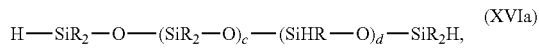

(XVIa)

(XVIb)

(XVIc)

(XVId)

(XVIe)

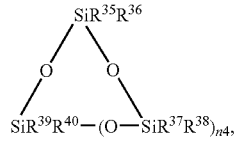

where R has the meanings defined for compounds having the Formulas XIV or XV, and different group R can assume different meanings, within the framework of the given definition, within a molecule, and particularly stand for alkyl groups, preferably methyl, $R^{35}$ to $R^{40}$, independent of one another, stand for hydrogen, alkyl, cycloalkyl, aryl or aralkyl, whereby at least two of these groups stand for hydrogen, and of the groups $R^{35}$ and $R^{36}$, or $R^{37}$ and $R^{38}$ or $R^{39}$ and $R^{40}$ only one is hydrogen, in each instance, c, d and e, independent of one another, are whole numbers from 0 to 100, whereby the sum of c, d and e amounts to 2 to 300, n3 is a whole number from 0 to 3, q and p, independent of one another, are real numbers greater than 0, with the proviso that the sum of q and p is 1, and n4 is a whole number from 1 to 5, preferably 1 or 2.

Preferably, organohydrogen polysiloxanes are used that have an SiH content of 0.01 to 15 mmol/g, preferably 0.1 to 10 mmol/g.

Other preferably used organohydrogen polysiloxanes are methyl hydrogen polysiloxanes.

Usually, salts, complexes, or colloidally present forms of the transition metals of the $8^{th}$ secondary group are used as catalysts for the hydrosilylation. Preferably, platinum, palladium or rhodium are used, in the form of metals or as complexes. Particularly preferably, platinum complexes are used, which have been produced, for example, from hexachloroplatinic acid or from platinum salts, e.g. tris(divinyl tetramethyl disiloxane) di-platinum(O) complex, platinum divinyl tetramethyl disiloxane complex.

Particularly preferred dental impression masses contain a polydialkyl siloxane having at least two vinyl groups and a platinum compound as the hydrosilylation catalyst in Component A.

Other preferred dental impression masses contain a mixture of silicon-containing non-ionic surfactant and non-ionic fluorosurfactant in Component B.

Other preferred dental impression masses contain organopolysiloxanes that crosslink by means of a condensation reaction.

Organopolysiloxanes that can harden by means of a condensation reaction are known, for example, from DE 4137698 A1.

Dental impression masses whose Component C contains a polydialkyl siloxane having at least two hydroxyl groups and whose Component D contains a polydialkyl siloxane and/or a silane having at least two dialkoxy or trialkoxy silyl groups as well as a condensation catalyst, preferably a tin compound, are preferred.

Dental impression masses whose Component D contains a mixture of a silicon-containing non-ionic surfactant and a non-ionic fluorosurfactant are also preferred.

These are usually used in the form of a multi-component dental impression mass containing Components C and D. In this d) Component C contains an organopolysiloxane having at least two hydroxyl groups, e) Component D contains a silicic acid ester, polysilicic acid ester and/or an organopolysiloxane having at least two alkoxy groups, as well as a condensation catalyst, and f) at least one of the Components C and/or D contains a silicon-containing non-ionic surfactant and/or a non-ionic fluorosurfactant, and Components C and D have a composition such that after the Components C and D are mixed, a combination of a silicon-containing non-ionic surfactant and a non-ionic fluorosurfactant is present.

Usually, organopolysiloxanes that have at least two hydroxyl groups bound to Si atoms are used as an organopolysiloxane having at least two hydroxyl groups.

Typically, these are compounds having the following Formula XVII

 (XVII), where B has the meaning defined for the compounds having the Formulas XIV and XV.

Organopolysiloxanes with hydroxyl end groups, where R is methyl, are particularly preferred.

Organopolysiloxanes having at least two hydroxyl groups are generally used as mixtures of polymers having different chain lengths. Typical molecular weights (numerical average) lie in the range 900 to 500000, preferably from 1500 to 150000.

Usually, organopolysiloxanes or organo-oxy silicon compounds that have at least two, preferably three or four alkoxy groups bound to Si atoms, are used as silanes, silicic acid esters, polysilicic acid esters and/or organopolysiloxanes having at least two alkoxy groups.

Typically, these are compounds having the following Formula XVIII and/or XIX and/or XX $$(RO)_m\text{—}SiR_{3-m}\text{—}B\text{—}SiR_{3-m}\text{—}(OR)_m, \quad (XVIII)$$

$$SiR_z(OR')_{4-z}, \quad (XIX)$$

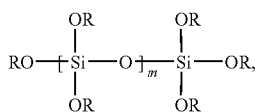
(XX)

where B possesses the meaning defined for compounds having the Formula XIV and XV, the individual Rs within the polymer chain having the Formulas XVIII or XIX or within the compound having the Formula XX, independent of one another, stand for alkyl, cycloalkyl, aryl and/or aralkyl, which can be substituted, if necessary, the individual R's within the compound having the Formula XIX, independent of one another, have one of the meanings defined for R, preferably are alkyl, z is a whole number from 0 to 2, n1 is a whole number from 1 to 100, preferably from 50 to 70, and m is a whole number from 1 to 3.

Examples of groups R are listed in the description of the vinyl-terminated and/or allyl-terminated organopolysiloxanes having the Formulas XIV and XV.

Alkoxy silicon compounds having the Formula XIX are particularly preferred, where R and R' are methyl, and z stands for 0, 1 or 2.

Organopolysiloxanes having at least two alkoxy groups are generally used as mixtures of polymers having different chain lengths. Typical molecular weights (numerical average) lie in the range from 400 to 10000, preferably from 250 to 5000.

Usually, organo-tin compounds, titanates, zirconates or bismuthates are used as catalysts for the condensation reaction, for example tetraethyl titanate, tetraisopropyl titanate, tetra-n-propyl titanate, tetra-n-butyl titanate, n-butyl-polytitanate, tetra-2-ethyl hexyl-titanate, tetraisooctyl titanate, octylene glycol titanate, tetra-n-propyl zirconate, tetra-n-butyl zirconate, tin-II-isooctoate, dioctyl tin dicarboxylate, dioctyl tin dilaurate, dibutyl tin dilaurate, organo-tin carboxylate, dibutyl tin carboxylate, dibutyl tin acetyl acetonate, dibutyl tin diacetate, and bismuth-II ethyl hexanoate.

Other preferred dental impression masses contain polyethers containing alkenyl groups.

Curable systems of this type are known, for example, from DE-A-4010281.

Dental impression masses whose Component E contains a polyalkylene ether having at least two alkylene groups and a platinum compound as a hydrosilylation catalyst are preferred.

Also preferred are dental impression masses whose Component F contains a mixture of a silicon-containing non-ionic surfactant and a non-ionic fluorosurfactant.

These are usually used in the form of a multi-component dental impression mass containing Components E and F. In this, g) Component E contains a crosslinking catalyst, h) Component F contains a crosslinkable polyether that contains alkenyl groups, as well as an organohydrogen polysiloxane and/or SiH polyether, and i) at least one of the Components E and/or F contains a silicon-containing non-ionic surfactant and/or a non-ionic fluorosurfactant, and Components E and F have a composition such that after Components E and F are mixed, a combination of the silicon-containing non-ionic surfactant and the non-ionic fluorosurfactant is present.

Possible polyethers having alkenyl groups are usually groups that are derived from polyalkylene glycols and are ethylene-unsaturated, for example polymers terminated with allyl ether groups.

Typically, these are compounds having the following Formula XXI $$X\text{-}A\text{-}(X)_{n1} \quad (XXI),$$

where A and n1 possess the meaning defined for compounds having the Formula XI and X is an alkenyl group with an end-position double bond.

Examples of alkenyl groups with an end-position double bond X are $-CH_2-CH=CH_2$, $-SiR_2-CH=CH_2$, $-CR_2-CH=CH_2$ and $-C_6H_4-CH=CH_2$, where R stands for alkyl groups.

Polyethers having the Formula XXI, which have ethylene oxide and/or propylene oxide units, particularly those with end-position allyl groups, are particularly preferred.

Polyethers having alkenyl groups are generally used as mixtures of polymers having different chain lengths. Typical molecular weights (numerical average) lie in the range of 150 to 3000000, preferably of 250 to 100000.

Possible organohydrogen polysiloxanes are the compounds already described further above, in connection with the description of the organopolysiloxanes that crosslink by means of an addition reaction.

In this crosslinkable polymer system, as well, organohydrogen polysiloxanes that have an SiH content of 0.01 to 15 mmol/g, preferably of 0.1 to 10 mmol/g, are preferably used.

Other organohydrogen polysiloxanes that are preferably used are methyl hydrogen polysiloxanes.

Possible SiH polyethers are compounds having the Formula XXII $$Y\text{-}A\text{-}(Y)_{n1} \quad (XXII),$$

where A and n1 possess the meaning defined for compounds having the Formula XI, and Y is a group containing a silicon hydrogen group.

Examples of groups Y are groups having the Formula $-R'-SiR^2H$ or the Formula XVIf

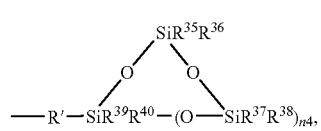
(XVIf)

where R' stands for an alkylene group, preferably with one to six carbon atoms,

R has the meaning defined for compounds having the Formulas XIV or XV, and different groups R within a molecule can assume different meanings, within the framework of the given definition, and particularly stand for alkyl groups, preferably methyl, and $R^{35}$ to $R^{40}$ as well as n4 possess the meaning defined above for groups having the Formula XVIe.

In this curable system, as well, the salts, complexes, or colloidally present forms of the transition metals of the $8^{th}$ secondary group are used as catalysts. Preferably, platinum, palladium or rhodium are used, in the form of metals or as complexes. Particularly preferably, platinum complexes are used, which have been produced, for example, from hexachloroplatinic acid or from platinum salts, for example tris(divinyl tetramethyl disiloxane) diplatinum(O)-complex, platinum-divinyl tetramethyl disiloxane complex.

Other preferred dental impression masses contain polyethers containing alkoxy silyl groups.

Curable systems of this type are known, for example, from PCT/EP2005/001470 and from EP-A-1,226,808.

Dental impression masses that contain a polyalkylene ether with at least two alkoxy silyl groups and a tin compound and/or organic acids and/or bases and/or their salts as a condensation catalyst are preferred.

Curable systems of this type are preferably used in the form of a multi-component dental impression mass containing Components G and H. In this, j) Component G contains a crosslinkable polyether that contains alkoxy silyl groups, k) Component H contains water, l) at least one of the Components G and/or H contain a catalyst as well as a silicon-containing non-ionic surfactant and/or a non-ionic fluorosurfactant, and Components G and H have a composition such that after Components G and H are mixed, a combination of silicon-containing non-ionic surfactant and non-ionic fluorosurfactant is present.

Possible polyethers having alkoxy silyl groups are usually polymers derived from polyalkylene glycols and terminated with alkoxy silyl groups, if necessary by way of a bridge group.

Typically, these are compounds having the Formula XXIII

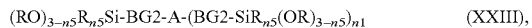

$(RO)_{3-n5}R_{n5}Si-BG2-A-(BG2-SiR_{n5}(OR)_{3-n5})_{n1}$ (XXIII), where A and n1 possess the meaning defined for compounds having the Formula XI, BG2 stands for a covalent bond or a bridge group, with the exception of —O—, n5 stands for a whole number from 0 to 2, R has the meaning defined for compounds having the Formulas XIV or XV, and within a molecule, different groups R, Br as well as different indices n5 can assume different meanings, within the given definition, R particularly stands for alkyl groups, preferably methyl, and BG2 is particularly a covalent bond or a bridge group —O—CO—NH—R'—, where R' is connected with the silicon atom and stands for an alkyl group, preferably methyl, ethyl or propyl.

Polyethers having alkoxy silyl groups can also be used as mixtures of polymers having different chain lengths. Typical molecular weights (numerical average) lie in the range of 150 to 3000000, preferably of 250 to 100000 and particularly preferably 250 to 50000.

The organo tin compounds described further above, for example dibutyl tin dilaurate, can be used as catalysts in this curable system. However, organic acids, such as toluene sulfonic acid, or organic bases, such as amines, guanidine, DBU or DBN, or salts of these acids or bases, can also be used.

Other preferred dental impression masses contain polyethers containing aziridino groups.

Curable systems of this type are known, for example, from U.S. Pat. No. 4,353,242.

In compositions containing crosslinkable polyethers that contain alkoxy silyl groups, aziridino groups, groups derived from an ethylene-unsaturated carboxylic acid, or alkenyl groups as crosslinkable groups, or groups that crosslink by way of a ring-opening metathesis reaction, the use of silicon-containing non-ionic surfactants can be eliminated, if applicable, so that here, only a non-ionic fluorosurfactant or a mixture of non-ionic fluorosurfactants is used.

Dental impression masses containing crosslinkable polyethers that have alkoxy silyl groups, aziridino groups, groups derived from an ethylene-unsaturated carboxylic acid, or alkenyl groups as crosslinkable groups, or groups that crosslink by way of a ring-opening metathesis reaction, and a non-ionic fluorosurfactant that has at least one partially fluoridated or perfluoridated hydrocarbon group that is connected with a (poly)alkylene oxide group, a hydrocarbon group, an aliphatic polyhydroxy group or heterocyclic group containing nitrogen, by way of an oxygen atom, an amino group, a keto group, a carboxylic acid ester group, a phosphoric acid ester group, a carboxylic acid amide group and/or a phosphoric acid amide group, or that has at least one partially fluoridated or perfluoridated hydrocarbon group and at least one amino oxide group, are also an object of the present invention Preferred fluorosurfactants that are used in this embodiment are non-ionic fluorosurfactants having at least one (poly)alkylene oxide group, containing at least one partially fluoridated or perfluoridated hydrocarbon group that is connected with the (poly)alkylene oxide group by way of an oxygen atom or a carboxylic acid ester group.

Particularly preferred dental impression masses of this type contain crosslinkable polyethers that have alkoxy silyl groups or aziridino groups as crosslinkable groups.

In the case of these dental impression masses, as well, additional components used are preferably polyethers containing polyols and/or alkenyl groups and/or alkynyl groups, and/or hydroxyl-terminated and/or alkoxy-terminated polyethers.

Preferably, however, in these dental impression masses, mixtures of silicon-containing non-ionic surfactants and non-ionic fluorosurfactants are used, if necessary in combination with the aforementioned additional polyol and/or polyether components.

Curable systems of this type are usually used in the form of a multi-component dental impression mass containing Components I and J. In this, m) Component I contains a crosslinkable polyether that has aziridino groups or alkoxy silyl groups, or a polyether containing groups that can crosslink by way of a ring-opening metathesis reaction, n) Component J contains a catalyst, and o) at least one of the Components I and/or J contains a non-ionic fluorosurfactant and, if necessary, a silicon-containing non-ionic surfactant.

Preferably, Components I and J have a composition such that after Components I and J are mixed, a combination of silicon-containing non-ionic surfactant and non-ionic fluorosurfactant is present.

Usually, polymers derived from polyalkylene glycols and terminated with alkoxy silyl groups or with aziridino groups by way of a bridge group are possible as polyethers having aziridino groups or alkoxy silyl groups.

Typically, these are compounds having the following Formula XXVIII

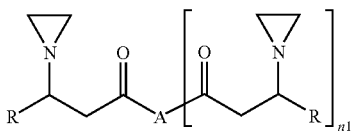

(XXVIII)

where A and n1 possess the meaning defined for compounds having the Formula XI,

R has the meanings defined for compounds having the Formulas XIV or XV, and within a molecule, different groups R can assume different meanings, within the framework of the given definition, and R, in particular, stands for alkyl groups, preferably methyl.

Polyethers having aziridino groups are generally used as mixtures of polymers having different chain lengths. Typical molecular weights (numerical average) lie in the range of 150 to 3000000, preferably of 250 to 100000, and particularly preferably 250 to 50000.

In this curable system, sulfonium salts can be used as catalysts.

Other preferred dental impression masses contain polyethers containing ester groups of an ethylene-unsaturated carboxylic acid.

Curable systems of this type are known, for example, from EP 0170219 A2.

Dental impression masses that contain a crosslinkable polyalkylene ether that has groups derived from acrylic acid and/or methacrylic acid, an initiator that can be activated by heat or by radiation, as well as a silicon-containing non-ionic surfactant and a non-ionic fluorosurfactant are preferred.

These dental impression masses can be used as one-component or two-component formulations.

Preferably, one-component dental impression masses are used that are cured by means of UV radiation and/or heat. Aside from the curable polymer system as well as the surfactant mixture used according to the invention, photoinitiators are usually contained in them.

Usually, possible crosslinkable polyethers are polymers derived from polyalkylene glycols and terminated with ethylene-unsaturated carboxylic acids.

Typically, these are compounds having the Formulas XXIV and/or XXVIII

(XXIV),

(XXVIII)

where A and n1 possess the meaning defined for compounds having the Formula XI, $R^{50}$ is an ethylene-unsaturated group, preferably an alkenyl group, and the groups $R^{50}$ within a molecule can be different, within the framework of the given meaning.

Very particularly preferably, $R^{50}$ is $CH_2=CH-$ or $CH_2=C(CH_3)-$, in other words a group derived from acrylic acid or methacrylic acid.

Polyethers containing ethylene-unsaturated carboxylic acid ester groups are generally used as mixtures of polymers having different chain lengths. Typical molecular weights (numerical average) lie in the range of 150 to 3000000, preferably of 250 to 100000, and particularly preferably 250 to 50000.

These polyethers are usually cured by means of electromagnetic radiation, preferably UV radiation or visible light. In this curable system, camphor quinone and/or amines can be used as photoinitiators.

In heat-curable systems, peroxide hardeners, if necessary combined with amines, are preferably used.

Other preferred dental impression masses contain polyethers that have groups that can crosslink by way of ring-opening metathesis polymerization (ROMP), polysiloxanes and/or synthetic rubbers. Curable systems of this type are known, for example, from EP 1317917 A1, U.S. Pat. No. 6,649,146 B2, WO 02/32338 A2 and U.S. Pat. No. 6,455,029.

These are usually used in the form of a multi-component dental impression mass containing Components K and L. In this, p) Component K contains polyethers, polysiloxanes and/or synthetic rubbers that have groups crosslinkable by way of ROMP, q) Component L contains a ROMP crosslinking catalyst, and r) at least one of the Components K and/or L contains a silicon-containing non-ionic surfactant and/or a non-ionic fluorosurfactant, and Components K and L have a composition such that after the Components K and L are mixed, a combination of silicon-containing non-ionic surfactant and non-ionic fluorosurfactant is present.

Usually, polymers derived from polyalkylene glycols, polydialkyl or aryl siloxanes and/or polyalkenes or polyalkane dienes, provided with unsaturated groups MT bound in the end and/or side position by way of a spacer B, are possible as polyethers having groups crosslinkable by way of ROMP, polysiloxanes and/or synthetic rubbers.

In this connection, the polysiloxanes are typically compounds having the following Formula XXV

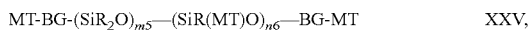
XXV, where R, independent of one another, stands for alkyl, cycloalkyl, aryl and/or aralkyl, which can be substituted, m5 is a whole number from 10 to 6000, preferably from 20 to 2000, n6 is a whole number from 0 to 100, preferably from 0 to 10, BG stands for a bridge group, MT is a group crosslinkable by way of ROMP, and the groups MT, B2 and R as well as the indices m5 and/or n6, within a molecule, can be different, within the framework of the given meaning.

Typical molecular weights (numerical average) of compounds having the Formula XXV lie in the range of 900 to 500000, preferably of 1500 to 150000.

Organopolysiloxanes with at least two ethylene-unsaturated groups are generally used as mixtures of polymers having different chain lengths. Typical molecular weights (numerical average) lie in the range of 900 to 500000, preferably of 1500 to 150000.

Organopolysiloxanes having the Formulas XXV, where R is methyl, are particularly preferred.

The polyalkylene glycols are typically compounds having the following Formulas XXVI and/or XXIX

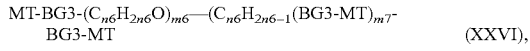
(XXVI),

(XXIX), where A and n1 possess the meaning defined for compounds having the Formula XI, n6 stands for a whole number from 4 to 8, preferably from 2 to 4, m6 is a whole number from 2 to 70000, preferably from 10 to 2500, m7 is a whole number from 0 to 70000, preferably from 10 to 2500, the sum of m6 and m7 is 3 to 70000, preferably 10 to 2500, BG3 stands for a bridge group, MT is a group crosslinkable by way of ROMP, and the groups MT and BG3 as well as the indices n6, m6 and/or m7, within a molecule, can be different within the framework of the given meaning.

In this connection, the synthetic rubbers are typically compounds having the following Formula XXVII

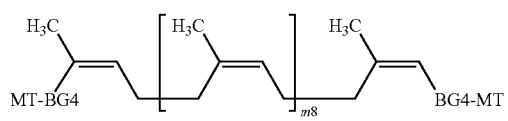

XXVII where BG4 stands for a bridge group,

MT is a group crosslinkable by way of ROMP, and m8 is a whole number from 1500 to 30000, preferably 20 to 500.

Aside from 1,4 cis and 1,4 trans polyisoprene and their mixed forms, polymers of 1,3-dienes, such as 2,3-dimethyl-1,3-butadiene, polybutadiene, and poly-(2-chloro-1,3-butadiene), for example, as well as synthetic rubbers that were formed by means of copolymerization of two or three different monomers. The most important synthetic rubbers are styrene butadiene rubber, acryl nitrile butadiene rubber and isobutene isoprene rubber, ethylene propylene copolymers (EPM), ethylene propylene diene terpolymers (EPDM), furthermore elastomers on the basis of polyurethane, polysulfidene, chlorosulfonyl polyethylene, whereby the synthetic rubber can be present, crosslinked by means of vulcanisation.

The unsaturated ROMP-crosslinkable groups MT are cycloalkenyl groups, for example, such as cyclobutenyl, cyclopentenyl groups, for example, or groups having the general formula

where $X$=O, S, NH or a saturated or unsaturated $C_1$-$C_{30}$ hydrocarbon group.

The bridge group BG4 in the formulas listed above is preferably —O— or alkylene, particularly —CH$_2$—, —CH$_2$CH$_2$—, —CH$_2$CH$_2$CH$_2$— or —CH(CH$_3$)—CH$_2$—.

In this curable system, salts, complexes or colloidal forms of the transition metals of the $8^{th}$ secondary group are used as catalysts. Preferably, ruthenium, osmium, tungsten or molybdenum are used as complexes. Particularly preferably, ruthenium-carbene complexes are used, such as Grubbs' catalyst, for example.

The dental impression masses according to the invention, containing curable polymers selected from the group of polyethers containing addition-crosslinking organopolysiloxanes, of condensation-crosslinking organopolysiloxanes, of condensation-crosslinking alkoxy silyl groups, of polyethers containing addition-crosslinking aziridino groups, of polyethers containing addition-crosslinking alkenyl groups, of polyethers containing ester groups of an ethylene-unsaturated carboxylic acid, which crosslink by means of a radical polymerization reaction, or of polyethers that crosslink by means of a ring-opening metathesis reaction, silicones or rubbers, preferably contain, as an additional component, a polyether containing alkenyl groups and/or a hydroxyl-terminated or alkoxy-terminated polyether. This additional component brings about a further improvement in the contact angle properties of the non-cured plastic material, and thus a further improvement in the detail accuracy of the resulting impression.

Examples of preferred additives of this type are the compounds described further above, having the Formula XI, XII and XIII.

The dental impression masses according to the invention can contain additional components, aside from the crosslinkable polymers and the non-ionic fluorosurfactant or the surfactant mixture, which components are usually used in such masses. Examples of such additional components are fillers. These can be reinforcing fillers or non-reinforcing fillers, or mixtures of them.

Highly disperse, active fillers having a BET surface of at least 50 m$^2$/g are particularly suitable as reinforcing fillers. Those having an individual particle size in the nanometer range, which can be present as aggregates and/or agglomerates, are particularly suitable. Preferred reinforcing fillers are substances that are selected from the group consisting of aluminum hydroxide, zinc oxide, titanium dioxide, zirconium oxide, silicon dioxide, as well as precipitated and/or pyrogenic silicic acid. Of course, the compounds mentioned above can be used individually or in any desired combination with one another, specifically both in hydrophilic and in hydrophobic form.

Furthermore preferably, the at least one reinforcing filler is present in the form of nanoparticles, as a filler in fiber or lamella form, for example as a mineral, fiber-form filler, or as a synthetic, fiber-form filler.

The proportion of reinforcing filler in the dental impression mass according to the invention usually amounts to 0 to 80 wt.-%, preferably 0.1 to 50 wt.-%, and particularly preferably 0.1 to 40 wt.-%, with reference to the total dental impression mass.

Fundamentally, the same substances are suitable as non-reinforcing fillers as those for reinforcing fillers, whereby the non-reinforcing fillers, however, necessarily have a BET surface of less than 50 m$^2$/g (Schriftenreihe Pigmente Degussa Kieselsäuren [monograph series on pigments, Degussa silicic acids], Number 12, page 5 and Number 13, page 3). Preferred non-reinforcing fillers are substances that are selected from the group consisting of earth alkali metal oxides, earth alkali metal hydroxides, earth alkali metal fluorides, earth alkali metal carbonates, calcium apatite (Ca$_5$[(F, Cl, OH, ½CO$_3$)|(PO$_4$)$_3$], particularly calcium hydroxyl apatite (Ca$_5$[(OH)|(PO$_4$)$_3$], titanium dioxide, zirconium oxide, aluminum hydroxide, silicon dioxide, precipitated silicic acid, and calcium carbonate. Of course, the compounds mentioned above can be used individually or in any desired combination with one another, specifically also both in hydrophilic and in hydrophobic form.

Preferably, the non-reinforcing fillers used have an average grain size of greater than 0.1 μm (Ullmann Encyclopädie der Technischen Chemie (Ullmann's Encyclopedia of Technical Chemistry), Volume 21, page 523).

The proportion of non-reinforcing filler in the dental impression mass according to the invention usually amounts to 0 to 80 wt.-%, preferably 0.1 to 50 wt.-%, and particularly preferably 0.1 to 40 wt.-%, with reference to the total dental impression mass.

The total proportion of reinforcing and non-reinforcing fillers in the dental impression mass according to the invention usually amounts to 0 to 80 wt.-%, preferably 0.01 to 80 wt.-%, particularly preferably 0.05 to 75 wt.-%, and very particularly preferably 0.1 to 70 wt.-%, with reference to the total dental impression mass.

The dental impression masses according to the invention can furthermore contain one or more of the following additives: buffer salts, water collectors, paste forming agents, other surfactants, active substances, plasticizers, substances that allow optical scanning, flavor and/or scent substances, substances that allow diagnostics, fluoridation agents, bleach substances, desensitization agents, adhesion bond mediators, pigments, indicators, stabilizers (antioxidants), as well as antibacterial substances.

If the dental impression mass according to the invention is present as a multi-component system, it is preferably stored in suitable primary packaging, such as tubes, cans, and particularly preferably in cartridges and tubular bags, as they are described in EP-A-723,807, EP-A-541,972, WO 98/44860 A1, EP-A-492,412, EP-A-492,413, and EP-A-956,908, for example, and proportioned tailored to subsequent use.

Dental impression materials containing the following are very particularly preferred:
- a) 25 to 85 wt.-% organopolydialkyl siloxane with at least two alkenyl groups,
- b) 1 to 70 wt.-% organohydrogen polysiloxane with an SiH content of 0.1 to 15.0 mmol/g,
- c) 0.0001 to 2 wt.-% hydrosilylation catalyst, particularly salts, complexes and colloidally present forms of the transition metals of the $8^{th}$ secondary group,
- d) 0 to 90 wt.-% non-reinforcing fillers with a BET surface of less than 50 $m^2/g$,
- e) 0.1 to 50 wt.-% reinforcing fillers with a BET surface of greater than or equal to 50 $m^2/g$,
- f) 0 to 20 wt.-% ancillary substances and additives, such as plasticizers, pigments, stabilizers, inhibitors, alkyl-closed fatty alcohol ethoxylates, etc.
- g) 0.01 to 5.0 wt.-% non-ionic polyether siloxane surfactant with 3 to 7 silicon atoms in the siloxane partial structure and/or non-ionic polyether carbosilane surfactant with 1 to 7 silicon atoms in the carbosilane partial structure and an alkylene oxide proportion of 1 to 20 units, and
- h) 0.001 to 5.0 wt.-% non-ionic head-tail fluorosurfactant with a hydrophilic head that is formed from 1 to 20 alkylene oxide units and with a hydrophobic tail that is formed from partly or perfluoroalkyl groups with 3 to 30, preferably 5 to 29 fluorine atoms, whereby the ratio of the surfactants g) and h) is preferably 100:1 to 1:100, particularly preferably 50:1 to 1:50, very particularly preferably 10:1 to 1:10, and especially preferably 5:1 to 1:5.

Two-component dental impression materials containing the components a) to h) defined above, in the amounts indicated, and in addition, i) 0.1 to 25 wt.-%, preferably 0.1 to 10.0 wt.-%, particularly preferably 0.5 to 5.0 wt.-%, and very particularly preferably 0.5 to 2.5 wt.-% of branched or linear alkyl, hydroxy, alkynyl, and/or alkenyl end-stopped polyalkylene ether and/or mixtures of them, are particularly preferred, whereby the weight ratio of organopolysiloxane a) to the polyether i) is preferably 1:1 to 80:1, particularly preferably 1:1 to 60:1, very particularly preferably 1:1 to 40:1, and especially preferably 1:1 to 30:1.

Two-component dental impression materials containing the components a) to h) defined above, in the indicated amounts, and, in addition k) 0.1 to 25 wt.-%, preferably 0.1 to 10.0 wt.-%, particularly preferably 0.5 to 5.0 wt.-%, and very particularly preferably 0.5 to 2.5 wt.-% of a polyol or a mixture of polyols, are particularly preferred.

Two-component dental impression materials containing the components a) to h) defined above, in the indicated amounts, and, in addition, the components i) and k) defined above, in the indicated amounts, are very particularly preferred.

Two-component dental impression materials consisting of Component A and B are very particularly preferred, where Component A contains
- a) 10 to 80 wt.-% organopolydialkyl siloxane with at least two alkenyl groups,
- c) 0.0001 to 2 wt.-% hydrosilylation catalyst, particularly salts, complexes and colloidally present forms of the transition metals of the $8^{th}$ secondary group,
- d) 0 to 90 wt.-% non-reinforcing fillers with a BET surface of less than 50 $m^2/kg$,
- e) 0.1 to 50 wt.-% reinforcing filler with a BET surface of greater than or equal to 50 $m^2/kg$,
- f) 0 to 20 wt.-% ancillary substances and additives, such as plasticizers, pigments, stabilizers and/or inhibitors, and
- j) 0.001 to 5.0 wt.-% alkyl-closed, aryl-closed, aralkyl-closed non-ionic surfactants, preferably alkyl-closed fatty alcohol ethoxylates, silicon surfactants, polyether carbosilanes, carbosilane surfactants, and fluorosurfactants that are alkyl-closed and, in particular, alkyl-closed fatty alcohol ethoxylates, and Component B contains,
- a) 0.1 to 70 wt.-% organopolydialkyl siloxane with at least two alkenyl groups,
- b) 1.2 to 80 wt.-% organohydrogen polysiloxane with an SiH content of 0.1 to 15.0 mmol/kg,
- d) 0 to 90 wt.-% non-reinforcing fillers with a BET surface of less than 50 $m^2/kg$,
- e) 0.1 to 50 wt.-% reinforcing fillers with a BET surface of greater than or equal to 50 $m^2/kg$,
- f) 0 to 20 wt.-% ancillary substances and additives, such as plasticizers, pigments, stabilizers and/or inhibitors,
- g) 0.01 to 10.0 wt.-% non-ionic polyether siloxane surfactant with 3 to 7 silicon atoms in the siloxane partial structure and/or non-ionic polyether carbosilane surfactant with 1 to 7 silicon atoms in the carbosilane partial structure, and an alkylene oxide proportion of 1 to 20 units,
- h) 0.001 to 10.0 wt.-% non-ionic head-tail fluorosurfactant with a hydrophilic head, which is formed from 1 to 20 alkylene oxide units, and with a hydrophobic tail that is formed from partially or perfluoroalkyl groups with 3 to 30, preferably 5 to 29 fluorine atoms, whereby the ratio of the surfactants g) and h) is preferably 25:1 to 1:25, particularly preferably 20:1 to 1:5, very particularly preferably 10:1 to 1:5, and especially preferably 5:1 to 1:3, and
- i) 0.5 to 50 wt.-% branched or linear alkyl and/or alkynyl and/or alkenyl and/or hydroxyl end-stopped polyalkylene ether and/or mixtures of them, whereby the weight ratio of organopolysiloxane a) to polyether i) is 1:50 to 50:1, preferably 10:1 to 1:10, and especially preferably 4:1 to 1:5.

Also very particularly preferred are two-component dental impression materials consisting of Component A and B, where Component A contains
- a) 10 to 80 wt.-% organopolydialkyl siloxane with at least two alkenyl groups,
- c) 0,0001 to 2 wt.-% hydrosilylation catalyst, particularly salts, complexes and colloidally present forms of the transition metals of the $8^{th}$ secondary group,
- d) 0 to 90 wt.-% non-reinforcing fillers with a BET surface of less than 50 m$^2$/kg,
- e) 0.1 to 50 wt.-% reinforcing fillers with a BET surface of greater than or equal to 50 m2/kg,
- f) 0 to 20 wt.-% ancillary substances and additives, such as plasticizers, pigments, stabilizers and/or inhibitors, and
- j) 0.001 to 5.0 wt.-% alkyl-closed, aryl-closed, aralkyl-closed non-ionic surfactants, preferably alkyl-closed fatty alcohol ethoxylates, silicon surfactants, polyether carbosilanes, carbosilane surfactants and fluorosurfactants that are alkyl-closed and, in particular, alkyl-closed fatty alcohol ethoxylates, and Component B contains
- a) 0.1 to 70 wt.-% organopolydialkyl siloxane with at least two alkenyl groups,
- b) 1.2 to 80 wt.-% organohydrogen polysiloxane with an SiH content of 0.1 to 15.0 mmol/kg,
- d) 0 to 90 wt.-% non-reinforcing fillers with a BET surface of less than 50 m$^2$/kg,
- e) 0.1 to 50 wt.-% reinforcing fillers with a BET surface of greater than or equal to 50 m$^2$/kg,
- f) 0 to 20 wt.-% ancillary substances and additives, such as plasticizers, pigments, stabilizers and/or inhibitors,
- g) 0.01 to 10.0 wt.-% non-ionic polyether siloxane surfactant with 3 to 7 silicon atoms in the siloxane partial structure and/or non-ionic polyether carbosilane surfactant with 1 to 7 silicon atoms in the carbosilane partial structure and an alkylene oxide proportion of 1 to 20 units,
- h) 0.001 to 10.0 wt.-% non-ionic head-tail-fluorosurfactant with a hydrophilic head that is formed from 1 to 20 alkylene oxide units and with a hydrophobic tail that is formed from partially or perfluoroalkyl groups with 3 to 30, preferably 5 to 29 fluorine atoms, whereby the ratio of the surfactants g) and h) is 25:1 to 1:25, preferably 20:1 to 1:5, particularly preferably 10:1 to 1:5, and especially preferably 5:1 to 1:3, and
- k) 0.5 to 50 wt.-% polyol and/or mixtures of polyols.

Other very particularly preferred two-component dental impression materials containing the components a) to h) defined above, in the indicated amounts, and, in addition, the components i) and k) defined above, in the indicated amounts.

In this connection, the amount information in the above embodiment relates to the total mass of Component A or Component B, in each instance.

Another object of the present invention is mixtures that can be obtained by means of mixing individual components of multi-component masses of the dental impression materials described above. Preferably, a base component is mixed with a catalyst component in a ratio of 1:2 to 20:1, particularly preferably of 1:1 to 10:1, and very particularly preferably of 10:1, 5:1, 4:1, 2:1, and 1:1. These mixtures are characterized by excellent wettability and outstanding flow behavior onto damp tooth and gum substance. Despite these good hydrophilic properties, the material does not swell when it makes contact with aqueous media, such as water, saliva, blood, disinfectant bath or aqueous plaster paste. The good initial wettability of the mixtures is important for detail-accurate forming of the impression material in the patient's mouth during processing and the first contact with damp mouth/tooth substance, and expresses itself by means of an extremely low contact angle that rapidly forms after the components are mixed, or after the start of hardening. The dental impression masses according to the invention are characterized in that contact angles of less than or equal to 10° are achieved between 30 seconds after the start of mixing the components of the curable polymer system, e.g. the catalyst component and the base component, or of triggering hardening by means of radiation, up to binding of the curable polymer system, at a water droplet age in the first 10 seconds, preferably in the first 5 seconds after the water droplet is set onto the surface of the dental impression materials. In this connection, the contact angles are measured using a contact angle measurement device G40/G23M from Krüss, at 23° C.±1° C., with the "lying droplet" measurement method. The measurement took place at 50% relative humidity.

For this purpose, dynamic contact angle determinations were carried out, on the lying droplet, with the contact angle measurement device droplet contour analysis system DSA100 (Krüss, Hamburg, Germany), which was combined with a fully automated droplet metering system, at room temperature 23° C.±1° C. The measurement also took place at 50% relative humidity.

Wetting was initiated 40 s, 60 s, 90 s, and 120 s after the start of mixing the two-component dental impression material, in each instance, i.e. during its processing time, by means of placing a water droplet with a volume of 2 μl onto the polymerizing surface. In this connection, the dynamic change in the droplet geometry was recorded at a resolution of 10 images per second, for the duration of an individual measurement of 180 s, in each instance, and evaluated with the manufacturer software. The contact angles of the individual images were determined using the "circle fit" method, as averaged contact angles, from the left and right contact angles of the individual droplet contours.

Furthermore, the hardened impression material at the time plaster is cast into it (immediately or 2 hours after hardening), is also characterized by a contact angle of less than 10° at a water droplet age in the first 10 seconds, preferably 5 seconds after setting the water droplet onto the surface of the dental impression material.

The invention also relates to the hardened impression material that can be obtained by means of curing the dental impression masses described above. The cured impression material is characterized by excellent mechanical properties and fulfills all the requirements according to ISO 4823 with regard to an elastomer dental impression material.

The invention furthermore relates to the use of a mixture of silicon-containing non-ionic surfactant that has at least one (poly)alkylene oxide group and a molecular mass of less than 6000 g/mol, and of non-ionic fluorosurfactant that has at least one partially fluoridated or perfluoridated hydrocarbon group that is connected with a (poly)alkylene oxide group, a hydrocarbon group, an aliphatic polyhydroxy group, or a heterocyclic group that contains nitrogen, by way of an oxygen atom, an amino group, a keto group, a carboxylic acid ester group, a phosphoric acid ester group, a carboxylic acid amide group and/or a phosphoric acid amide group, or that has at least one partially fluoridated or perfluoridated hydrocarbon group and at least one amino oxide group, for the production of elastomer dental impression masses. The invention furthermore relates to the use of a mixture containing silicon-containing non-ionic surfactant that has at least one (poly)alkylene oxide group and a molecular mass of less than 6000 g/mol, non-ionic fluorosurfactant that has at least one partially fluoridated or perfluoridated hydrocarbon group that is connected with a (poly)alkylene oxide group, a hydrocarbon group, an aliphatic polyhydroxy group, or a heterocyclic group that contains nitrogen, by way of an oxygen atom, an amino group, a keto group, a carboxylic acid ester group, a phosphoric acid ester group, a carboxylic acid amide group and/or a phosphoric acid amide group, or that has at least one partially fluoridated or perfluoridated hydrocarbon group and at least one amino oxide group, and an alkenyl, alkynyl, alkyloxy, aryloxy, aralkyloxy and/or hydroxy end-stopped polyalkylene ether or a mixture of such compounds, for the production of elastomer dental impression masses.

The invention furthermore relates to the use of a mixture containing silicon-containing non-ionic surfactant that has at least one (poly)alkylene oxide group and a molecular mass of less than 6000 g/mol, non-ionic fluorosurfactant that has at least one partially fluoridated or perfluoridated hydrocarbon group that is connected with a (poly)alkylene oxide group, a hydrocarbon group, an aliphatic polyhydroxy group, or a heterocyclic group that contains nitrogen, by way of an oxygen atom, an amino group, a keto group, a carboxylic acid ester group, a phosphoric acid ester group, a carboxylic acid amide group and/or a phosphoric acid amide group, or that has at least one partially fluoridated or perfluoridated hydrocarbon group and at least one amino oxide group, and an alkenyl, alkynyl, alkyl and/or hydroxy end-stopped polyalkylene ether or a mixture of such compounds, for the production of elastomer dental impression masses.

The following examples explain the invention without restricting it.

In the examples, the following compounds were used:

Siloxane I α,ω-divinyl polydimethyl siloxane with a viscosity at 20° C. of about 1000 mPas Siloxane II Polymethyl hydrogen siloxane with a viscosity at 20° C. of about 200 mPas and an SiH content of 1.8 mmol/g Silicic acid I Pyrogenically produced, highly disperse, hydrophobized silicic acid with a BET surface of 170 m$^2$/g Quartz meal I Quartz meal with an average grain size of 10 μm Catalyst I Platinum catalyst of the Karstedt type, with a content of pure platinum of 1.0%

Surfactant I Non-ionic alkyl-closed fatty alcohol ethoxylate surfactant with a surface tension of 29 mN/m (in deionized water, at 20° C., at a concentration of 1 g/l) and a molecular mass of about 420 g/mol Surfactant II Component of the mixture used according to the invention; non-ionic fluoroalkyl ethoxylate with a surface tension of 19 dyn/cm (in deionized water, at 25° C., at a concentration of 0.01%), an HLB-value of 11.5, and a molecular mass of approximately 725 g/mol Surfactant III Component of the mixture used according to the invention; polyethylene oxide modified polydimethyl siloxane (PEG-8-methicone) with a surface tension of 20.7 dyn/cm (in de-ionized water, at 25° C., at a concentration of 1%), an HLB value of 10.4, and a molecular mass of approximately 620 g/mol Surfactant IV Component of the mixture used according to the invention; polyethylene oxide modified polydimethyl siloxane (PEG-7-methicone) with a surface tension of 20 dyn/cm (in deionized water, at 25° C., at a concentration of 0.1%), an HLB-value of 6.5, and a molecular mass of approximately 600 g/mol Surfactant V $C_{12}$ fatty alcohol ethoxylate with four ethylene oxide units Surfactant VI Nonyl phenyl ethoxylate with five ethylene oxide units Surfactant VII Non-ionic fluorosurfactant Fluorad 4430 with a surface tension of 21 dyn/cm (in deionized water, at 25° C., at a concentration of 0.1%)

Surfactant VIII Siloxane-based Gemini surfactant TEGO® Twin 4000 (Tego Chemie Service Gmbh)

Surfactant IX Polyethylene oxide modified polydimethyl siloxane (CAS 68938-54-5) with a surface tension of 26.6 dyn/cm (in deionized water, at 25° C., at a concentration of 0.1%), with a molecular mass of approximately 10000 g/mol Surfactant X Non-ionic fluorosurfactant with perfluorooctyl sulfonate group (Fluorad FC430) known from DE 43 06 997 A1

Polyether I Component of the mixture used according to the invention; polyethylene glycol dimethyl ether with an average molecular mass of 500 g/mol Polyether II Component of the mixture used according to the invention; α,ω-diallyl polyethylene glycol with an average molecular mass of 2000 g/mol Polyether III Component of the mixture used according to the invention; polyethylene glycol with an average molecular mass of 10000 g/mol

PRODUCTION EXAMPLE A1

Catalyst Mass of an Addition-Crosslinking Two-Component Silicon Dental Impression Material In a vacuum mixer, 50 parts of a siloxane I, 6 parts of a silicic acid I, 43 parts quartz meal I, and one part of a catalyst I were homogeneously mixed for 1.5 hours. A slightly viscous paste (ISO 4823) was obtained. The paste represents a possible catalyst component of the two-component dental impression mass according to the invention.

PRODUCTION EXAMPLE A2

Catalyst Mass of an Addition-Crosslinking Two-Component Silicon Dental Impression Material In a vacuum mixer, 50 parts of a siloxane I, 6 parts of a silicic acid I, 43 parts quartz meal I and one part of a catalyst I were homogeneously mixed for 1.5 hours. 0.4 parts of a surfactant I were added to this mixture, whereby the surfactant was stabilized with hydroxyl anisole, and mixing in a vacuum continued for another 15 minutes, with degasification. A slightly viscous paste (ISO 4823) was obtained. The paste represents a possible catalyst component of the two-component dental impression mass according to the invention.

PRODUCTION EXAMPLE A3

Basic Formulation of a Base Mass of an Addition-Crosslinking Two-Component Silicon Dental Impression Material In a vacuum mixer, 20 parts of a siloxane I, 19 parts of a siloxane II were homogeneously mixed with 5 parts of a silicic acid I and 44 parts quartz meal I for 1.5 hours, and afterwards degassed for 15 minutes. The paste obtained represents a basic formulation of a base component of the two-component dental impression mass according to the invention, which is used in the following examples for the addition of the synergistic surfactant-(polyether) mixture according to the invention.

PRODUCTION EXAMPLE A4

Base Mass of an Addition-Crosslinking Two-Component Silicon Dental Impression Material with a Synergistically Acting Surfactant-Polyether Mixture According to the Invention 93 parts of the basic formulation from Production Example A3 were homogeneously mixed, in a vacuum mixer, with 0.75 parts of a surfactant II, 2.25 parts of a surfactant III, and 4 parts of a polyether I, for 15 minutes, and degassed. A slightly viscous paste (ISO 4823) was obtained. The paste represents a possible base component of the two-component dental impression mass according to the invention.

PRODUCTION EXAMPLE A5

Base Mass of an Addition-Crosslinking Two-Component Silicon Dental Impression Material with a Synergistically Acting Surfactant-(Polyether) Mixture According to the Invention 87 parts of the basic formulation from Production Example A3 were homogeneously mixed, in a vacuum mixer, with 0.75 parts of a surfactant II, 2.25 parts of a surfactant III, and 10 parts of a polyether II, for 15 minutes, and degassed. A slightly viscous paste (ISO 4823) was obtained. The paste represents a possible base component of the two-component dental impression mass according to the invention.

PRODUCTION EXAMPLE A6

Base Mass of an Addition-Crosslinking Two-Component Silicon Dental Impression Material with a Synergistically Acting Surfactant Mixture According to the Invention 97 parts of the basic formulation from Production Example A3 were homogeneously mixed, in a vacuum mixer, with 0.75 parts of a surfactant II and 2.25 parts of a surfactant III, for 15 minutes, and degassed. A slightly viscous paste (ISO 4823) was obtained. The paste represents a possible base component of the two-component dental impression mass according to the invention.

PRODUCTION EXAMPLE AA6

Base Mass of an Addition-Crosslinking Two-Component Silicon Dental Impression Material with a Synergistically Acting Surfactant-Polyol Mixture According to the Invention 96 parts of the basic formulation from Production Example A3 were homogeneously mixed, in a vacuum mixer, with 0.75 parts of a surfactant II, 2.25 parts of a surfactant III, and 1.00 parts glycerin, for 15 minutes, and degassed. A slightly viscous paste (ISO 4823) was obtained. The paste represents a possible base component of the two-component dental impression mass according to the invention.

PRODUCTION EXAMPLE AAA6

Base Mass of an Addition-Crosslinking Two-Component Silicon Dental Impression Material with a Synergistically Acting Surfactant-Polyol-Polyether Mixture According to the Invention 94.5 parts of the basic formulation from Production Example A3 were homogeneously mixed, in a vacuum mixer, with 0.75 parts of a surfactant II, 2.25 parts of a surfactant III, 1.50 parts glycerin, and 1.00 parts $\alpha,\omega$-diallyl polyethylene glycol with an average molecular mass of 1200 g/mol, for 15 minutes, and degassed. A slightly viscous paste (ISO 4823) was obtained. The paste represents a possible base component of the two-component dental impression mass according to the invention.

PRODUCTION EXAMPLE A7

Base Mass of an Addition-Crosslinking Two-Component Silicon Dental Impression Material with a Synergistically Acting Surfactant Mixture According to the Invention 97 parts of the basic formulation from Production Example A3 were homogeneously mixed, in a vacuum mixer, with 1.5 parts of a surfactant II and 1.5 parts of a surfactant III, four 15 minutes, and degassed. A slightly viscous paste (ISO 4823) was obtained. The paste represents a possible base component of the two-component dental impression mass according to the invention.

PRODUCTION EXAMPLE A8

Base Mass of an Addition-Crosslinking Two-Component Silicon Dental Impression Material with Synergistically Acting Surfactant Mixture According to the Invention 97 parts of the basic formulation from Production Example A3 were homogeneously mixed, in a vacuum mixer, with 0.75 parts of a surfactant II and 2.25 parts of a surfactant IV, for 15 minutes, and degassed. A slightly viscous paste (ISO 4823) was obtained. The paste represents a possible base component of the two-component dental impression mass according to the invention.

PRODUCTION EXAMPLE A9

Base Mass of an Addition-Crosslinking Two-Component Silicon Dental Impression Material with a Synergistically Acting Surfactant-Polyether Mixture 94 parts of the basic formulation from Production Example A3 were homogeneously mixed, in a vacuum mixer, with 0.75 parts of a surfactant II, 2.25 parts of a surfactant III, and 3 parts of a polyether III, for 15 minutes, and degassed. A slightly viscous paste (ISO 4823) was obtained. The paste represents a possible base component of the two-component dental impression mass according to the invention.

EXAMPLE A1

Addition-Crosslinking Two-Component Silicon Dental Impression Mass with Synergistically Acting Surfactant-Polyether Mixture 50 parts of the catalyst component described in Production Example A1 and 50 parts of the base component described in Production Example A4 were pressed out of a cartridge (Mixpac) and homogeneously mixed using a static mixer (Mixpac).

Result 1A: A slightly viscous dental impression mass (ISO 4823) was obtained, whose contact angles at different points in time within the processing time were investigated (see Tables 1A and 1B). It turned out that in every phase during the processing time of the impression mass, a water droplet applied to the surface of the impression mass spreads completely within one to ten seconds, and wets it. Such a material is excellently suited to flow onto the regions of which an impression is to be taken, in the patient's mouth, despite the effect of damp tooth substance and saliva, and to image them precisely in the impression. In comparison with commercially available addition-crosslinking silicon dental impression material not provided with the synergistic surfactant mixture according to the invention (Comparison Examples A9, A10), the difference in the behavior of a water droplet applied to the impression material surface becomes clear. While a water droplet applied to the surface of the impression mass spreads completely within one to ten seconds and wets it when the synergistic surfactant mixture is added, in every phase during the processing time of the impression mass, in the case of the non-modified commercial product, the water droplets applied to the surface of the impression mass do not spread and do not wet it sufficiently. The material according to the invention is excellently suited, in contrast to commercially available dental impression materials, to flow onto the regions of which an impression is to be taken, in the patient's mouth, despite the effect of damp tooth substance, saliva, and blood, and to image them precisely in the impression.

EXAMPLE A2

Addition-Crosslinking Two-Component Silicon Dental Impression Mass with Synergistically Acting Surfactant-Polyether Mixture 50 parts of the catalyst component described in Production Example A2 and 50 parts of the base component described in Production Example A4 were pressed out of a cartridge (Mixpac) and homogeneously mixed using a static mixer (Mixpac).

Result 2A: like Result 1A

EXAMPLE A3

Addition-Crosslinking Two-Component Silicon Dental Impression Mass with Synergistically Acting Surfactant-Polyether Mixture 50 parts of the catalyst component described in Production Example A2 and 50 parts of the base component described in Production Example A5 were pressed out of a cartridge (Mixpac) and homogeneously mixed using a static mixer (Mixpac).

Result 3A: like Result 1A

EXAMPLE A4

Addition-Crosslinking Two-Component Silicon Dental Impression Mass with Synergistically Acting Surfactant Mixture 50 parts of the catalyst component described in Production Example A2 and 50 parts of the base component described in Production Example A6 were pressed out of a cartridge (Mixpac) and homogeneously mixed using a static mixer (Mixpac).

Result 4A: like Result 1A

EXAMPLE AA4

Addition-Crosslinking Two-Component Silicon Dental Impression Mass with Synergistically Acting Surfactant-Polyol Mixture 50 parts of the catalyst component described in Production Example A2 and 50 parts of the base component described in Production Example AA6 were pressed out of a cartridge (Mixpac) and homogeneously mixed using a static mixer (Mixpac).

Result 4AA: like Result 1A

EXAMPLE AAA4

Addition-Crosslinking Two-Component Silicon Dental Impression Mass with Synergistically Acting Surfactant-Polyol-Polyether Mixture 50 parts of the catalyst component described in Production Example A2 and 50 parts of the base component described in Production Example AAA6 were pressed out of a cartridge (Mixpac) and homogeneously mixed using a static mixer (Mixpac).

Result 4AAA: like Result 1A

EXAMPLE A5

Addition-Crosslinking Two-Component Silicon Dental Impression Mass with Synergistically Acting Surfactant Mixture 50 parts of the catalyst component described in Production Example A2 and 50 parts of the base component described in Production Example A7 were pressed out of a cartridge (Mixpac) and homogeneously mixed using a static mixer (Mixpac).

Result 5A: like Result 1A

EXAMPLE A6

Addition-Crosslinking Two-Component Silicon Dental Impression Mass with Synergistically Acting Surfactant Mixture 50 parts of the catalyst component described in Production Example A2 and 50 parts of the base component described in Production Example A8 were pressed out of a cartridge (Mixpac) and homogeneously mixed using a static mixer (Mixpac).

Result 6A: like Result 1A

EXAMPLE A7

Addition-Crosslinking Two-Component Silicon Dental Impression Mass with a Synergistically Acting Surfactant-Polyether Mixture 50 parts of the catalyst component described in Production Example A2 and 50 parts of the base component described in Production Example A9 were pressed out of a cartridge (Mixpac) and homogeneously mixed using a static mixer (Mixpac).

Result 7A: like Result 1A

PRODUCTION COMPARISON EXAMPLE A1

Base Component of an Addition-Crosslinking Two-Component Silicon Dental Impression Mass with a Non-Synergistically Acting Surfactant Mixture 97 parts of the basic formulation from Production Example A3 were homogeneously mixed, in a vacuum mixer, with 0.75 parts of a surfactant II and 2.25 parts of a surfactant V, for 15 minutes, and degassed. A slightly viscous paste (ISO 4823) was obtained. The paste represents a base component, not according to the invention, for a two-component dental impression mass.

PRODUCTION COMPARISON EXAMPLE A2

Base Component of an Addition-Crosslinking Two-Component Dental Impression Mass with a Non-Synergistically Acting Surfactant Mixture 97 parts of the basic formulation from Production Example A3 were homogeneously mixed, in a vacuum mixer, with 0.75 parts of a surfactant II and 2.25 parts of a surfactant VI, for 15 minutes, and degassed. A slightly viscous paste (ISO 4823) was obtained. The paste represents a base component, not according to the invention, for a two-component dental impression mass.

PRODUCTION COMPARISON EXAMPLE A3

Base Component of an Addition-Crosslinking Two-Component Dental Impression Mass Exclusively with the Fluorosurfactant from Examples A1 to A7, i.e. not in a Mixture with Silicon Surfactant 98.5 parts of the basic formulation from Production Example A3 were homogeneously mixed, in a vacuum mixer, with 1.50 parts of a surfactant II, for 15 minutes, and degassed. A slightly viscous paste (ISO 4823) was obtained. The paste represents a base component, not according to the invention, for a two-component-dental impression mass.

PRODUCTION COMPARISON EXAMPLE A4

Base Component of an Addition-Crosslinking Two-Component Dental Impression Mass Exclusively with the Fluorosurfactant from Examples A1 to A7, i.e. not in a Mixture with Silicon Surfactant or Silicon Surfactant and Polyether Polymer 97 parts of the basic formulation from Production Example A3 were homogeneously mixed, in a vacuum mixer, with 3 parts of a surfactant II, for 15 minutes, and degassed. A slightly viscous paste (ISO 4823) was obtained. The paste represents a base component, not according to the invention, for a two-component dental impression mass.

PRODUCTION COMPARISON EXAMPLE A5

Base Component of an Addition-Crosslinking Two-Component Dental Impression Mass Exclusively with the Silicon Surfactant from Examples A1 to A5, i.e. not in a Synergistic Mixture with Fluorosurfactant or Fluorosurfactant and Polyether Polymer 97 parts of the basic formulation from Production Example A3 were homogeneously mixed, in a vacuum mixer, with 3 parts of a surfactant III, for 15 minutes, and degassed. A slightly viscous paste (ISO 4823) was obtained. The paste represents a base component, not according to the invention, for a two-component dental impression mass.

PRODUCTION COMPARISON EXAMPLE A6

Base Component of an Addition-Crosslinking Two-Component Dental Impression Mass Exclusively with the Silicon Surfactant from Example A6, i.e. not in a Synergistic Mixture with Fluorosurfactant and Polyether Polymer 97 parts of the basic formulation from Production Example A3 were homogeneously mixed, in a vacuum mixer, with 3 parts of a surfactant IV, for 15 minutes, and degassed. A slightly viscous paste (ISO 4823) was obtained. The paste represents a base component, not according to the invention, for a two-component dental impression mass.

PRODUCTION COMPARISON EXAMPLE A7

Base Component of an Addition-Crosslinking Two-Component Dental Impression Mass with a Surfactant V 97 parts of the basic formulation from Production Example. A3 were homogeneously mixed, in a vacuum mixer, with 3 parts of a surfactant V, for 15 minutes, and degassed. A slightly viscous paste (ISO 4823) was obtained.

The paste represents a base component, not according to the invention, for a two-component-dental impression mass.

PRODUCTION COMPARISON EXAMPLE A8

Base Component of an Addition-Crosslinking Two-Component Dental Impression Mass with a Surfactant VI 97 parts of the basic formulation from Production Example A3 were homogeneously mixed, in a vacuum mixer, with 3 parts of a surfactant VI, for 15 minutes, and degassed. A slightly viscous paste (ISO 4823) was obtained. The paste represents a base component, not according to the invention, for a two-component dental impression mass.

PRODUCTION COMPARISON EXAMPLE A9

Base Component of an Addition-Crosslinking Two-Component Silicon Dental Impression Mass with a Non-Synergistically Acting Surfactant Mixture of the Best Silicon Surfactant (Run 2) and Fluorosurfactant (Run 11) from Example 1 of U.S. Pat. No. 4,657,959

99 parts of the base component from Example 1, run 2, of U.S. Pat. No. 4,657,959 were homogeneously mixed, in a vacuum mixer, with 1 part of a surfactant VII, for 15 minutes, and degassed. A slightly viscous paste (ISO 4823) was obtained. The paste represents a base component, not according to the invention, for a two-component dental impression mass.

PRODUCTION COMPARISON EXAMPLE A10

Base Component of an Addition-Crosslinking Two-Component Silicon Dental Impression Mass with a Non-Synergistically Acting Surfactant Mixture of the Best Silicon Surfactant (Run 2) and Fluorosurfactant (Run 11) from Example 1 of U.S. Pat. No. 4,657,959

97 parts of the base component from Example 1, run 2 of U.S. Pat. No. 4,657,959 were homogeneously mixed, in a vacuum mixer, with 2 parts of a surfactant VII and one part of a surfactant IV, for 15 minutes, and degassed. A slightly viscous paste (ISO 4823) was obtained. The paste represents a base component, not according to the invention, for a two-component dental impression mass.

PRODUCTION COMPARISON EXAMPLE A11

Base Component of an Addition-Crosslinking Two-Component Silicon Dental Impression Mass with a Non-Synergistically Acting Surfactant Mixture 97 parts of the basic formulation from Production Example A3 were homogeneously mixed, in a vacuum mixer, with 0.75 parts of a surfactant II and 2.25 parts of a surfactant IX, for 15 minutes, and degassed. A slightly viscous paste (ISO 4823) was obtained. The paste represents a base component, not according to the invention, for a two-component dental impression mass.

PRODUCTION COMPARISON EXAMPLE A12

Base Component of an Addition-Crosslinking Two-Component Silicon Dental Impression Mass with a Non-Synergistically Acting Surfactant Mixture 97 parts of the basic formulation from Production Example A3 were homogeneously mixed, in a vacuum mixer, with 0.75 parts of a surfactant II and 2.25 parts of the surfactant VIII, for 15 minutes, and degassed. A slightly viscous paste (ISO 4823) was obtained. The paste represents a base component, not according to the invention, for a two-component dental impression mass.

PRODUCTION COMPARISON EXAMPLE A13

Base Mass of an Addition-Crosslinking Two-Component Silicon Dental Impression Material with a Non-Synergistically Acting Surfactant-Polyether Mixture 93 parts of the basic formulation from Production Example A3 were homogeneously mixed, in a vacuum mixer, with 0.75 parts of a surfactant X, 2.25 parts of a surfactant III, and 4 parts of a polyether III, for 15 minutes, and degassed. A slightly viscous paste (ISO 4823) was obtained. The paste represents a possible base component of a two-component dental impression mass not according to the invention.

COMPARISON EXAMPLE A1

Addition-Crosslinking Two-Component Silicon Dental Impression Mass with a Surfactant Mixture that does not Act Synergistically 50 parts of the catalyst component described in Production Example A2 and 50 parts of the base component described in Production Comparison Example A1 were pressed out of a cartridge (Mixpac) and homogeneously mixed, using a static mixer (Mixpac).

Result 8A: A slightly viscous dental impression mass (ISO 4823) was obtained, whose contact angles at different points in time within the processing time were investigated (see Tables 1A and 1B). It turned out that a contact angle of <10° was not reached in any phase during the processing time of the impression mass, within the measurement time of 30 seconds after application of the water droplet. The applied water droplets do not spread on the surface of the impression mass and do not wet it sufficiently. The equilibrium contact angles between 40 and 120 s material age (after the start of mixing the catalyst component and the base component) were between 38 and 44° 10 seconds after application of the water droplet. This comparison example shows that not just any combination of surfactants leads to a synergistic effect.

COMPARISON EXAMPLE A2

Addition-Crosslinking Two-Component Silicon Dental Impression Mass with a Surfactant Mixture that does not Act Synergistically 50 parts of the catalyst component described in Production Example A2 and 50 parts of the base component described in Production Comparison Example A2 were pressed out of a cartridge (Mixpac) and homogeneously mixed, using a static mixer (Mixpac).

Result 9A: A slightly viscous dental impression mass (ISO 4823) was obtained, which behaved as described in Result 8A. The equilibrium contact angles between 40 and 120 s material age (after the start of mixing the catalyst component and the base component) were between 65 and 75° 10 seconds after application of the water droplet. This comparison example shows that not just any combination of surfactants leads to a synergistic effect.

COMPARISON EXAMPLE A3

Addition-Crosslinking Two-Component Silicon Dental Impression Mass Exclusively with the Fluorosurfactant from Examples A1 to A7, i.e. not in a Mixture with Silicon Surfactant 50 parts of the catalyst component described in Production Example A2 and 50 parts of the base component described in Production Comparison Example A3 were pressed out of a cartridge (Mixpac) and homogeneously mixed, using a static mixer (Mixpac).

Result 10A: A slightly viscous dental impression mass (ISO 4823) was obtained, which behaved as described in Result 8A. The equilibrium contact angles between 40 and 120 s material age (after the start of mixing the catalyst component and the base component) were between 60 and 72° 10 seconds after application of the water droplet. This comparison example shows that the same fluorosurfactant that was used in Examples A1 to A7 in the synergistic surfactant mixture according to the invention by itself does not lead to the effect according to the invention, of spontaneous spreading of a water droplet applied to the surface of the dental impression material.

COMPARISON EXAMPLE A4

Addition-Crosslinking Two-Component Silicon Dental Impression Mass Exclusively with the Fluorosurfactant from Examples A1 to A7, i.e. not in a Mixture with Silicon Surfactant or Silicon Surfactant and Polyether Polymer 50 parts of the catalyst component described in Production Example A2 and 50 parts of the base component described in Production Comparison Example A4 were pressed out of a cartridge (Mixpac) and homogeneously mixed, using a static mixer (Mixpac).

Result 11A: A slightly viscous dental impression mass (ISO 4823) was obtained, which behaved as described in Result 8A. The equilibrium contact angles between 40 and 120 s material age (after the start of mixing the catalyst component and the base component) were between 44 and 66° 10 seconds after application of the water droplet. This comparison example shows that the same fluorosurfactant that was used in Examples A1 to A7 in the synergistic surfactant-(polyether) mixture according to the invention by itself does not lead to the effect according to the invention of spontaneous spreading of a water droplet applied to the surface of the dental impression material.

COMPARISON EXAMPLE A5

Addition-Crosslinking Two-Component Silicon Dental Impression Mass Exclusively with the Silicon Surfactant from Examples A1 to A5, i.e. not in the Synergistic Mixture with Fluorosurfactant or Fluorosurfactant and Polyether Polymer 50 parts of the catalyst component described in Production Example A2 and 50 parts of the base component described in Production Comparison Example A5 were pressed out of a cartridge (Mixpac) and homogeneously mixed, using a static mixer (Mixpac).

Result 12A: A slightly viscous dental impression mass (ISO 4823) was obtained, which behaved as described in Result 8A. The equilibrium contact angles between 40 and 120 s material age (after the start of mixing the catalyst component and the base component) were between 42 and 45° 10 seconds after application of the water droplet. This comparison example shows that the same silicon surfactant that was used in Examples A1 to A5 in the synergistic surfactant-(polyether) mixture according to the invention by itself does not lead to the effect according to the invention, of spontaneous spreading of a water droplet applied to the surface of the dental impression material.

COMPARISON EXAMPLE A6

Addition-Crosslinking Two-Component-Silicon-Dental Impression Mass Exclusively with the Silicon Surfactant from Example A6, i.e. not in the Synergistic Mixture with Fluorosurfactant and Polyether Polymer 50 parts of the catalyst component described in Production Example A2 and 50 parts of the base component described in Production Comparison Example A6 were pressed out of a cartridge (Mixpac) and homogeneously mixed, using a static mixer (Mixpac).

Result 13A: A slightly viscous dental impression mass (ISO 4823) was obtained, which behaved as described in Result 8A. The equilibrium contact angles between 40 and 120 s material age (after the start of mixing the catalyst component and the base component) were between 33 and 42° 10 seconds after application of the water droplet. This comparison example shows that the same silicon surfactant that was used in Example A6 in the synergistic surfactant-polyether mixture according to the invention by itself does not lead to the effect according to the invention, of spontaneous spreading of a water droplet applied to the surface of the dental impression material.

COMPARISON EXAMPLE A7

Addition-Crosslinking Two-Component Silicon Dental Impression Mass with a Surfactant V 50 parts of the catalyst component described in Production Example A2 and 50 parts of the base component described in Production Comparison Example A7 were pressed out of a cartridge (Mixpac) and homogeneously mixed, using a static mixer (Mixpac).

Result 14A: A slightly viscous dental impression mass (ISO 4823) was obtained, which behaved as described in Result 8A. The equilibrium contact angles between 40 and 120 s material age (after the start of mixing the catalyst component and the base component) were between 46 and 58° 10 seconds after application of the water droplet. This comparison example shows that the use of a fatty alcohol ethoxylate surfactant according to the state of the art does not lead to the effect according to the invention, of spontaneous spreading of a water droplet applied to the surface of the dental impression material.

COMPARISON EXAMPLE A8

Addition-Crosslinking Two-Component Silicon Dental Impression Mass with a Surfactant VI 50 parts of the catalyst component described in Production Example A2 and 50 parts of the base component described in Production Comparison Example A8 were pressed out of a cartridge (Mixpac) and homogeneously mixed, using a static mixer (Mixpac).

Result 15A: A slightly viscous dental impression mass (ISO 4823) was obtained, which behaved as described in Result 8A. The equilibrium contact angles between 40 and 120 s material age (after the start of mixing the catalyst component and the base component) were between 68 and 78° 10 seconds after application of the water droplet. This comparison example shows that the use of a nonyl phenyl ethoxylate surfactant according to the state of the art does not lead to the effect according to the invention, of spontaneous spreading of a water droplet applied to the surface of the dental impression material.

COMPARISON EXAMPLE A9

Addition-Crosslinking Two-Component Silicon Dental Impression Mass with a Silicon Surfactant According to the State of the Art 50 parts of the catalyst paste and 50 parts of the base paste of an addition-crosslinking silicon dental impression material according to WO-A-2004/58196 (commercial product aquasil ultra LV, Detrey Dentsply, Lot 030 923) were pressed out of a cartridge (Mixpac) and homogeneously mixed, using a static mixer (Mixpac).

Result 16A: A slightly viscous dental impression mass (ISO 4823) was obtained, which behaved as described in Result 8A. The equilibrium contact angles between 40 and 120 s material age (after the start of mixing the catalyst component and the base component) were between 48 and 69° 10 seconds after application of the water droplet. This comparison example shows that dental impression materials according to the state of the art do not have a synergistic contact angle effect.

COMPARISON EXAMPLE A10

Addition-Crosslinking Two-Component Silicon Dental Impression Mass According to the State of the Art An addition-crosslinking silicon dental impression material (commercial product Panasil Contact Plus, Kettenbach GmbH+Co. KG, Lot 05041) was pressed out of a cartridge (Mixpac), according to manufacturer instructions, and homogeneously mixed, using a static mixer (Mixpac).

Result 17A: like Result 8A

The equilibrium contact angles between 40 and 120 s material age (after the start of mixing the catalyst component and the base component) were between 46 and 58° 10 seconds after application of the water droplet. This comparison example shows that addition-crosslinking silicon dental impression materials according to the state of the art do not lead to the effect according to the invention, of spontaneous spreading of a water droplet applied to the surface of the dental impression material.

COMPARISON EXAMPLE A11

Addition-Crosslinking Two-Component Silicon Dental Impression Mass with 1.0% Silicon Surfactant According to U.S. Pat. No. 4,657,959 Table I, Run 2

An addition-crosslinking silicon dental impression material according to the example in Table I, run No. 2, of U.S. Pat. No. 4,657,959, was pressed out of a cartridge (Mixpac) and homogeneously mixed, using a static mixer (Mixpac).

Result 18A: like Result 8A

The equilibrium contact angles between 40 and 120 s material age (after the start of mixing the catalyst component and the base component) were between 33 and 42° 10 seconds after application of the water droplet. This comparison example shows that when using the measurement method of the present invention, the dental impression materials according to U.S. Pat. No. 4,657,959 no contact angles <10° and no spreading of water on the surface is achieved.

COMPARISON EXAMPLE A12

Addition-Crosslinking Two-Component Silicon Dental Impression Mass with 0.75% Silicon Surfactant According to U.S. Pat. No. 4,657,959 Table Iv, Run No. 4

An addition-crosslinking silicon dental impression material according to the example in Table IV, run No. 4, of U.S. Pat. No. 4,657,959, was pressed out of a cartridge (Mixpac) and homogeneously mixed, using a static mixer (Mixpac).

Result 19A: like Result 18A

COMPARISON EXAMPLE A13

Addition-Crosslinking Two-Component Silicon Dental Impression Mass with 1.0% Silicon Surfactant According to U.S. Pat. No. 4,657,959 Table Iv, Run 5

An addition-crosslinking silicon dental impression material according to the example in Table IV, run 5 of U.S. Pat. No. 4,657,959 was pressed out of a cartridge (Mixpac) and homogeneously mixed, using a static mixer (Mixpac).

Result 20A: like Result 18A

COMPARISON EXAMPLE A14

Addition-Crosslinking Two-Component Silicon Dental Impression Mass with 1.0% Fluorosurfactant According to U.S. Pat. No. 4,657,959 Table Iv, Run 11

An addition-crosslinking silicon dental impression material according to the example in Table IV, run 11, of U.S. Pat.

No. 4,657,959, was pressed out of a cartridge (Mixpac) and homogeneously mixed, using a static mixer (Mixpac).

Result 21A: like Result 8A

The equilibrium contact angles between 40 and 120 s material age (after the start of mixing the catalyst component and the base component) were between 79 and 63° 10 seconds after application of the water droplet. This comparison example shows that when using the measurement method of the present invention, the dental impression materials according to U.S. Pat. No. 4,657,959 no contact angles <10° and no spreading of water on the surface is achieved.

COMPARISON EXAMPLE A15

Addition-Crosslinking Two-Component Silicon Dental Impression Mass with a Non-Synergistically Acting Surfactant Mixture of the Best Silicon Surfactant (Run 2) and Fluorosurfactant (Run 11) from Example 1 of U.S. Pat. No. 4,657,959

50 parts of the catalyst component described in U.S. Pat. Nos. 4,657,959 and 50 parts of the base component described in Production Comparison Example A9 were pressed out of a cartridge (Mixpac) and homogeneously mixed, using a static mixer (Mixpac).

Result 22A: like Result 8A

The equilibrium contact angles between 40 and 120 s material age (after the start of mixing the catalyst component and the base component) were between 39 to 50° 10 seconds after application of the water droplet. This comparison example shows that not just any combination of fluorosurfactants and silicon surfactants leads to a synergistic effect. Surprisingly, a synergistic effect was achieved only in surfactant mixtures with specific fluorosurfactants and silicon surfactants. U.S. Pat. No. 4,657,959 does not describe any mixtures of different surfactants. If, as in this comparison example, the best surfactants, in each instance, of the experimental series of the silicon surfactants and the fluorosurfactant of U.S. Pat. No. 4,657,959, are combined, no spreading of water droplets on the surface of the silicon impression material can be achieved.

COMPARISON EXAMPLE A16

Addition-Crosslinking Two-Component Silicon Dental Impression Mass with a Non-Synergistically Acting Surfactant Mixture of the Best Silicon Surfactant (Run 2) and Fluorosurfactant (Run 11) from Example 1 of U.S. Pat. No. 4,657,959

50 parts of the catalyst component described in U.S. Pat. No. 4,657,959 and 50 parts of the base component described in Production Comparison Example A10 were pressed out of a cartridge (Mixpac) and homogeneously mixed, using a static mixer (Mixpac).

Result 23A: like Result 22A

COMPARISON EXAMPLE A17

Addition-Crosslinking Two-Component Silicon Dental Impression Mass with a Surfactant Mixture that does not Act Synergistically 50 parts of the catalyst component described in Production Example A2 and 50 parts of the base component described in Production Comparison Example A11 were pressed out of a cartridge (Mixpac) and homogeneously mixed, using a static mixer (Mixpac).

Result 24A: like Result 8A

The equilibrium contact angles between 40 and 120 s material age (after the start of mixing the catalyst component and the base component) were between 70 to 86° 10 seconds after application of the water droplet. This comparison example shows that not just any combination of fluorosurfactants with silicon surfactants leads to a synergistic effect. Surprisingly, a synergistic effect is achieved only in surfactant mixtures with specific fluorosurfactants and silicon surfactants. If, as in this example, a fluorosurfactant that has synergistic effects in Examples A1 to A7, in combination with suitable silicon surfactants, is combined with other, unsuitable silicon surfactants, no spreading of water droplets on the surface of the silicon impression material can be achieved.

COMPARISON EXAMPLE A18

Addition-Crosslinking Two-Component Silicon Dental Impression Mass with a Surfactant Mixture that does not Act Synergistically 50 parts of the catalyst component described in Production Example A2 and 50 parts of the base component described in Production Comparison Example A12 were pressed out of a cartridge (Mixpac) and homogeneously mixed, using a static mixer (Mixpac).

Result 25A: like Result 8A

The equilibrium contact angles between 40 and 120 s material age (after the start of mixing the catalyst component and the base component) were between 46 to 62° 10 seconds after application of the water droplet. This comparison example shows that not just any combination of fluorosurfactants with silicon surfactants leads to a synergistic effect. Surprisingly, a synergistic effect is achieved only in surfactant mixtures with specific fluorosurfactants and silicon surfactants. If, as in this example, a fluorosurfactant that has synergistic effects in Examples A1 to A7, in combination with suitable silicon surfactants, is combined with a different, unsuitable silicon surfactant, no spreading of water droplets on the surface of the silicon impression material can be achieved.

COMPARISON EXAMPLE A19

Addition-Crosslinking Two-Component Silicon Dental Impression Mass with a Surfactant Mixture that does not Act Synergistically 50 parts of the catalyst component described in Production Example A2 and 50 parts of the base component described in Production Comparison Example A13 were pressed out of a cartridge (Mixpac) and homogeneously mixed, using a static mixer (Mixpac).

Result 26A: like Result 8A

The equilibrium contact angles between 40 and 120 s material age (after the start of mixing the catalyst component and the base component) were between 35 to 50° 10 seconds after application of the water droplet. This comparison example shows that not just any combination of fluorosurfactants with silicon surfactants leads to a synergistic effect. Surprisingly, a synergistic effect is achieved only in surfactant mixtures with specific fluorosurfactants and silicon surfactants. If, as in this example, an unsuitable fluorosurfactant, such as Fluorad FC430, for example, is combined in combination with suitable silicon surfactants, such as surfactant III, for example, no spreading of water droplets on the surface of the silicon impression material can be achieved.

PRODUCTION EXAMPLE B1

Base Mass of a Condensation-Crosslinking Silicon Dental Impression Material with a Synergistically Acting Surfactant Mixture According to the Invention 97 parts of the base mass of the commercial product Lastic 90 fine, Kettenbach GmbH+Co. KG, Lot 20941, were homogeneously mixed, in a vacuum mixer, with 0.5 parts of a surfactant II, 2.50 parts of a surfactant III, for 15 minutes, and degassed. A slightly viscous paste (ISO 4823) was obtained. The paste represents a possible base component of the two-component dental impression mass according to the invention.

PRODUCTION EXAMPLE B2

Base Mass of a Condensation-Crosslinking Silicon Dental Impression Material with a Synergistically Acting Surfactant Mixture According to the Invention 97 parts of the base mass of the commercial product Lastic 90 fine, Kettenbach GmbH+Co. KG, Lot 20941, were homogeneously mixed, in a vacuum mixer, with 1.5 parts of a surfactant II, 1.5 parts of a surfactant III, for 15 minutes, and degassed. A slightly viscous paste (ISO 4823) was obtained. The paste represents a possible base component of the two-component dental impression mass according to the invention.

EXAMPLE B1

Condensation-Crosslinking Silicon Dental Impression Material with a Synergistically Acting Surfactant Mixture According to the Invention 7.7 parts of a catalyst paste of a condensation-crosslinking silicon dental impression material (commercial product Lastic Xtra paste hardener, Kettenbach GmbH+Co. KG, Lot 50861) and 92.3 parts of the base component described in Production Example B1 were homogeneously mixed on a mixing block, using a mixing spatula, for 30 seconds.

Result 1B: A slightly viscous dental impression mass (ISO 4823) was obtained, whose contact angles at different points in time within the processing time were investigated (see Tables 2A and 2B). It turned out that in every phase during the processing time of the impression mass, a water droplet that was applied spreads completely within one to ten seconds, over the surface of the impression mass, and wets it. Such a material is excellently suited to flow onto the regions of which an impression is to be taken, in the patient's mouth, despite the effect of damp tooth substance and saliva, and to image them precisely in the impression. In comparison with commercially available condensation-crosslinking silicon dental impression material not provided with the synergistic surfactant mixture according to the invention (Comparison Example B3), the difference in the behavior of a water droplet applied to the impression material surface becomes clear. While an applied water droplet spreads completely on the surface of the impression mass when the synergistic surfactant mixture is added, in every phase of the processing time of the impression mass, within one to ten seconds, and wets it, in the case of the non-modified commercial product, the applied water droplets do not spread on the surface of the impression mass and do not wet it sufficiently. The material according to the invention is excellently suited, in contrast to commercially available dental impression materials, to flow onto the regions of which an impression is to be taken, in the patient's mouth, despite the effect of damp tooth substance, saliva, and blood, and to image them precisely in the impression.

EXAMPLE B2

Condensation-Crosslinking Silicon Dental Impression Material with a Synergistically Acting Surfactant Mixture According to the Invention 7.7 parts of a catalyst paste of a condensation-crosslinking silicon dental impression material (Commercial product Lastic Xtra paste hardener, Kettenbach GmbH+Co. KG, Lot 50861) and 92.3 parts of the base component described in Production Example B2 were homogeneously mixed on a mixing block, using a mixing spatula, for 30 seconds.

Result 2B: like Result 1B

PRODUCTION COMPARISON EXAMPLE B1

Base Mass of a Condensation-Crosslinking Silicon Dental Impression Material Exclusively with the Silicon Surfactant from Example B1, i.e. not in a Synergistic Mixture with Fluorosurfactant 98.4 parts of the base mass of the commercial product Lastic 90 fine, Kettenbach GmbH+Co. KG, Lot 20941, were homogeneously mixed, in a vacuum mixer, with 1.6 parts of a surfactant III, for 15 minutes, and degassed. A slightly viscous paste (ISO 4823) was obtained. The paste represents a possible base component of the two-component dental impression mass according to the invention.

PRODUCTION COMPARISON EXAMPLE B2

Base Mass of a Condensation-Crosslinking Silicon Dental Impression Material Exclusively with the Fluorosurfactant from Example B1, i.e. not in a Synergistic Mixture with Silicon Surfactant 98.4 parts of the base mass of the commercial product Lastic 90 fine, Kettenbach GmbH+Co. KG, Lot 20941, were homogeneously mixed, in a vacuum mixer, with 1.6 parts of a surfactant II, for 15 minutes, and degassed. A slightly viscous paste (ISO 4823) was obtained. The paste represents a base component, not according to the invention, for a two-component dental impression mass.

COMPARISON EXAMPLE B1

Condensation-Crosslinking Silicon Dental Impression Material Exclusively with the Silicon Surfactant from Example B1, i.e. not in a Synergistic Mixture with Fluorosurfactant 7.7 parts of a catalyst paste of a condensation-crosslinking silicon dental impression material (commercial product Lastic Xtra paste hardener, Kettenbach GmbH+Co. KG; Lot 50861) and 92.3 parts of the base component described in Production Comparison Example B1 were homogeneously mixed on a mixing block, using a mixing spatula, for 30 seconds.

Result 3B: A slightly viscous dental impression mass (ISO 4823) was obtained, the contact angles of which were investigated at different points in time within the processing time (see Tables 1A, 1B, 2A, and 2B). It turned out that a contact angle of <10° is not reached in any phase during the processing time of the impression mass, within the measurement time of 30 seconds after application of the water droplet. The water droplets that are applied do not spread on the surface of the impression mass, and do not wet is sufficiently. The equilibrium contact angles between 40 and 120 s material age (after the start of mixing the catalyst component and the base component) were between 38 and 44° 10 seconds after application of the water droplet. This comparison example shows that not just any combination of surfactants leads to a synergistic effect. The equilibrium contact angles between 40 and 120 s material age (after the start of mixing the catalyst component and the base component) were between 33 and 38° 10 seconds after application of the water droplet. This comparison example shows that the same silicon surfactant that was used in Example B1 in the synergistic surfactant mixture according to the invention by itself does not lead to the effect, according to the invention, of spontaneous spreading of a water droplet applied to the surface of the dental impression material.

COMPARISON EXAMPLE B2

Condensation-Crosslinking Silicon Dental Impression Material Exclusively with the Fluorosurfactant from Example B1, i.e. not in a Synergistic Mixture with Silicon Surfactant 7.7 parts of a catalyst paste of a condensation-crosslinking silicon dental impression material (commercial product Lastic Xtra paste hardener, Kettenbach GmbH+Co. KG, Lot 50861) and 92.3 parts of the base component described in Production Comparison Example B2 were homogeneously mixed on a mixing block using a mixing spatula, for 30 seconds.

Result 4B: like Result 3B

The equilibrium contact angles between 40 and 120 s material age (after the start of mixing the catalyst component and the base component) were between 70 and 85° 10 seconds after application of the water droplet. This comparison example shows that the same silicon surfactant that was used in Example B1 in the synergistic surfactant mixture according to the invention by itself does not lead to the effect according to the invention, of spontaneous spreading of a water droplet applied to the surface of the dental impression material.

COMPARISON EXAMPLE B3

Condensation-Crosslinking Silicon Dental Impression Material According to the State of the Art (Commercial Product)

A condensation-crosslinking silicon dental material (commercial product Lastic 90 fine, Kettenbach GmbH+Co. KG, Lot 20941) is homogeneously mixed on a mixing block, using a mixing spatula, in accordance with manufacturer instructions.

Result 5B: like Result 3B

The equilibrium contact angles between 40 and 120 s material age (after the start of mixing the catalyst component and the base component) were between 69 and 98° 10 seconds after application of the water droplet. This comparison example shows that condensation-crosslinking silicon dental impression materials according to the state of the art do not lead to the effect according to the invention, of spontaneous spreading of a water droplet applied to the surface of the dental impression material.

Production Example C1

Base Mass of a Condensation-Crosslinking Alkoxy Silyl Polyether Dental Impression Material with a Synergistically Acting Surfactant Mixture According to the Invention 97.8 parts of a base mass of a condensation-crosslinking alkoxy silyl polyether dental impression material according to PCT/EP 2005/001470 were homogeneously mixed, in a vacuum mixer, with 0.2 parts of a surfactant II, 2.0 parts of a surfactant III, for 15 minutes, and degassed. A slightly viscous paste (ISO 4823) was obtained. The paste represents a possible base component of the two-component dental impression mass according to the invention.

PRODUCTION EXAMPLE C2

Base Mass of a Condensation-Crosslinking Alkoxy Silyl Polyether Dental Impression Material with a Synergistically Acting Surfactant Mixture According to the Invention 94 parts of a base mass of a condensation-crosslinking alkoxy silyl polyether dental impression material according to EP-A-1,226,808 (commercial product P2-Polyether mono, Heraeus-Kulzer, Lot 190 188) were homogeneously mixed with 5.94 parts of a surfactant II, 0.06 parts of a surfactants III, for 15 minutes, and degassed. A moderately viscous paste (ISO 4823) was obtained. The paste represents a possible base component of the two-component dental impression mass according to the invention.

PRODUCTION EXAMPLE C3

Base Mass of a Condensation-Crosslinking Alkoxy Silyl Polyether Dental Impression Material with a Synergistically Acting Surfactant Mixture According to the Invention 94 parts of a base mass of a condensation-crosslinking alkoxy silyl polyether dental impression material according to EP-A-1,226,808 (commercial product P2-polyether mono, Heraeus-Kulzer, Lot 190 188) were homogeneously mixed with 3.0 parts of a surfactant II, 3.0 parts of a surfactant III, for 15 minutes, and degassed. A moderately viscous paste (ISO 4823) was obtained. The paste represents a possible base component of the two-component dental impression mass according to the invention.

PRODUCTION EXAMPLE CC3

Base Mass of a Condensation-Crosslinking Alkoxy Silyl Polyether Dental Impression Material with a Synergistically Acting Surfactant-Polyol Mixture According to the Invention 94 parts of a base mass of a condensation-crosslinking alkoxy silyl polyether dental impression material according to EP-A-1,226,808 (commercial product P2-Polyether mono, Heraeus-Kulzer, Lot 190 188) were homogeneously mixed with 6.0 parts of a surfactant II and 1.8 parts glycerin, for 15 minutes, and degassed. A moderately viscous paste (ISO 4823) was obtained. The paste represents a possible base component of the two-component dental impression mass according to the invention.

PRODUCTION EXAMPLE CCC3

Base Mass of a Condensation-Crosslinking Alkoxy Silyl Polyether Dental Impression Material with a Synergistically Acting Surfactant-Polyol Mixture According to the Invention 92.2 parts of a base mass of a condensation-crosslinking alkoxy silyl polyether dental impression material according to EP-A-1,226,808 (commercial product P2-polyether mono, Heraeus-Kulzer, Lot 190 188) were homogeneously mixed with 3.0 parts of a surfactant II, 3.0 parts of a surfactant III, and 1.8 parts glycerin, for 15 minutes, and degassed. A moderately viscous paste (ISO 4823) was obtained. The paste represents a possible base component of the two-component dental impression mass according to the invention.

EXAMPLE C1

Condensation-Crosslinking Alkoxy Silyl Polyether Dental Impression Material with a Synergistically Acting Surfactant Mixture According to the Invention 33.3 parts of a catalyst mass of a condensation-crosslinking alkoxy silyl polyether dental impression material according to PCT/EP 2005/001470 and 66.6 parts of the base component described in Production Example C1 were pressed out of a cartridge (Mixpac) and homogeneously mixed, using a static mixer (Mixpac).

Result 1C: A slightly viscous dental impression mass (ISO 4823) was obtained, whose contact angle at different points in time within the processing time was investigated (see Tables 3A and 3B). It turned out that in every phase during the processing time of the impression mass, a water droplet applied to the surface of the impression mass spreads completely within one to ten seconds, and wets it. Such a material is excellently suited to flow onto the regions of which an impression is to be taken, in the patient's mouth, despite the effect of damp tooth substance and saliva, and to precisely image it in the impression. In comparison with commercially available condensation-crosslinking alkoxy silyl polyether dental impression material not provided with the synergistic surfactant mixture according to the invention (Comparison Examples C3 and C4), the difference in the behavior of a water droplet applied to the impression material surface becomes clear. While an applied water droplet spreads completely on the surface of the impression mass, within one to ten seconds, in every phase of the processing time of the impression mass and wets it when the synergistic surfactant mixture is added, in the case of the non-modified commercial product, the water droplets applied do not spread on the surface of the impression mass and do not wet it sufficiently. The material according to the invention, in contrast with commercially available dental impression materials, is excellently suited to flow onto the regions of which an impression is to be taken, in the patient's mouth, despite the effect of damp tooth substance, saliva, and blood, and to image them precisely in the impression.

EXAMPLE C2

Condensation-Crosslinking Alkoxy Silyl Polyether Dental Impression Material with a Synergistically Acting Surfactant Mixture According to the Invention 16.7 parts of a catalyst paste of a condensation-crosslinking alkoxy silyl polyether dental impression material according to EP-A-1,226,808 (commercial product P2-polyether mono, Heraeus-Kulzer, Lot 190 188) and 83.3 parts of the base component described in Production Example C2 were dispensed from tubular bags, using an electrical dispensing device (Plug+Press-Dispenser, Kettenbach GmbH+Co. KG), in each instance, and homogeneously mixed, using a dynamic mixer (Heraeus-Kulzer).

Result 2C: A moderately viscous dental impression mass (ISO 4823) was obtained, which behaved as described in Result 1C.

EXAMPLE C3

Condensation-Crosslinking Alkoxy Silyl Polyether Dental Impression Material with a Synergistically Acting Surfactant Mixture According to the Invention 16.7 parts of a catalyst paste of a condensation-crosslinking alkoxy silyl polyether dental impression material according to EP-A-1,226,808 (commercial product P2-polyether mono, Heraeus-Kulzer, Lot 190 188) and 83.3 parts of the base component described in Production Example C3 were dispensed from tubular bags, using an electrical dispensing device (Plug+Press-Dispenser, Kettenbach GmbH+Co. KG), in each instance, and homogeneously mixed, using a dynamic mixer (Heraeus-Kulzer).

Result 3C: A moderately viscous dental impression mass (ISO 4823) was obtained, which behaved as described in Result 1C.

EXAMPLE CC3

Condensation-Crosslinking Alkoxy Silyl Polyether Dental Impression Material with a Synergistically Acting Surfactant-Polyol Mixture According to the Invention 16.7 parts of a catalyst paste of a condensation-crosslinking alkoxy silyl polyether dental impression material according to EP-A-1,226,808 (commercial product P2-polyether mono, Heraeus-Kulzer, Lot 190 188) and 83.3 parts of the base component described in Production Example CC3 were dispensed from tubular bags, using an electrical dispensing device (Plug+Press-Dispenser, Kettenbach GmbH+Co. KG), in each instance, and homogeneously mixed, using a dynamic mixer (Heraeus-Kulzer).

Result 3CC: A moderately viscous dental impression mass (ISO 4823) was obtained, which behaved as described in Result 1C.

EXAMPLE CCC3

Condensation-Crosslinking Alkoxy Silyl Polyether Dental Impression Material with a Synergistically Acting Surfactant-Polyol Mixture According to the Invention 16.7 parts of a catalyst paste of a condensation-crosslinking alkoxy silyl polyether dental impression material according to EP-A-1,226,808 (commercial product P2-polyether mono, Heraeus-Kulzer, Lot 190 188) and 83.3 parts of the base component described in Production Example CCC3 were dispensed from tubular bags, using an electrical dispensing device (Plug+Press-Dispenser, Kettenbach GmbH+Co. KG), in each instance, and homogeneously mixed, using a dynamic mixer (Heraeus-Kulzer).

Result 3CCC: A moderately viscous dental impression mass (ISO 4823) was obtained, which behaved as described in Result 1C.

PRODUCTION COMPARISON EXAMPLE C1

Base Mass of a Condensation-Crosslinking Alkoxy Silyl Polyether Dental Impression Material Exclusively with the Silicon Surfactant from Example C1, i.e. not in a Synergistic Mixture with Fluorosurfactant 97.8 parts of a base mass of a condensation-crosslinking alkoxy silyl polyether dental impression material according to PCT/EP 2005/001470 were homogeneously mixed, in a vacuum mixer, with 2.2 parts of a surfactant III, for 15 minutes, and degassed. A slightly viscous paste (ISO 4823) was obtained. The paste represents a possible base component of a two-component dental impression mass not according to the invention.

PRODUCTION COMPARISON EXAMPLE C2

Base Mass of a Condensation-Crosslinking Alkoxy Silyl Polyether Dental Impression Material Exclusively with the Fluorosurfactant from Example C2, i.e. not in a Mixture with Silicon Surfactant 97.8 parts of a base mass of a condensation-crosslinking alkoxy silyl polyether dental impression material according to EP-A-1,226,808 (commercial product P2-polyether mono, Heraeus-Kulzer, Lot 190 188) were homogeneously mixed with 2.2 parts of a surfactant II, for 15 minutes, and degassed. A slightly viscous paste (ISO 4823) was obtained. The paste represents a base component, not according to the invention, for a two-component dental impression mass.

COMPARISON EXAMPLE C1

Condensation-Crosslinking Alkoxy Silyl Polyether Dental Impression Material Exclusively with the Silicon Surfactant from Example C1, i.e. not in a Synergistic Mixture with Fluorosurfactant 33.3 parts of a catalyst mass of a condensation-crosslinking alkoxy silyl polyether dental impression material according to PCT/EP 2005/001470 and 66.6 parts of the base component described in Production Comparison Example C1 were pressed out of a cartridge (Mixpac) and homogeneously mixed, using a static mixer (Mixpac).

Result 4C: A slightly viscous dental impression mass (ISO 4823) was obtained, whose contact angle at different points in time within the processing time was investigated (see Tables 3A and 3B). It turned out that a contact angle of <10° was not reached in any phase during the processing time of the impression mass, within the measurement time of 30 seconds after application of the water droplet. The applied water droplets do not spread on the surface of the impression mass and do not wet it sufficiently. The equilibrium contact angles between 40 and 120 s material age (after the start of mixing the catalyst component and the base component) were between 33 and 69° 10 seconds after the water droplet was applied. This comparison example shows that the same silicon surfactant that was used in Example C1 in the synergistic surfactant mixture according to the invention by itself does not lead to the effect according to the invention, of spontaneous spreading of a water droplet applied to the surface of the dental impression material.

COMPARISON EXAMPLE C2

Base Component of a Condensation-Crosslinking Two-Component Alkoxy Silyl Polyether Dental Impression Mass Exclusively with the Fluorosurfactant from Example 9, i.e. not in a Mixture with Silicon Surfactant 16.7 parts of a catalyst paste of a condensation-crosslinking alkoxy silyl polyether dental impression material according to EP-A-1,226,808 (commercial product P2-polyether mono, Heraeus-Kulzer, Lot 190 188) and 83.3 parts of the base component described in Production Comparison Example C2 were dispensed from tubular bags, using an electrical dispensing device (Plug+Press-Dispenser, Kettenbach GmbH+Co. KG), in each instance, and homogeneously mixed, using a dynamic mixer (3M-Espe).

Result 5C: A moderately viscous dental impression mass was obtained, which behaved as described in Result 4C. The equilibrium contact angles between 40 and 120 s material age (after the start of mixing the catalyst component and the base component) were between 38 and 72° 10 seconds after the water droplet was applied. This comparison example shows that the same silicon surfactant that was used in Example C2 in the synergistic surfactant mixture according to the invention by itself does not lead to the effect according to the invention, of spontaneous spreading of a water droplet applied to the surface of the dental impression material.

COMPARISON EXAMPLE C3

Condensation-Crosslinking Alkoxy Silyl Polyether Dental Impression Material According to the State of the Art A condensation-crosslinking alkoxy silyl polyether dental impression material according to PCT/EP 2005/001470 is dispensed from a cartridge (Mixpac) and homogeneously mixed, using a static mixer (Mixpac).

Result 6C: like Result 4C

The equilibrium contact angles between 40 and 120 s material age (after the start of mixing the catalyst component and the base component) were between 34 and 55° 10 seconds after the water droplet was applied. This comparison example shows that condensation-crosslinking alkoxy silyl polyether dental impression materials according to the state of the art do not lead to the effect according to the invention, of spontaneous spreading of a water droplet applied to the surface of the dental impression material.

COMPARISON EXAMPLE C4

Condensation-Crosslinking Alkoxy Silyl Polyether Dental Impression Material According to the State of the Art (Commercial Product)

A condensation-crosslinking alkoxy silyl polyether dental impression material according to EP-A-1,226,808 (commercial product P2 polyether mono, Heraeus Kulzer, Lot 190180) is dispensed from tubular bags in accordance with manufacturer instructions, using an electrical dispensing device (Plug+Press, Kettenbach GmbH+Co. KG), and homogeneously mixed using a dynamic mixer (Heraeus-Kulzer).

Result 7C: A moderately viscous dental impression mass was obtained, which behaved as described in Result 6C. The equilibrium contact angles between 40 and 120 s material age (after the start of mixing the catalyst component and the base component) were between 47 and 53° 10 seconds after the water droplet was applied.

PRODUCTION EXAMPLE D1

Base Mass of an Addition-Crosslinking Aziridino Polyether Dental Impression Material with a Synergistically Acting Surfactant Mixture According to the Invention 98.2 parts of the base mass of an addition-crosslinking aziridino polyether dental impression material according to U.S. Pat. No. 4,353,242 (commercial product Impregum Penta, 3M-Espe, Lot 206352) were homogeneously mixed, in a vacuum mixer, with 1.64 parts of a surfactant II, 0.16 parts of a surfactant III, for 15 minutes, and degassed. A moderately viscous paste (ISO 4823) was obtained. The paste represents a possible base component of the two-component dental impression mass according to the invention.

PRODUCTION EXAMPLE DD1

Base Mass of an Addition-Crosslinking Aziridino Polyether Dental Impression Material with a Synergistically Acting Surfactant Polyol Mixture According to the Invention 98.2 parts of the base mass of an addition-crosslinking aziridino polyether dental impression material according to U.S. Pat. No. 4,353,242 (commercial product Impregum Penta, 3M-Espe, Lot 206352) were homogeneously mixed, in a vacuum mixer, with 1.64 parts of a surfactant II, 0.16 parts of a surfactant III, and 1.80 parts glycerin, for 15 minutes, and degassed. A moderately viscous paste (ISO 4823) was obtained. The paste represents a possible base component of the two-component dental impression mass according to the invention.

PRODUCTION EXAMPLE D2

Base Mass of an Addition-Crosslinking Aziridino Polyether Dental Impression Material with a Synergistically Acting Surfactant Mixture According to the Invention 98.2 parts of the base mass of an addition-crosslinking aziridino polyether dental impression material according to U.S. Pat. No. 4,353,242 (commercial product Impregum Penta, 3M-Espe, Lot 206352) were homogeneously mixed, in a vacuum mixer, with 0.9 parts of a surfactant II, 0.9 parts of a surfactant III, for 15 minutes, and degassed. A moderately viscous paste (ISO 4823) was obtained. The paste represents a possible base component of the two-component dental impression mass according to the invention.

PRODUCTION EXAMPLE D3

Base Mass of an Addition-Crosslinking Aziridino Polyether Dental Impression Material with Surfactant II 98.2 parts of the base mass of an addition-crosslinking aziridino polyether dental impression material according to U.S. Pat. No. 4,353,242 (commercial product Impregum Penta, 3M-Espe, Lot 206352) were homogeneously mixed, in a vacuum mixer, with 1.80 parts of a surfactant II, for 15 minutes, and degassed. A moderately viscous paste (ISO 4823) was obtained. The paste represents a possible base component of the two-component dental impression mass according to the invention.

PRODUCTION EXAMPLE DD3

Base Mass of an Addition-Crosslinking Aziridino Polyether Dental Impression Material with Surfactant II and Glycerin 96.4 parts of the base mass of an addition-crosslinking aziridino polyether dental impression material according to U.S. Pat. No. 4,353,242 (commercial product Impregum Penta, 3M-Espe, Lot 206352) were homogeneously mixed, in a vacuum mixer, with 1.80 parts of a surfactant II and 1.80 parts glycerin, for 15 minutes, and degassed. A moderately viscous paste (ISO 4823) was obtained. The paste represents a possible base component of the two-component dental impression mass according to the invention.

EXAMPLE D1

Addition-Crosslinking Aziridino Polyether Dental Impression Material with a Synergistically Acting Surfactant Mixture According to the Invention 16.7 parts of a catalyst paste of an addition-crosslinking aziridino polyether dental impression material according to U.S. Pat. No. 4,353,242 (commercial product Impregum Penta, 3M-Espe, Lot 206352) and 83.3 parts of the base component described in Production Example D1 were dispensed from tubular bags, in each instance, using an electrical dispensing device (Plug+Press-Dispenser, Kettenbach GmbH+Co. KG), and homogeneously mixed, using a dynamic mixer (3M-Espe).

Result 1D: A moderately viscous dental impression mass (ISO 4823) was obtained, whose contact angle at different points in time within the processing time was investigated (see Tables 4A and 4B). It turned out that in every phase during the processing time of the impression mass, an applied water droplet spreads completely on the surface of the impression mass within one to ten seconds, and wets it. Such a material is excellently suited to flow onto the regions of which an impression is to be taken, in the patient's mouth, despite the effect of damp tooth substance and saliva, and to precisely image them in the impression. In comparison with commercially available addition-crosslinking aziridino polyether dental impression materials not provided with the synergistic surfactant mixture according to the invention (Comparison Example D2), the difference in the behavior of a water droplet applied to the surface of the impression material becomes clear. While an applied water droplet spreads out completely on the surface of the impression mass and wets it, within one to ten seconds, in every phase during the processing time of the impression mass, if the synergistic surfactant mixture is added, in the case of the non-modified commercial product, the applied water droplets do not spread on the surface of the impression mass and do not wet it sufficiently. The material according to the invention, in contrast to the commercially available dental impression materials, is excellently suited to flow onto the regions of which an impression is to be taken, despite the effect of damp tooth substance, saliva, and blood, and to image them precisely in the impression.

EXAMPLE DD1

Addition-Crosslinking Aziridino Polyether Dental Impression Material with a Synergistically Acting Surfactant Polyol Mixture According to the Invention 16.7 parts of a catalyst paste of an addition-crosslinking aziridino polyether dental impression material according to U.S. Pat. No. 4,353,242 (commercial product Impregum Penta, 3M-Espe, Lot 206352) and 83.3 parts of the base component described in Production Example DD1 were dispensed from tubular bags, in each instance, using an electrical dispensing device (Plug+Press-Dispenser, Kettenbach GmbH+Co. KG), and homogeneously mixed, using a dynamic mixer (3M-Espe).
Result 1DD: Like Result 1D

EXAMPLE D2

Addition-Crosslinking Aziridino Polyether Dental Impression Material with a Synergistically Acting Surfactant Mixture According to the Invention 16.7 parts of a catalyst paste of an addition-crosslinking aziridino polyether dental impression material according to U.S. Pat. No. 4,353,242 (commercial product Impregum Penta, 3M-Espe, Lot 206352) and 83.3 parts of the base component described in Production Example D2 were dispensed from tubular bags, in each instance, using an electrical dispensing device (Plug+Press-Dispenser, Kettenbach GmbH+Co. KG), and homogeneously mixed, using a dynamic mixer (3M-Espe).
Result 2D: like Result 1D

EXAMPLE D3

Addition-Crosslinking Aziridino Polyether Dental Impression Material with Surfactant II Used According to the Invention 16.7 parts of a catalyst paste of an addition-crosslinking aziridino polyether dental impression material according to U.S. Pat. No. 4,353,242 (commercial product Impregum Penta, 3M-Espe, Lot 206352) and 83.3 parts of the base component described in Production Example D3 were dispensed from tubular bags, in each instance, using an electrical dispensing device (Plug+Press-Dispenser, Kettenbach GmbH+Co. KG), and homogeneously mixed, using a dynamic mixer (3M-Espe).

Result 3D: like Result 1D

EXAMPLE DD3

Addition-Crosslinking Aziridino Polyether Dental Impression Material with Surfactant II Used According to the Invention and Glycerin 16.7 parts of a catalyst paste of an addition-crosslinking aziridino polyether dental impression material according to U.S. Pat. No. 4,353,242 (commercial product Impregum Penta, 3M-Espe, Lot 206352) and 83.3 parts of the base component described in Production Example DD3 were dispensed from tubular bags, in each instance, using an electrical dispensing device (Plug+Press-Dispenser, Kettenbach GmbH+Co. KG), and homogeneously mixed, using a dynamic mixer (3M-Espe).
Result 3DD: like Result 1D

PRODUCTION COMPARISON EXAMPLE D1

Base Mass of an Addition-Crosslinking Aziridino Polyether Dental Impression Material Exclusively with the Silicon Surfactant from Example D1, i.e. not in a Synergistic Mixture with Fluorosurfactant 98.2 parts of a base mass of an addition-crosslinking aziridino polyether dental impression material according to U.S. Pat. No. 4,353,242 (commercial product Impregum Penta, 3M-Espe, Lot 206352) were homogeneously mixed, in a vacuum mixer, with 1.8 parts of a surfactant III, for 15 minutes, and degassed. A moderately viscous paste (ISO 4823) was obtained. The paste represents a possible base component for a two-component dental impression mass.

PRODUCTION COMPARISON EXAMPLE D2

Base Mass of an Addition-Crosslinking Aziridino Polyether Dental Impression Material with a Non-Synergistically Acting Surfactant Mixture 97 parts of the base mass of an addition-crosslinking aziridino polyether dental impression material according to U.S. Pat. No. 4,353,242 (commercial product Impregum Penta, 3M-Espe, Lot 206352) were homogeneously mixed, in a vacuum mixer, with 0.75 parts of the surfactant VII and 2.25 parts of a surfactant IX, for 15 minutes, and degassed. A moderately viscous paste (ISO 4823) was obtained. The paste represents a possible base component for a two-component dental impression mass.

PRODUCTION COMPARISON EXAMPLE D3

Base Mass of an Addition-Crosslinking Aziridino Polyether Dental Impression Material with a Non-Synergistically Acting Surfactant Mixture 97 parts of the base mass of an addition-crosslinking aziridino polyether dental impression material according to U.S. Pat. No. 4,353,242 (commercial product Impregum Penta, 3M-Espe, Lot 206352) were homogeneously mixed, in a vacuum mixer, with 0.75 parts of the surfactant VII and 2.25 parts of a surfactant IV, for 15 minutes, and degassed. A moderately viscous paste (ISO 4823) was obtained. The paste represents a possible base component for a two-component dental impression mass.

PRODUCTION COMPARISON EXAMPLE D4

Base Mass of an Addition-Crosslinking Aziridino Polyether Dental Impression Material with a Non-Synergistically Acting Surfactant Mixture 98.2 parts of the base mass of an addition-crosslinking aziridino polyether dental impression material according to U.S. Pat. No. 4,353,242 (commercial product Impregum Penta, 3M-Espe, Lot 206352) were homogeneously mixed, in a vacuum mixer, with 0.45 parts of the surfactant X and 1.35 parts of a surfactant III, for 15 minutes, and degassed. A moderately viscous paste (ISO 4823) was obtained. The paste represents a possible base component for a two-component dental impression mass.

COMPARISON EXAMPLE D1

Addition-Crosslinking Aziridino Polyether Dental Impression Material Exclusively with the Silicon Surfactant from Example D1, i.e. not in a Synergistic Mixture with Fluorosurfactant 16.7 parts of a catalyst paste of an addition-crosslinking aziridino polyether dental impression material according to U.S. Pat. No. 4,353,242 (commercial product Impregum Penta, 3M-Espe, Lot 206352) and 83.3 parts of the base component described in Production Comparison Example D1 were dispensed from tubular bags, in each instance, using an electrical dispensing device (Plug+Press-Dispenser, Kettenbach GmbH+Co. KG), and homogeneously mixed, using a dynamic mixer (3M-Espe).

Result 4D: A moderately viscous dental impression mass (ISO 4823) was obtained, whose contact angle at different points in time within the processing time was investigated (see Tables 4A and 4B). It turned out that a contact angle of <10° was not reached in any phase during the processing time of the impression mass, within the measurement time of 30 seconds after application of the water droplet. The water droplets applied to the surface of the impression mass do not spread on it, and do not wet it sufficiently. The equilibrium contact angles between 40 and 120 s material age (after the start of mixing the catalyst component and the base component) were between 19 and 29° 10 seconds after the water droplet was applied. This comparison example shows that the same silicon surfactant that was used in the synergistic surfactant mixture in Example D1 by itself does not lead to the effect according to the invention, of spontaneous spreading of a water droplet applied to the surface of the dental impression material.

COMPARISON EXAMPLE D2

Addition-Crosslinking Aziridino Polyether Dental Impression Material According to the State of the Art (Commercial Product)

An addition-crosslinking aziridino polyether dental impression material according to U.S. Pat. No. 4,353,242 (commercial product Impregum penta, 3M-Espe, Lot 206352) is homogeneously mixed according to manufacturer instructions, using an electrical dispensing device (Plug+Press-Dispenser, Kettenbach GmbH+Co. KG).

Result 5D: A moderately viscous dental impression mass was obtained, which behaved as described in Result 4D. The equilibrium contact angles between 40 and 120 s material age (after the start of mixing the catalyst component and the base component) were between 35 and 39° 10 seconds after the water droplet was applied. This comparison example shows that addition-crosslinking aziridino polyether dental impression materials according to the state of the art do not lead to the effect according to the invention, of spontaneous spreading of a water droplet applied to the surface of the dental impression material.

COMPARISON EXAMPLE D3

Addition-Crosslinking Aziridino Polyether Dental Impression Material with a Non-Synergistically Acting Surfactant Mixture 16.7 parts of a catalyst paste of an addition-crosslinking aziridino polyether dental impression material according to U.S. Pat. No. 4,353,242 (commercial product Impregum Penta, 3M-Espe, Lot 206352) and 83.3 parts of the base component described in Production Comparison Example D2 were dispensed from tubular bags, in each instance, using an electrical dispensing device (Plug+Press-Dispenser, Kettenbach GmbH+Co. KG), and homogeneously mixed using a dynamic mixer (3M-Espe).

Result 6D: A moderately viscous dental impression mass was obtained, which behaved as described in Result 4D. The equilibrium contact angles between 40 and 120 s material age (after the start of mixing the catalyst component and the base component) were between 49 to 56° 10 seconds after the water droplet was applied. This comparison example shows that not just any combination of fluorosurfactants with silicon surfactants leads to a synergistic effect. Surprisingly, a synergistic effect is achieved only in surfactant mixtures with specific fluorosurfactants and silicon surfactants. It is not possible to achieve spreading of water droplets on the surface of the aziridino polyether impression material, using the fluorosurfactant and silicon surfactant used in this example.

COMPARISON EXAMPLE D4

Addition-Crosslinking Aziridino Polyether Dental Impression Material with a Non-Synergistically Acting Surfactant Mixture 16.7 parts of a catalyst paste of an addition-crosslinking aziridino polyether dental impression material according to U.S. Pat. No. 4,353,242 (commercial product Impregum Penta, 3M-Espe, Lot 206352) and 83.3 parts of the base component described in Production Comparison Example D3 were dispensed from tubular bags, in each instance, using an electrical dispensing device (Plug+Press-Dispenser, Kettenbach GmbH+Co. KG), and homogeneously mixed, using a dynamic mixer (3M-Espe).

Result 7D: A moderately viscous dental impression mass was obtained, which behaved as described in Result 4D. The equilibrium contact angles between 40 and 120 s material age (after the start of mixing the catalyst component and the base component) were between 40 to 54° 10 seconds after the water droplet was applied. This comparison example shows not just any combination of fluorosurfactants with silicon surfactants leads to a synergistic effect. Surprisingly, a synergistic effect is achieved only in surfactant mixtures having specific fluorosurfactants and silicon surfactants. It is not possible to achieve spreading of water droplets on the surface of the aziridino polyether impression material, using the fluorosurfactant and silicon surfactant used in this example.

COMPARISON EXAMPLE D5

Addition-Crosslinking Aziridino Polyether Dental Impression Material with a Non-Synergistically Acting Surfactant Mixture 16.7 parts of a catalyst paste of an addition-crosslinking aziridino polyether dental impression material according to U.S. Pat. No. 4,353,242 (commercial product Impregum Penta, 3M-Espe, Lot 206352) and 83.3 parts of the base component described in Production Comparison Example D4 were dispensed from tubular bags, in each instance, using an electrical dispensing device (Plug+Press-Dispenser, Kettenbach GmbH+Co. KG), and homogeneously mixed, using a dynamic mixer (3M-Espe).

Result 8D: A moderately viscous dental impression mass was obtained, which behaved as described in Result 4D. The equilibrium contact angles between 40 and 120 s material age (after the start of mixing the catalyst component and the base component) were between 45 to 66° 10 seconds after the water droplet was applied. This comparison example shows that not just any combination of fluorosurfactants, e.g. fluorad FC430, with silicon surfactants, e.g. surfactant III, leads to a synergistic effect. Surprisingly, a synergistic effect is only achieved in surfactant mixtures with specific fluorosurfactants and silicon surfactants. It is not possible to achieve spreading of water droplets on the surface of the aziridino polyether impression material, using the fluorosurfactant and silicon surfactant used in this example. This example also shows that no conclusions concerning the synergistic effect according to the invention can be drawn from the teaching of DE-A-43 06 997.

The results of the tests are shown in the following tables.

TABLE 1A

Time-dependent contact angle measurements on addition-crosslinking silicones with synergistically acting surfactant (polyether) combinations according to the invention, in comparison with the state of the art[4]

| Examples/<br>Comparison Examples | Material age after start of mixing 40 s [1]<br>Time span until a contact angle of 10° is reached [2] [s] | Material age after start of mixing 60 s [1]<br>Time span until a contact angle of 10° is reached [2] [s] | Material age after start of mixing 90 s [1]<br>Time span until a contact angle of 10° is reached [2] [s] | Material age after start of mixing 120 s [1]<br>Time span until a contact angle of 10° is reached [2] [s] |
|---|---|---|---|---|
| Example A1 according to the invention | 3 | 3 | 3 | 3 |
| Example A2 according to the invention | 3 | 3 | 3 | 3 |
| Example A3 according to the invention | 4 | 4 | 4 | 4 |
| Example A4 according to the invention | 9 | 6 | 6 | 6 |
| Example AA4 according to the invention | 2 | 2 | 1 | 1 |
| Example AAA4 according to the invention | 2 | 2 | 1 | 1 |
| Example A5 according to the invention | 9 | 6 | 4 | 3 |
| Example A6 according to the invention | 10 | 9 | 6 | 6 |
| Example A7 according to the invention | 1 | 1 | 1 | 1 |
| Comparison Example A1 | —[3] | —[3] | —[3] | —[3] |
| Comparison Example A2 | —[3] | —[3] | —[3] | —[3] |
| Comparison Example A3 | —[3] | —[3] | —[3] | —[3] |
| Comparison Example A4 | —[3] | —[3] | —[3] | —[3] |
| Comparison Example A5 | —[3] | —[3] | —[3] | —[3] |
| Comparison Example A6 | —[3] | —[3] | —[3] | —[3] |
| Comparison Example A7 | —[3] | —[3] | —[3] | —[3] |
| Comparison Example A8 | —[3] | —[3] | —[3] | —[3] |
| Comparison Example A9 | —[3] | —[3] | —[3] | —[3] |
| Comparison Example A10 | —[3] | —[3] | —[3] | —[3] |
| Comparison Example A11 | —[3] | —[3] | —[3] | —[3] |
| Comparison Example A12 | —[3] | —[3] | —[3] | —[3] |
| Comparison Example A13 | —[3] | —[3] | —[3] | —[3] |
| Comparison Example A14 | —[3] | —[3] | —[3] | —[3] |
| Comparison Example A15 | —[3] | —[3] | —[3] | —[3] |
| Comparison Example A16 | —[3] | —[3] | —[3] | —[3] |
| Comparison Example A17 | —[3] | —[3] | —[3] | —[3] |
| Comparison Example A18 | —[3] | —[3] | —[3] | —[3] |
| Comparison Example A19 | —[3] | —[3] | —[3] | —[3] |

[1] Point in time of setting water droplet on after the start of mixing the impression material
[2] Droplet size approximately 2 μl, measurement time of droplet max. 30 s
[3] Within the measurement time of 30 s after application of the water droplet, no contact angle <10° is achieved
[4] Measured using a contact angle measurement device G40/G23M from Krüss, at 23° C. ± 1° C., using the "lying droplet" measurement method and a stainless steel sample carrier having a depression of 50 μm

TABLE 1B

Time-dependent contact angle measurement on addition-crosslinking silicones with synergistically acting surfactant (polyether) combinations according to the invention, in comparison with the state of the art[4]

| Examples/Comparison Examples | Material age after start of mixing 40 s [1] Droplet age 10 s contact angle [2] [°] | Material age after start of mixing 60 s [1] Droplet age 10 s contact angle [2] [°] | Material age after start of mixing 90 s [1] Droplet age 10 s contact angle [2] [°] | Material age after start of mixing 120 s [1] Droplet age 10 s contact angle [2] [°] |
|---|---|---|---|---|
| Example A1 according to the invention | <10 | <10 | <10 | <10 |
| Example A2 according to the invention | <10 | <10 | <10 | <10 |
| Example A3 according to the invention | <10 | <10 | <10 | <10 |
| Example A4 according to the invention | <10 | <10 | <10 | <10 |
| Example AA4 according to the invention | <10 | <10 | <10 | <10 |
| Example AAA4 according to the invention | <10 | <10 | <10 | <10 |
| Example A5 according to the invention | <10 | <10 | <10 | <10 |
| Example A6 according to the invention | <10 | <10 | <10 | <10 |
| Example A7 according to the invention | <10 | <10 | <10 | <10 |
| Comparison Example A1 | 38 | 38 | 40 | 44 |
| Comparison Example A2 | 65 | 68 | 74 | 75 |
| Comparison Example A3 | 60 | 63 | 68 | 72 |
| Comparison Example A4 | 44 | 50 | 58 | 66 |
| Comparison Example A5 | 43 | 42 | 44 | 45 |
| Comparison Example A6 | 36 | 33 | 42 | 39 |
| Comparison Example A7 | 47 | 52 | 58 | 46 |
| Comparison Example A8 | 68 | 70 | 75 | 78 |
| Comparison Example A9 | 48 | 54 | 62 | 69 |
| Comparison Example A10 | 46 | 50 | 55 | 58 |
| Comparison Example A11 | 33 | 37 | 40 | 42 |
| Comparison Example A12 | 33 | 37 | 40 | 42 |
| Comparison Example A13 | 33 | 37 | 40 | 42 |
| Comparison Example A14 | 79 | 77 | 75 | 63 |
| Comparison Example A15 | 39 | 42 | 45 | 50 |
| Comparison Example A16 | 39 | 42 | 45 | 50 |
| Comparison Example A17 | 70 | 72 | 76 | 86 |
| Comparison Example A18 | 46 | 54 | 58 | 62 |
| Comparison Example A19 | 49 | 45 | 38 | 49 |

[1] Point in time of setting water droplet on after the start of mixing the impression material
[2] Droplet size approximately 2 μl, measurement time of droplet max. 30 s
[4] Measured using a contact angle measurement device G40/G23M from Krüss, at 23° C. ± 1° C., using the "lying droplet" measurement method and a stainless steel sample carrier having a depression of 50 μm

TABLE 2A

Time-dependent contact angle measurements on condensation-crosslinking silicones with a synergistically acting surfactant combination in comparison with the state of the art[4]

| Examples/Comparison Examples | Material age after start of mixing 40 s [1] Time span until a contact angle of 10° is reached [2] [s] | Material age after start of mixing 60 s [1] Time span until a contact angle of 10° is reached [2] [s] | Material age after start of mixing 90 s [1] Time span until a contact angle of 10° is reached [2] [s] | Material age after start of mixing 120 s [1] Time span until a contact angle of 10° is reached [2] [s] |
|---|---|---|---|---|
| Example B1 according to the invention | <1 | <1 | <1 | <1 |
| Example B2 according to the invention | <1 | <1 | <1 | <1 |
| Comparison Example B1 | —[3] | —[3] | —[3] | —[3] |

TABLE 2A-continued

Time-dependent contact angle measurements on condensation-crosslinking silicones with a synergistically acting surfactant combination in comparison with the state of the art[4]

| Examples/Comparison Examples | Material age after start of mixing 40 s [1] Time span until a contact angle of 10° is reached [2] [s] | Material age after start of mixing 60 s [1] Time span until a contact angle of 10° is reached [2] [s] | Material age after start of mixing 90 s [1] Time span until a contact angle of 10° is reached [2] [s] | Material age after start of mixing 120 s [1] Time span until a contact angle of 10° is reached [2] [s] |
|---|---|---|---|---|
| Comparison Example B2 | —[3] | —[3] | —[3] | —[3] |
| Comparison Example B3 | —[3] | —[3] | —[3] | —[3] |

[1] Point in time of setting water droplet on after the start of mixing the impression material
[2] Droplet size approximately 2 μl, measurement time of droplet max. 30 s
[3] Within the measurement time of 30 s after application of the water droplet, no contact angle <10° is achieved
[4] Measured using a contact angle measurement device G40/G23M from Krüss, at 23° C. ± 1° C., using the "lying droplet" measurement method and a stainless steel sample carrier having a depression of 50 μm

TABLE 2B

Time-dependent contact angle measurements on condensation-crosslinking silicones with a synergistically acting surfactant combination according to the invention, in comparison with the state of the art[4]

| Examples/Comparison Examples | Material age after start of mixing 40 s [1] Droplet age 10 s contact angle [2] [°] | Material age after start of mixing 60 s [1] Droplet age 10 s contact angle [2] [°] | Material age after start of mixing 90 s [1] Droplet age 10 s contact angle [2] [°] | Material age after start of mixing 120 s [1] Droplet age 10 s contact angle [2] [°] |
|---|---|---|---|---|
| Example B1 according to the invention | <10 | <10 | <10 | <10 |
| Example B2 according to the invention | <10 | <10 | <10 | <10 |
| Comparison Example B1 | 33 | 35 | 40 | 38 |
| Comparison Example B2 | 70 | 72 | 85 | 85 |
| Comparison Example B3 | 69 | 89 | 90 | 98 |

[1] Point in time of setting water droplet on after the start of mixing the impression material
[2] Droplet size approximately 2 μl, measurement time of droplet max. 30 s
[4] Measured using a contact angle measurement device G40/G23M from Krüss, at 23° C. ± 1° C., using the "lying droplet" measurement method and a stainless steel sample carrier having a depression of 50 μm

TABLE 3A

Time-dependent contact angle measurements on condensation-crosslinking alkoxy silyl polyethers with a synergistically acting surfactant combination according to the invention, in comparison with the state of the art[4]

| Examples/Comparison Examples | Material age after start of mixing 40 s [1] Time span until a contact angle of 10° is reached [2] [s] | Material age after start of mixing 60 s [1] Time span until a contact angle of 10° is reached [2] [s] | Material age after start of mixing 90 s [1] Time span until a contact angle of 10° is reached [2] [s] | Material age after start of mixing 120 s [1] Time span until a contact angle of 10° is reached [2] [s] |
|---|---|---|---|---|
| Example C1 according to the invention | <1 | <1 | <1 | <1 |
| Example C2 according to the invention | 5 | 3 | 3 | 5 |
| Example C3 according to the invention | <1 | <1 | <1 | <1 |
| Example CC3 according to the invention | 3 | 3 | 3 | 3 |
| Example CCC3 according to the invention | 1 | 1 | 1 | 1 |
| Comparison Example C1 | —[3] | —[3] | —[3] | —[3] |

TABLE 3A-continued

Time-dependent contact angle measurements on condensation-crosslinking alkoxy
silyl polyethers with a synergistically acting surfactant combination according to the
invention, in comparison with the state of the art[4]

| Examples/Comparison Examples | Material age after start of mixing 40 s [1] Time span until a contact angle of 10° is reached [2] [s] | Material age after start of mixing 60 s [1] Time span until a contact angle of 10° is reached [2] [s] | Material age after start of mixing 90 s [1] Time span until a contact angle of 10° is reached [2] [s] | Material age after start of mixing 120 s [1] Time span until a contact angle of 10° is reached [2] [s] |
|---|---|---|---|---|
| Comparison Example C2 | —[3] | —[3] | —[3] | —[3] |
| Comparison Example C3 | —[3] | —[3] | —[3] | —[3] |
| Comparison Example C4 | —[3] | —[3] | —[3] | —[3] |

[1] Point in time of setting water droplet on after the start of mixing the impression material
[2] Droplet size approximately 2 μl, measurement time of droplet max. 30 s
[3] Within the measurement time of 30 s after application of the water droplet, no contact angle <10° is achieved
[4] Measured using a contact angle measurement device G40/G23M from Krüss, at 23° C. ± 1° C., using the "lying droplet" measurement method and a stainless steel sample carrier having a depression of 50 μm

TABLE 3B

Time-dependent contact angle measurements on condensation-crosslinking alkoxy
silyl polyethers with a synergistically acting surfactant combination according to the
invention, in comparison with the state of the art[4]

| Examples/Comparison Examples | Material age after start of mixing 40 s [1] Droplet age 10 s contact angle [2] [°] | Material age after start of mixing 60 s [1] Droplet age 10 s contact angle [2] [°] | Material age after start of mixing 90 s [1] Droplet age 10 s contact angle [2] [°] | Material age after start of mixing 120 s [1] Droplet age 10 s contact angle [2] [°] |
|---|---|---|---|---|
| Example C1 according to the invention | <10 | <10 | <10 | <10 |
| Example C2 according to the invention | <10 | <10 | <10 | <10 |
| Example C3 according to the invention | <10 | <10 | <10 | <10 |
| Example CC3 according to the invention | <10 | <10 | <10 | <10 |
| Example CCC3 according to the invention | <10 | <10 | <10 | <10 |
| Comparison Example C1 | 33 | 48 | 60 | 69 |
| Comparison Example C2 | 38 | 52 | 62 | 72 |
| Comparison Example C3 | 34 | 39 | 50 | 55 |
| Comparison Example C4 | 47 | 49 | 53 | 49 |

[1] Point in time of setting water droplet on after the start of mixing the impression material
[2] Droplet size approximately 2 μl, measurement time of droplet max. 30 s
[3] Within the measurement time of 30 s after application of the water droplet, no contact angle <10° is achieved
[4] Measured using a contact angle measurement device G40/G23M from Krüss, at 23° C. ± 1° C., using the "lying droplet" measurement method and a stainless steel sample carrier having a depression of 50 μm

TABLE 4A

Time-dependent contact angle measurements on addition-crosslinking aziridino
polyethers with a synergistically acting surfactant combination according to the
invention, in comparison with the state of the art[4]

| Examples/Comparison Examples | Material age after start of mixing 40 s [1] Time span until a contact angle of 10° is reached [2] [s] | Material age after start of mixing 60 s [1] Time span until a contact angle of 10° is reached [2] [s] | Material age after start of mixing 90 s [1] Time span until a contact angle of 10° is reached [2] [s] | Material age after start of mixing 120 s [1] Time span until a contact angle of 10° is reached [2] [s] |
|---|---|---|---|---|
| Example D1 according to the invention | <1 | <1 | <1 | <1 |

TABLE 4A-continued

Time-dependent contact angle measurements on addition-crosslinking aziridino polyethers with a synergistically acting surfactant combination according to the invention, in comparison with the state of the art[4]

| Examples/Comparison Examples | Material age after start of mixing 40 s [1] Time span until a contact angle of 10° is reached [2] [s] | Material age after start of mixing 60 s [1] Time span until a contact angle of 10° is reached [2] [s] | Material age after start of mixing 90 s [1] Time span until a contact angle of 10° is reached [2] [s] | Material age after start of mixing 120 s [1] Time span until a contact angle of 10° is reached [2] [s] |
|---|---|---|---|---|
| Example DD1 according to the invention | <1 | <1 | <1 | <1 |
| Example D2 according to the invention | <1 | <1 | <1 | <1 |
| Example D3 according to the invention | <1 | <1 | <1 | <1 |
| Example DD3 according to the invention | <1 | <1 | <1 | <1 |
| Comparison Example D1 | —[3] | —[3] | —[3] | —[3] |
| Comparison Example D2 | —[3] | —[3] | —[3] | —[3] |
| Comparison Example D3 | —[3] | —[3] | —[3] | —[3] |
| Comparison Example D4 | —[3] | —[3] | —[3] | —[3] |
| Comparison Example D5 | —[3] | —[3] | —[3] | —[3] |

[1] Point in time of setting water droplet on after the start of mixing the impression material
[2] Droplet size approximately 2 µl, measurement time of droplet max. 30 s
[3] Within the measurement time of 30 s after application of the water droplet, no contact angle <10° is achieved
[4] Measured using a contact angle measurement device G40/G23M from Krüss, at 23° C. ± 1° C., using the "lying droplet" measurement method and a stainless steel sample carrier having a depression of 50 µm

TABLE 4B

Time-dependent contact angle measurement on addition-crosslinking aziridino polyethers with a synergistically acting surfactant combination according to the invention, in comparison with the state of the art[4]

| Examples/Comparison Examples | Material age after start of mixing 40 s [1] Droplet age 10 s contact angle [2] [°] | Material age after start of mixing 60 s [1] Droplet age 10 s contact angle [2] [°] | Material age after start of mixing 90 s [1] Droplet age 10 s contact angle [2] [°] | Material age after start of mixing 120 s [1] Droplet age 10 s contact angle [2] [°] |
|---|---|---|---|---|
| Example D1 according to the invention | <10 | <10 | <10 | <10 |
| Example DD1 according to the invention | <10 | <10 | <10 | <10 |
| Example D2 according to the invention | <10 | <10 | <10 | <10 |
| Example D3 according to the invention | <10 | <10 | <10 | <10 |
| Example DD3 according to the invention | <10 | <10 | <10 | <10 |
| Comparison Example D1 | 19 | 28 | 29 | 26 |
| Comparison Example D2 | 35 | 37 | 37 | 39 |
| Comparison Example D3 | 52 | 49 | 50 | 56 |
| Comparison Example D4 | 40 | 44 | 50 | 54 |
| Comparison Example D5 | 49 | 49 | 62 | 65 |

[1] Point in time of setting water droplet on after the start of mixing the impression material
[2] Droplet size approximately 2 µl, measurement time of droplet max. 30 s
[3] Within the measurement time of 30 s after application of the water droplet, no contact angle <10° is achieved
[4] Measured using a contact angle measurement device G40/G23M from Krüss, at 23° C. ± 1° C., using the "lying droplet" measurement method and a stainless steel sample carrier having a depression of 50 µm

The invention claimed is:

1. A dental impression mass comprising:
   (A) curable polymers selected from the group consisting of
      (1) organopolysiloxanes that crosslink by means of an addition reaction,
      (2) organopolysiloxanes that crosslink by means of a condensation reaction,
      (3) polyethers containing alkoxysilyl groups that crosslink by means of a condensation reaction,
      (4) polyethers containing aziridino groups that crosslink by means of an addition reaction,
      (5) polyethers containing alkenyl groups that crosslink by means of an addition reaction, (6) polyethers containing ester groups of an ethylene-unsaturated carboxylic acid that crosslink by means of a radical polymerization reaction, and
(7) polyethers that contain polysiloxanes and/or synthetic rubbers and crosslink by means of a ring-opening metathesis reaction, (B) a non-ionic surfactant with a molecular mass of less than 6000 g/mol containing at least one (poly)alkylene oxide group as well as one silicon-containing group, and (C) a non-ionic fluorosurfactant that has
(1) at least one partially fluorinated or perfluorinated hydrocarbon group that is connected with a (poly)alkylene oxide group, a hydrocarbon group, an aliphatic polyhydroxy group, or a heterocyclic group containing nitrogen, by way of an oxygen atom, an amino group, a keto group, a carboxylic acid ester group, a phosphoric acid ester group, a carboxylic acid amide group and/or a phosphoric acid amide group, or
(2) at least one partially fluorinated or perfluorinated hydrocarbon group and at least one amino oxide group, wherein the dental impression mass, 40 seconds after the start of mixing, has a low initial water droplet contact angle of <10°, measured at a droplet age of 10 seconds.

2. Dental impression mass according to claim 1, wherein the water droplet contact angle 40 seconds after the start of mixing assumes the following values: after a droplet age of 0.25 seconds, a water droplet contact angle of <75°, preferably of <40°; after a droplet age of 0.5 seconds, a water droplet contact angle of <55°, preferably <30°; after a droplet age of 1 second, a water droplet contact angle of <35°, preferably <25°; after a droplet age of 2 seconds: a water droplet contact angle of <20°; and after a droplet age of 3 seconds, a water droplet contact angle of <10°.

3. Dental impression mass according to claim 1, wherein the fluorosurfactant is a non-ionic fluorosurfactant having at least one (poly)-alkylene oxide group, which contains at least one partially fluorinated or perfluorinated hydrocarbon group that is connected with the (poly)alkylene oxide group by way of an oxygen atom or an ester group.

4. Dental impression mass according to claim 1, wherein the non-ionic fluorosurfactant is a compound having the Formula I

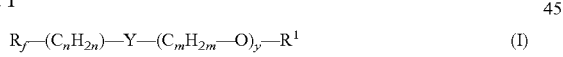  (I)

where $R_f$ is a group having the formula $C_xF_{2x+1}$,
x stands for a whole number from 1 to 30,
n is a whole number from 0 to 30,
Y is $-NR^1-$, $-(O-)_2P(O)(OR^1)$, $-(NR^1-)_2P(O)(OR^1)$, $-(NR^1-)P(O)(OR^1)(O)-$, $-CO-$ or very particularly preferably $-O-$ or $-CO-O-$,
m stands for a whole number from 2 to 6,
y is a whole number from 1 to 60, and
$R^1$ is hydrogen or a monovalent organic group, preferably hydrogen, $C_1$-$C_6$ alkyl or phenyl, whereby m and $R^1$, within a molecule, can assume different meanings, within the framework of the given definition.

5. Dental impression mass according to claim 4, wherein
x stands for a whole number from 2 to 18,
n is a whole number from 1 to 3,
Y is $-O-$,
m stands for 2 or 3, particularly 2,
y is a whole number from 1 to 25, and
$R^1$ is hydrogen or an alkyl group.

6. Dental impression mass according to claim 4, wherein the non-ionic fluorosurfactant is a compound having the Formulas Ia or Ib

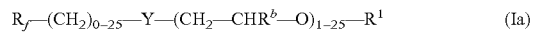  (Ia)

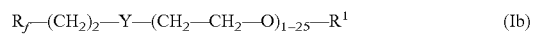  (Ib)

where $R_f$ preferably stands for a group having the formula $C_xF_{2x+1}$ with x=1 to 18, particularly x=4 to 12,
Y is $-O-$,
$R^b$ is $C_1$-$C_6$ alkyl, preferably methyl or ethyl, and
$R^1$ is preferably hydrogen, $C_1$-$C_6$ alkyl, particularly methyl, $C_2$-$C_6$ alkenyl, preferably vinyl, or phenyl.

7. Dental impression mass according to claim 4, wherein the non-ionic fluorosurfactant is a compound having the Formulas Ic or Id

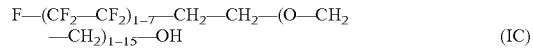  (IC)

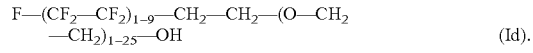  (Id).

8. Dental impression mass according to claim 1, wherein the non-ionic fluorosurfactant is selected from the group of compounds or combinations of two or more of them

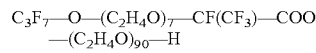

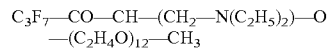

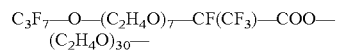

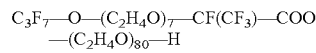

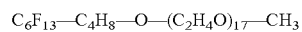

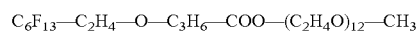

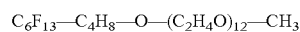

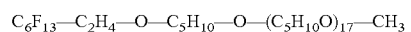

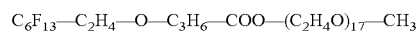

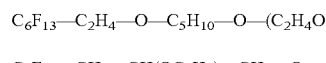

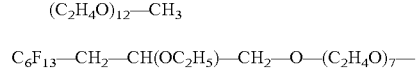

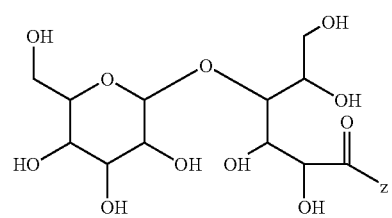

with
Z=$-(NH-CH_2-CO)_p-NH-CH((CH_2)_2-R_f)(CH_2)_8-R)$ or
Z=$-NH-(CH_2)_4-CH((NH-CO-(CH_2)_2-C_8F_{17})(CO-NH-(CH_2)_9-CH_3)$, with p=1 or 2 and R=—CH$_2$, —CH=CH$_2$ and R$_f$=—C$_5$F$_{13}$ or —C$_8$F$_{17}$;

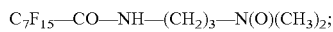

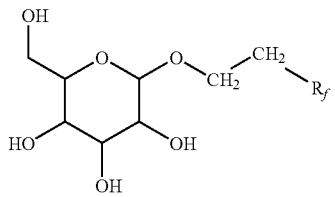

with R$_f$=—C$_6$F$_{13}$ or —C$_8$F$_{17}$;

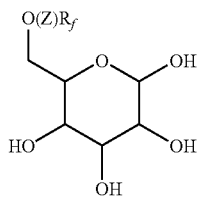

with
Z=(CH$_2$)—CH=CH$_2$ and R$_f$=—C$_4$F$_9$, —C$_6$F$_{13}$ or —C$_8$F$_{17}$ or
Z=—CO—(CH$_2$)$_n$—, n=2 and R$_f$=—C$_8$F$_{17}$ or
Z=—CO—(CH$_2$)$_n$—, n=10 and R$_f$=—C$_4$F$_9$ or —C$_6$F$_{13}$;

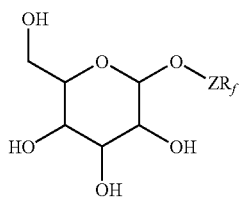

with
Z=(CH$_2$)$_2$ and R$_f$=—C$_5$F$_{13}$ or —C$_8$F$_{17}$ or
Z=—(CH$_2$)$_2$—CH=CH$_2$ and R$_f$=—C$_6$F$_{13}$ or —C$_8$F$_{17}$;

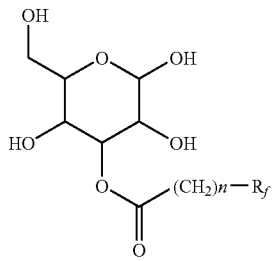

with
n=2 and R$_f$=—C$_8$F$_{17}$ or
n=10 and R$_f$=—C$_4$F$_9$ or —C$_6$F$_{13}$;

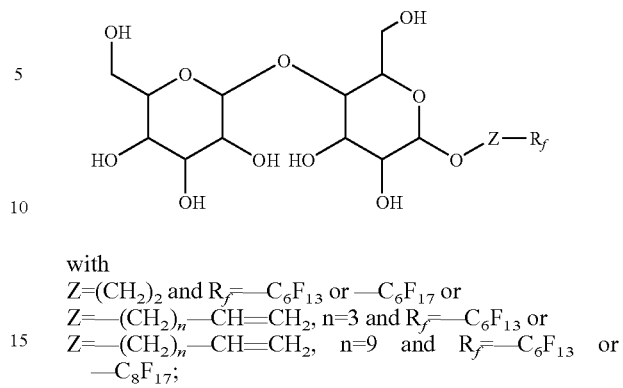

with
Z=(CH$_2$)$_2$ and R$_f$=—C$_6$F$_{13}$ or —C$_6$F$_{17}$ or
Z=—(CH$_2$)$_n$—CH=CH$_2$, n=3 and R$_f$=—C$_6$F$_{13}$ or
Z=—(CH$_2$)$_n$—CH=CH$_2$, n=9 and R$_f$=—C$_6$F$_{13}$ or —C$_8$F$_{17}$;

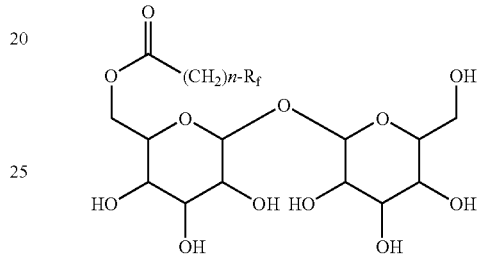

with
n=2 and R$_f$=—C$_8$F$_{17}$ or
n=4 and R$_f$=—C$_6$F$_{13}$ or —C$_8$F$_{17}$,
n=10 and R$_f$=—C$_4$F$_9$ or —C$_6$F$_{13}$;

R$_f$—(CH$_2$)$_n$—OP(O)—(O—(C$_2$H$_4$O)$_p$CH$_3$)$_2$ with
n=2, p=2, 7 and R$_f$=—C$_8$F$_{17}$ or
n=5, p=7, 16 and R$_f$=—C$_8$F$_{17}$;

R$_f$—(CH$_2$)$_n$—OP(O)—(N-morpholino)$_2$ with
n=1 and R$_f$=—C$_7$F$_{15}$ or —C$_9$F$_{19}$ or
n=2 and R$_f$=—C$_4$F$_9$, —C$_6$F$_{13}$, —C$_8$F$_{17}$ or —C$_{10}$F$_{21}$ or
n=5 and R$_f$=—C$_8$F$_{17}$ or
n=11 and R$_f$=—C$_6$F$_{13}$ or —C$_8$F$_{17}$;

(R$_f$—(CH$_2$)$_n$—O)$_2$P(O)—(N-morpholino)

with
n=1 and R$_f$=—C$_9$F$_{19}$ or
n=2 and R$_f$=—C$_6$F$_{13}$ or —C$_9$F$_{17}$;

C$_{10}$H$_{21}$—(CF$_2$)$_{11}$—O—P(O)—(N-morpholino)$_2$

R$_f$—X—O—CH$_2$—CH(OH)—CH(OH)—CH(OH)—CH$_2$—OH with
X=CH=CH—CH$_2$ and R$_f$=—C$_4$F$_9$, —C$_6$F$_{13}$ or —C$_9$F$_{17}$ or
X=(CH$_2$)$_n$—CO, n=2 and R$_f$=—C$_5$F$_{21}$ or —C$_8$F$_{17}$ or
X=(CH$_2$)$_n$—CO, n=10 and R$_f$=—C$_4$F$_9$ or —C$_5$F$_{13}$;

CF$_3$—(CF$_2$)$_3$—CH$_2$—O—(C$_2$H$_4$O)$_4$CH$_3$

CF$_2$—(CF$_2$)$_3$—(CH$_2$)$_3$—N((C$_2$H$_4$O)$_2$H)$_2$

CH$_3$—(C$_2$H$_4$O)$_3$—O—CH$_2$—(CF$_2$)$_{13}$—CH$_2$—O—(C$_2$H$_4$O)$_9$CH$_3$

CF$_3$—(CF$_2$)$_6$—(CH$_2$)$_2$—O—(C$_2$H$_4$O)$_m$H with m=2 to 10;

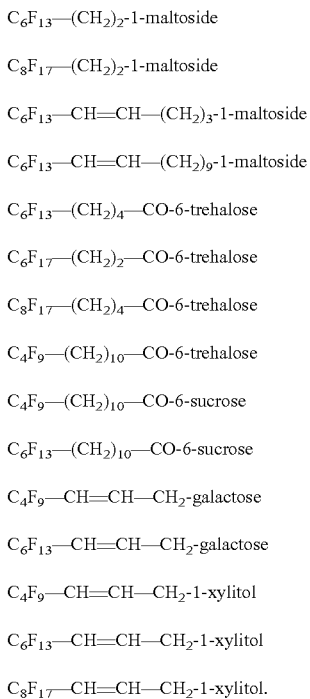

C$_6$F$_{13}$—(CH$_2$)$_2$-1-maltoside

C$_8$F$_{17}$—(CH$_2$)$_2$-1-maltoside

C$_6$F$_{13}$—CH=CH—(CH$_2$)$_3$-1-maltoside

C$_6$F$_{13}$—CH=CH—(CH$_2$)$_9$-1-maltoside

C$_6$F$_{13}$—(CH$_2$)$_4$—CO-6-trehalose

C$_6$F$_{17}$—(CH$_2$)$_2$—CO-6-trehalose

C$_8$F$_{17}$—(CH$_2$)$_4$—CO-6-trehalose

C$_4$F$_9$—(CH$_2$)$_{10}$—CO-6-trehalose

C$_4$F$_9$—(CH$_2$)$_{10}$—CO-6-sucrose

C$_6$F$_{13}$—(CH$_2$)$_{10}$—CO-6-sucrose

C$_4$F$_9$—CH=CH—CH$_2$-galactose

C$_6$F$_{13}$—CH=CH—CH$_2$-galactose

C$_4$F$_9$—CH=CH—CH$_2$-1-xylitol

C$_6$F$_{13}$—CH=CH—CH$_2$-1-xylitol

C$_8$F$_{17}$—CH=CH—CH$_2$-1-xylitol.

9. Dental impression mass according to claim 1, wherein the non-ionic surfactant containing at least one (poly)alkylene oxide group as well as one silicon-containing group possesses a molecular mass of less than 4000 g/mol, particularly of 350 to 2000 g/mol.

10. Dental impression mass according to claim 1, wherein the non-ionic surfactant is an organosiloxane surfactant having the Formula II and/or having the Formula III, or an organocarbosilane surfactant having the Formula IV, V and/or having the Formula VI

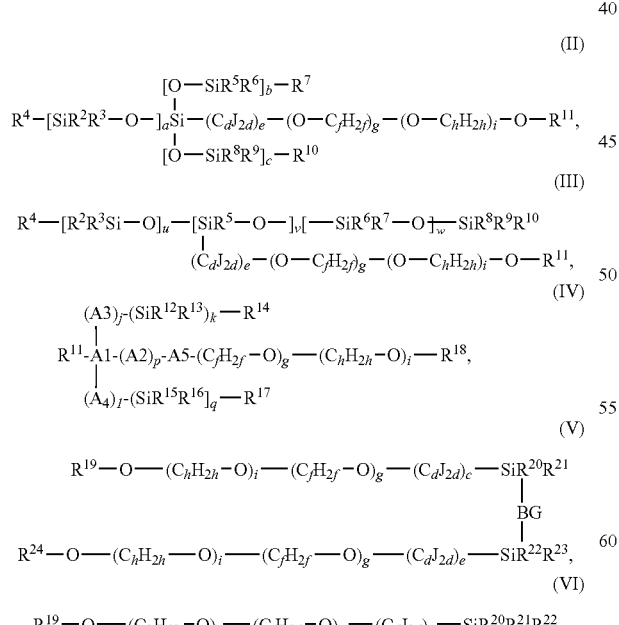

where $R^2$, $R^3$, $R^4$, $R^5$, $R^6$, $R^7$, $R^8$, $R^9$ and $R^{10}$, independent of one another, stand for hydrogen, alkyl, alkyloxy, alkenyl, alkenyloxy, alkynyl, alkynyloxy, aryl, aryloxy, aralkyl, aralkyloxy, alkylaryl and/or alkylaryloxy, which, if necessary, are partially or completely fluorinated, preferably alkyl or alkenyl and particularly $C_1$-$C_6$-alkyl, a, b, c and w, independent of one another, stand for whole numbers from 0 to 100, preferably 0 to 75, particularly 0 to 35, and very particularly preferably 0 to 15, v stands for a whole number from 1 to 100, preferably 1 to 15, and very particularly preferably 1 to 6, whereby the sum of a, b and c amounts to between 1 and 300, preferably 1 to 50, particularly 1 to 10, and very particularly preferably 1 to 3, and the sum of v and w amounts to between 1 and 200, preferably 2 to 90, u is 0 or 1, d is a whole number from 1 to 10, preferably 1 to 6, and particularly 1 to 3, J stands for hydrogen or fluorine, preferably hydrogen, e is 0 or 1, f and h, independent of one another, stand for whole numbers from 2 to 6, g and i, independent of one another, are whole numbers from 0 to 30, preferably 0 to 15, whereby the sum of g and i stands for 1 to 60, preferably 2 to 30, particularly 2 to 15, $R^{11}$ is hydrogen, alkyl, alkenyl or aryl, which is partially or completely fluorinated, if necessary, preferably hydrogen or methyl, $R^{12}$, $R^{13}$, $R^{14}$, $R^{15}$, $R^{16}$ and $R^{17}$, independent of one another, stand for hydrogen, alkyl, alkyloxy, alkenyl, alkenyloxy, alkynyl, alkynyloxy, aryl, aryloxy, aralkyl, aralkyloxy, alkylaryl and/or alkylaryloxy, which are partially or completely fluorinated, if necessary, preferably alkyl or alkenyl, and particularly $C_1$-$C_6$-alkyl, k and q, independent of one another, stand for 0 or 1, A1 stands for carbon or silicon, A2, A3 and A4, independent of one another, is a $C_dJ_{2d}$ group, where J and d have the meanings defined above, j, p and l, independent of one another, are 0 or 1, A5 stands for a bivalent bridge silicon, particularly —O—, —CO—O— or —CO—, $R^{18}$ is hydrogen, alkyl, alkenyl or aryl, which is partially or completely fluorinated, if necessary, preferably hydrogen or methyl, $R^{20}$, $R^{21}$, $R^{22}$ and $R^{23}$, independent of one another, stand for hydrogen, alkyl, alkyloxy, alkenyl, alkenyloxy, alkynyl, alkynyloxy, aryl, aryloxy, aralkyl, aralkyloxy, alkylaryl and/or alkylaryloxy, which are partially or completely fluorinated, if necessary, preferably alkyl or alkenyl, and particularly $C_1$-$C_6$-alkyl, BG is a bivalent bridge group, and $R^{19}$ and $R^{24}$, independent of one another, are hydrogen, alkyl, alkenyl or aryl, which are partially or completely fluorinated, if necessary, preferably hydrogen or methyl, with the proviso that of the groups $R^2$, $R^3$ and $R^4$ and/or the groups $R^5$, $R^6$ and $R^7$ and/or the groups $R^8$, $R^9$ and $R^{10}$ and/or the groups $R^{15}$, $R^{16}$ and $R^{17}$ and/or the groups $R^{20}$ and $R^{21}$ and/or the groups $R^{22}$ and $R^{23}$ and/or the groups $R^{20}$, $R^{21}$ and $R^{22}$, only one can be hydrogen, whereby f and h, within a molecule, can assume different values, within the framework of the given definition.

11. Dental impression mass according to claim 1, further comprising aside from the non-ionic surfactant and non-ionic fluorosurfactant, a polyether terminated with alkenyl groups and/or alkynyl groups, and/or a polyether terminated with hydroxyl and/or aryloxy and/or arylalkyloxy and/or alkoxy, as an additional component.

12. Dental impression mass according to claim 11, wherein the polyether terminated with alkenyl groups is a compound having the Formula XII, and the polyether terminated with hydroxyl and/or alkoxy is a compound having the Formula XIII

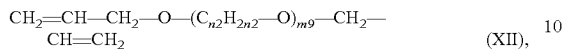

$$CH_2=CH-CH_2-O-(C_{n2}H_{2n2}-O)_{m9}-CH_2-CH=CH_2 \quad (XII),$$

$$R^{31}-O-(C_{n2}H_{2n2}-O)_{m9}-R^{32} \quad (XIII),$$

where n2 stands for a whole number from 2 to 8, preferably from 2 to 4, m9 is a whole number from 3 to 70000, preferably from 10 to 2500, $R^{31}$ and $R^{32}$, independent of one another, stand for hydrogen or $C_1$-$C_6$-alkyl, particularly hydrogen and/or methyl, ethyl or propyl, and whereby $R^{31}$, $R^{32}$, n2 and m9, within a molecule, can be different, within the framework of the given definitions.

13. Dental impression mass according to claim 1, further comprising aside from the silicon-containing non-ionic surfactant and non-ionic fluorosurfactant, a polyol as an additional component.

14. Dental impression mass according to claim 13, wherein the dental impression mass contains a polyether terminated with alkenyl groups and/or alkynyl groups, and/or polyether terminated with aryloxy and/or arylalkyloxy and/or hydroxyl and/or alkoxy, as an additional component.

15. Dental impression mass according to claim 13, wherein the polyol is selected from the group of polyvinyl alcohols, aliphatic diols, triols, tetraols, pentaols and/or hexaols, and mixtures of two or more of these polyols.

16. Dental impression mass according to claim 15, wherein the polyol is selected from the group of polyvinyl alcohols, polysaccharides, trimethylol propane, pentaerythritol, dipentaerythritol, glycerin, allyloxy-1,2-propane diol, 2-methyl-2, 4-pentane diol, trimethylol propane allyl ether, decane diol, nonane diol, octane diol, heptane diol, hexane diol, pentane diol, butane diol, propane diol, ethane dial, fructose, glucose, and mixtures of two or more of these polyols, particularly glycerin.

17. Dental impression mass according to claim 1, wherein the equilibrium ratio of surfactant to fluorosurfactant amounts to 100:1 to 1:100.

18. Dental impression mass according to claim 1, wherein the dental impression mass is an organopolysiloxane multi-component dental impression mass that crosslinks by means of an addition reaction, containing components A and B, where
  a) Component A contains an oxganopolysiloxane with at least two ethylene-unsaturated groups and a hydrosilylation catalyst,
  b) Component B contains an organohydrogen polysiloxane, and
  c) at least one of the Components A and/or B contains the non-ionic surfactant and/or the non-ionic fluorosurfactant, and Components A and B have a composition such that after the Components A and B are mixed, a combination of the non-ionic surfactant and the non-ionic fluorosurfactant is present.

19. Dental impression mass according to claim 1, wherein the dental impression mass is an organopolysiloxane multi-component dental impression mass that crosslinks by means of a condensation reaction, containing Components C and D, where
  d) Component C contains an organopolysiloxane with at least two hydroxyl groups,
  e) Component D contains a silicic acid ester, polysilicic acid ester and/or an organopolysiloxane with at least two alkoxy groups, as well as a condensation catalyst, and
  f) at least one of the Components C and/or D contains the non-ionic surfactant and/or the non-ionic fluorosurfactant, and Components C and D have a composition such that after the Components C and D are mixed, a combination of the non-ionic surfactant and non-ionic fluorosurfactant is present.

20. Dental impression mass according to claim 1, wherein the dental impression mass is a multi-component dental impression mass that crosslinks by means of an addition reaction and contains alkenyl groups, containing Components E and F, where
  g) Component E contains a crosslinking catalyst,
  h) Component F contains a crosslinkable polyether that contains alkenyl groups, as well as an organohydrogen polysiloxane and/or SiH-polyether, and
  i) at least one of the Components E and/or F contains the non-ionic surfactant and/or the non-ionic fluorosurfactant, and Components E and F have a composition such that after the Components E and F are mixed, a combination of the non-ionic surfactant and the non-ionic fluorosurfactant is present.

21. Dental impression mass according to claim 1, wherein the dental impression mass is a polyether multi-component dental impression mass containing alkoxy silyl groups, containing Components G and H, where
  j) Component G contains a crosslinkable polyether that contains alkoxy silyl groups,
  k) Component H contains water, and
  l) at least one of the Components G and/or H contains a catalyst as well as the non-ionic surfactant and/or the non-ionic fluorosurfactant, and Components G and H have a composition such that after the Components G and H are mixed, a combination of the non-ionic surfactant and the non-ionic fluorosurfactant is present.

22. Dental impression mass according to claim 1, wherein the curable polymers comprise crosslinkable polyethers that have alkoxy silyl groups, aziridino groups, groups derived from an ethylene-unsaturated carboxylic acid or alkenyl groups as crosslinkable groups, or groups that can crosslink by way of a ring-opening metathesis reaction.

23. Dental impression mass according to claim 22, wherein the fluorosurfactant is a non-ionic fluorosurfactant having at least one (poly)alkylene oxide groups, which comprises a partially fluoridated or perfluoridated hydrocarbon group that is connected with a (poly)alkylene oxide group by way of an oxygen atom or an ester group as a bridge group.

24. Dental impression mass according to claim 22, wherein the crosslinkable polyethers have alkoxy silyl group or aziridino group as crosslinkable groups, or wherein the crosslinkable polyethers have groups that can crosslink by way of a ring-opening metathesis reaction.

25. Dental impression mass according to claim 22, further comprising polyols and/or polyethers terminated with alkenyl group and/or alkynyl groups, and/or polyethers terminated with hydroxyl and/or alkoxy, as an additional component.

26. Dental impression mass according to claim 22, wherein the dental impression mass is a multi-component dental impression mass containing Components I and J, where m) Component I contains a crosslinkable polyether that contains alkoxy silyl group or aziridino group, or a polyether that contains groups that can crosslink by way of a ring-opening metathesis reaction, n) Component J contains a catalyst, and o) at least one of the Components I and/or J contains the non-ionic fluorosurfactant and the non-ionic surfactant, whereby Components I and J have a composition such that after the Components I and J are mixed, a combination of the non-ionic surfactant and the non-ionic fluorosurfactant is present.

27. Dental impression mass according to claim 1, wherein the dental impression mass has a crosslinkable polyalkylene ether that has group derived from acrylic acid and/or methacrylic acid, an initiator that can be activated chemically or by means of radiation, as well as a non-ionic fluorosurfactant.

28. Dental impression mass according to claim 1, wherein the dental impression mass is a multi-component dental impression mass that has polyethers that have groups that can crosslink by way of ring-opening metathesis polymerization (ROMP), polyethers that contain polysiloxanes and/or synthetic rubbers, containing Components K and L, where p) Component K contains polyethers, polysiloxanes and/or synthetic rubbers that have groups that can crosslink by way of ROMP, q) Component L contains a ROMP crosslinking catalyst, and r) at least one of the Components K and/or L contains the non-ionic surfactant and/or the non-ionic fluorosurfactant, whereby Components K and L have a composition such that after the Components K and L are mixed, a combination of the non-ionic surfactant and the non-ionic fluorosurfactant is present.

29. Dental impression mass according to claim 1, further comprising fillers in a total proportion of 0.01 to 80 wt. % with reference to the total dental impression mass.

30. Dental impression mass according to claim 1, wherein the dental impression mass contains one or more of the following additives: buffer salts, water collectors, paste-forming agents, other surfactants, active substances, plasticizers, substances that make optical scanning possible, flavor and/or scent substances, substances that make diagnostics possible, fluorination agents, bleach substances, desensitization agents, adhesion bond mediators, pigments, indicators, stabilizers (antioxidants) as well as antibacterial substances.

31. Dental impression mass according to claim 1, wherein the dental impression mass contains a) 25 to 85 wt. % organopolydialkyl siloxane with at least two alkenyl groups, b) 1 to 70 wt. % organohydrogen polysiloxane with an SiH content of 0.1 to 15.0 mmol/g, c) 0.0001 to 2 wt. % hydrosilylation catalyst, particularly salts, complexes and colloidally present forms of the transition metals of the $8^{th}$ secondary group, d) 0 to 90 wt. % non-reinforcing fillers with a BET surface of less than 50 $m^2$/g, e) 0.1 to 50 wt. % reinforcing fillers with a BET surface of greater than or equal to 50 $m^2$/g, f) 0 to 20 wt. % ancillary substances and additives, such as plasticizers, pigments, stabilizers, inhibitors, alkyl-closed fatty alcohol ethoxylates, g) 0.01 to 10.0 wt. % of a non-ionic surfactant containing at least one (poly)alkylene oxide radical as well as a group containing silicon, with a molecular mass of less than 6000 g/mol, which is a non-ionic polyether siloxane surfactant with 3 to 7 silicon atoms and/or a non-ionic polyether carbosilane surfactant with 1 to 7 silicon atoms in the carbosilane partial structure, and an alkylene oxide proportion of 1 to 20 units, and h) 0.001 to 10.0 wt. % of a non-ionic fluorosurfactant having at least one (poly)alkylene oxide group with 1 to 20 alkylene oxide units, containing at least one partially fluorinated or perfluorinated hydrocarbon group with 3 to 30 fluorine atoms, which is connected with the (poly)alkylene oxide group by way of an oxygen atom or an ester group, whereby the ratio of the surfactants g) and h) is preferably 100:1 to 1:100, particularly preferably 50:1 to 1:50, very particularly preferably 10:1 to 1:10, and especially preferably 5:1 to 1:5.

32. Dental impression mass according to claim 31, wherein the dental impression mass additionally contains i) 0.1 to 25 wt.-% branched or linear alkyl, hydroxy, alkynyl and/or alkenyl end-stopped polyalkylene ether and/or mixtures of them, whereby the weight ratio of the organopolysiloxane a) to the polyether i) is preferably 1:1 to 80:1, particularly preferably 1:1 to 60:1, very particularly preferably 1:1 to 40:1, and especially preferably 1:1 to 30:1.

33. Dental impression mass according to claim 32, wherein the dental impression mass is a two-component dental impression mass consisting of Component A and B, where Component A contains a) 10 to 80 wt. % organopolydialkyl siloxane with at least two alkenyl groups, c) 0.0001 to 2 wt. % hydrosilylation catalyst, particularly salts, complexes and colloidally present forms of the transition metals of the $8^{th}$ secondary group, d) 0 to 90 wt. % non-reinforcing fillers with a BET surface of less than 50 $m^2$/kg, e) 0.1 to 50 wt. % reinforcing fillers with a BET surface of greater than or equal to 50 $m^2$/kg, f) 0 to 20 wt. % ancillary substances and additives, such as plasticizers, pigments, stabilizers and/or inhibitors, and j) 0.001 to 5.0 wt. % alkyl-terminated, aryl-terminated, aralkyl-terminated non-ionic surfactants, preferably alkyl-terminated fatty alcohol ethoxylates, silicon surfactants, polyether carbosilanes, carbosilane surfactants and fluorosurfactants that are alkyl-terminated, and particularly alkyl-terminated fatty alcohol ethoxylates, and Component B contains a) 0.1 to 70 wt. % organopolydialkyl siloxane with at least two alkenyl groups, b) 1.2 to 80 wt. % organohydrogen polysiloxane with an SiH content of 0.1 to 15.0 mmol/kg, d) 0 to 90 wt. % non-reinforcing fillers with a BET surface of less than 50 $m^2$/kg, e) 0.1 to 50 wt. % reinforcing fillers with a BET surface of greater than or equal to 50 $m^2$/kg, f) 0 to 20 wt. % ancillary substances and additives, such as plasticizers, pigments, stabilizers and/or inhibitors, g) 0.01 to 10.0 wt. % of a non-ionic surfactant having at least one (poly)alkenylene oxide group and a group containing silicon, with a molecular mass of less than 6000 g/mol, which is a non-ionic polyether siloxane surfactant with 3 to 7 silicon atoms and/or a non-ionic polyether carbosilane surfactant with 1 to 7 silicon atoms in the carbosilane partial structure, and an alkylene oxide component of 1 to 20 units, h) 0.001 to 10.0 wt. % of a non-ionic fluorosurfactant having at least one (poly)alkylene oxide group with 1 to 20 alkylene oxide units, containing at least one partially fluoridated or perfluoridated hydrocarbon group with 3 to 30 fluorine atoms, which is connected with the (poly)alkylene oxide group by way of an oxygen atom or an ester group, whereby the ratio of the surfactants g) and h)

is 25:1 to 1:25, preferably 20:1 to 1:5, particularly preferably 10:1 to 1:5, and especially preferably 5:1 to 1:3, and i) 0.5 to 50 wt. % branched or linear alkyl and/or alkynyl and/or alkenyl and/or hydroxyl end-stopped polyalkylene ethers and/or mixtures of them, whereby the weight ratio of the organopolysiloxane a) to the polyether i) is preferably 1:50 to 50:1, particularly preferably 10:1 to 1:10, and especially preferably 4:1 to 1:5.

34. Dental impression mass according to claim 32, wherein it is a two-component dental impression mass consisting of Component A and B, where Component A contains a) 10 to 80 wt. % organopolydialkyl siloxane with at least two alkenyl groups, c) 0.0001 to 2 wt. % hydrosilylation catalyst, particularly salts, complexes and colloidally present forms of the transition metals of the 8$^{th}$ secondary group, d) 0 to 90 wt. % non-reinforcing fillers with a BET surface of less than 50 m$^2$/kg, e) 0.1 to 50 wt. % reinforcing fillers with a BET surface of greater than or equal to 50 m$^2$/kg, f) 0 to 20 wt. % ancillary substances and additives, such as plasticizers, pigments, stabilizers and/or inhibitors, and j) 0.001 to 5.0 wt. % alkyl-terminated, aryl-terminated, aralkyl-terminated non-ionic surfactants, preferably alkyl-terminated fatty alcohol ethoxylates, silicon surfactants, polyether carbosilanes, carbosilane surfactants and fluorosurfactants that are alkyl-terminated, and particularly alkyl-terminated fatty alcohol ethoxylates, and Component B contains a) 0.1 to 70 wt. % organopolydialkyl siloxane with at least two alkenyl groups, b) 1.2 to 80 wt. % organohydrogen polysiloxane with an SiH content of 0.1 to 15.0 mmol/kg, d) 0 to 90 wt. % non-reinforcing fillers with a BET surface of less than 50 m$^2$/kg, e) 0.1 to 50 wt. % reinforcing fillers with a BET surface of greater than or equal to 50 m$^2$/kg, f) 0 to 20 wt. % ancillary substances and additives, such as plasticizers, pigments, stabilizers and/or inhibitors, g) 0.01 to 10.0 wt. % non-ionic polyether siloxane surfactant with 3 to 7 silicon atoms in the siloxane partial structure and/or non-ionic polyether carbosilane surfactant with 1 to 7 silicon atoms in the carbosilane partial structure and an alkylene oxide proportion of 1 to 20 units, h) 0.001 to 10.0 wt. % non-ionic head-tail fluorosurfactant with a hydrophilic head that is formed from 1 to 20 alkylene oxide units and with a hydrophobic tail that is formed from partially or perfluoroalkyl groups with 3 to 30, preferably 5 to 29 fluorine atoms, whereby the ratio of the surfactants g) and h) is preferably 25:1 to 1:25, particularly preferably 20:1 to 1:5, very particularly preferably 10:1 to 1:5, and especially preferably 5:1 to 1:3, and k) 0.5 to 50 wt. % polyol and/or mixtures of polyols, whereby the weight ratio of the organopolysiloxane a) to the polyol k) is preferably 1:50 to 50:1, particularly preferably 10:1 to 1:10, and especially preferably 4:1 to 1:5.

35. Mixtures that can be obtained by mixing the dental impression masses according to claim 1.

36. Cured impression material that can be obtained by means of curing the dental impression masses according to claim 1.

37. Method for the production of an elastomer dental impression mass comprising the step of:

mixing (A) a non-ionic surfactant with a molecular mass of less than 6000 g/mol containing at least one (poly)alkylene oxide group as well as one silicon-containing group, and (B) a non-ionic fluorosurfactant that has at least one partially fluorinated or perfluorinated hydrocarbon group, which is connected with a (poly)alkylene oxide group, a hydrocarbon group, an aliphatic polyhydroxy group or a heterocyclic group that contains nitrogen, by way of an oxygen atom, an amino group, a keto group, a carboxylic acid ester group, a phosphoric acid ester group, a carboxylic acid amide group and/or a phosphoric acid amide group, or that has at least one partially fluorinated or perfluorinated hydrocarbon group and at least one amino oxide group, wherein the elastomer dental impression mass, 40 seconds after the start of mixing, has a low initial water droplet contact angle of <10°, measured at a droplet age of 10 seconds.

38. Method for the production of an elastomer dental impression mass according to claim 37, wherein alkenyl, alkynyl, alkyloxy, aryloxy, arylalkyloxy and/or hydroxy end-stopped polyalkylene ether is mixed with (A) and (B).

39. Method for the production of an elastomer dental impression mass according to claim 37, wherein polyol is mixed with (A) and (B).

40. Method for taking a dental impression comprising the steps of:

providing a dental impression mass containing:

curable polymers comprising organopolysiloxanes that crosslink by means of an addition reaction;

a non-ionic surfactant with a molecular mass of less than 6000 g/mol containing at least one (poly)alkylene oxide group as well as one silicon-containing group;

a non-ionic fluorosurfactant, that has at least one partially fluorinated or perfluorinated hydrocarbon group that (a) is connected with a (poly)alkylene oxide group by way of an oxygen atom, or (b) has at least one partially fluorinated or perfluorinated hydrocarbon group and at least one amino oxide group;

wherein the elastomer dental impression mass, 40 seconds after the start of mixing, has a low initial water droplet contact angle of <10° measured at a droplet age of 10 seconds; and using said dental impression mass as a doubling mass in dental technology to take a dental impression;

whereby a processing time for the dental impression amounts to between >0 and 30 minutes.

41. Dental impression mass containing:

curable polymers comprising organopolysiloxanes that crosslink by means of an addition reaction;

a non-ionic surfactant with a molecular mass of less than 6000 g/mol containing at least one (poly)alkylene oxide group as well as one silicon-containing group;

a non-ionic fluorosurfactant, that has at least one partially fluorinated or perfluorinated hydrocarbon group that (a) is connected with a (poly)alkylene oxide group by way of an oxygen atom, or (b) has at least one partially fluorinated or perfluorinated hydrocarbon group and at least one amino oxide group;

wherein the non-ionic surfactant containing at least one (poly)alkylene oxide group as well as one silicon-containing group is a compound having the Formula VII, VIII, IX or X

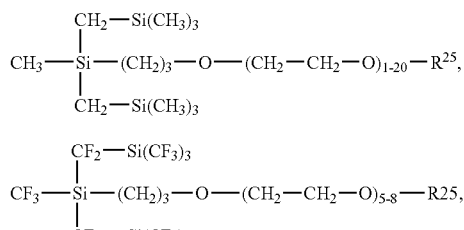

(VII)

$$CH_3-\underset{\underset{CH_2-Si(CH_3)_3}{|}}{\overset{\overset{CH_2-Si(CH_3)_3}{|}}{Si}}-(CH_2)_3-O-(CH_2-CH_2-O)_{1-20}-R^{25},$$

(VIII)

$$CF_3-\underset{\underset{CF_2-Si(CF_3)_3}{|}}{\overset{\overset{CF_2-Si(CF_3)_3}{|}}{Si}}-(CH_2)_3-O-(CH_2-CH_2-O)_{5-8}-R25,$$

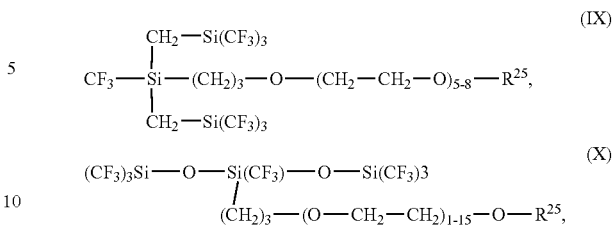

(IX)

$$CF_3-\underset{\underset{CH_2-Si(CF_3)_3}{|}}{\overset{\overset{CH_2-Si(CF_3)_3}{|}}{Si}}-(CH_2)_3-O-(CH_2-CH_2-O)_{5-8}-R^{25},$$

(X)

$$(CF_3)_3Si-O-\underset{\underset{(CH_2)_3-(O-CH_2-CH_2)_{1-15}-O-R^{25},}{|}}{Si(CF_3)}-O-Si(CF_3)_3$$

where $R^{25}$ is hydrogen, methyl, ethyl, propyl or butyl, preferably hydrogen or methyl.

* * * * *

UNITED STATES PATENT AND TRADEMARK OFFICE
CERTIFICATE OF CORRECTION

PATENT NO. : 7,812,065 B2
APPLICATION NO. : 12/087319
DATED : October 12, 2010
INVENTOR(S) : Bublewitz et al.

Page 1 of 1

It is certified that error appears in the above-identified patent and that said Letters Patent is hereby corrected as shown below:

ON THE TITLE PAGE: Item [73], the assignee should be corrected to read:
--Kettenbach GmbH & Co. KG--.

In Column 79, line 1, claim 8, please change "$R_f = -C_5F_{13}$" to correctly read:
--$R_f = -C_6F_{13}$--.

In Column 79, line 49, claim 8, please change "$R_f = -C_5F_{13}$" to correctly read:
--$R_f = -C_6F_{13}$--.

In Column 80, line 60, claim 8, please change "$-C_5F_{13}$" to correctly read -- $-C_6F_{13}$--.

In column 83, line 41, claim 16, after the word pentane, please change "dial" to correctly read: --diol--.

Signed and Sealed this

Thirteenth Day of December, 2011

David J. Kappos
*Director of the United States Patent and Trademark Office*